(12) United States Patent
Nishino et al.

(10) Patent No.: US 8,550,709 B2
(45) Date of Patent: Oct. 8, 2013

(54) IMAGING AREA SPECIFYING APPARATUS, RADIOGRAPHIC SYSTEM, IMAGING AREA SPECIFYING METHOD, RADIOGRAPHIC APPARATUS, AND IMAGING TABLE

(75) Inventors: Naoyuki Nishino, Kanagawa (JP); Kenji Takahashi, Kanagawa (JP); Haruyasu Nakatsugawa, Kanagawa (JP); Yutaka Yoshida, Kanagawa (JP); Keiji Tsubota, Kanagawa (JP); Yasunori Ohta, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 478 days.

(21) Appl. No.: 12/941,093

(22) Filed: Nov. 8, 2010

(65) Prior Publication Data

US 2011/0110497 A1    May 12, 2011

(30) Foreign Application Priority Data

Nov. 9, 2009  (JP) ................ 2009-256473
Jan. 5, 2010  (JP) ................ 2010-000679
Oct. 21, 2010  (JP) ................ 2010-236810
Oct. 21, 2010  (JP) ................ 2010-236811

(51) Int. Cl.
*G01D 18/00* (2006.01)
*G21K 1/00* (2006.01)

(52) U.S. Cl.
USPC ........................... 378/207; 378/145

(58) Field of Classification Search
USPC ........ 378/37, 41, 42, 51, 62, 91, 95, 98, 98.8, 378/145, 162, 165, 166, 189, 190, 193, 197, 378/204–207, 210
See application file for complete search history.

(56) References Cited

U.S. PATENT DOCUMENTS 4,259,583 A * 3/1981 Albert .................... 378/98.6
6,196,715 B1 * 3/2001 Nambu et al. .......... 378/197

FOREIGN PATENT DOCUMENTS

| JP | 2716949 B2 | 2/1998 |
| JP | 2000-134539 A | 5/2000 |
| JP | 2003-33343 A | 2/2003 |
| JP | 2007-215760 A | 8/2007 |
| JP | 2009-17484 A | 1/2009 |
| JP | 2009-32854 A | 2/2009 |
| JP | 2009-212389 A | 9/2009 |

* cited by examiner

*Primary Examiner* — Anastasia Midkiff
(74) *Attorney, Agent, or Firm* — SOLARIS Intellectual Property Group, PLLC

(57) ABSTRACT

An imaging area specifying apparatus that includes a storage component and a specifying component is provided. The storage component stores as correlation information a correlation value correlated with the amount of radiation emitted to each of a plurality of predetermined areas divided from a detection region of a radiation detector that outputs an electric signal indicating a radiological image represented by radiation which is emitted to the detection region for detecting the radiation. The specifying component specifies an imaging area capable of capturing the radiological image of a predetermined size while preventing variations in the amount of radiation emitted to each of the divided areas in the detection region, on the basis of the correlation information stored in the storage component.

20 Claims, 39 Drawing Sheets

FIG. 8

| IDENTIFICATION NUMBER | NUMBER OF IMAGING OPERATIONS (TIMES) |
|---|---|
| 1 | 12 |
| 2 | 14 |
| 3 | 9 |
| ⋮ | ⋮ |

FIG. 9

| IMAGING PORTION | SIZE REQUIRED FOR IMAGING |
|---|---|
| FINGER | 1 × 1 |
| HAND | 2 × 2 |
| BREAST | 3 × 3 |
| ⋮ | ⋮ |

FIG. 10

| SIZE | COMBINATION OF DIVIDED AREAS |
|---|---|
| 1 × 1 | 1 |
| | 2 |
| | ⋮ |
| | 8 |
| | 9 |
| 2 × 2 | 1, 2, 4, 5 |
| | 2, 3, 5, 6 |
| | 4, 5, 7, 8 |
| | 5, 6, 8, 9 |
| 3 × 3 | 1, 2, 3, 4, 5, 6, 7, 8, 9 |
| | ⋮ |

| CONDITIONS | STILL IMAGE CAPTURE MODE | FLUOROGRAPHY MODE |
|---|---|---|
| AMOUNT OF RADIATION WITH RESPECT TO STILL IMAGE CAPTURE MODE | 1 | 0.1 TO 0.01 TIME |
| FRAME RATE (FRAME/sec) | - | NORMAL 15~30 max 60~90 |
| SENSITIVITY | 1 | SEVERAL HUNDRED TIMES |
| SPEED | 1 | SEVERAL TEN TIMES |
| DYNAMIC RANGE | FOUR DIGITS | TWO DIGITS |

FIG. 25
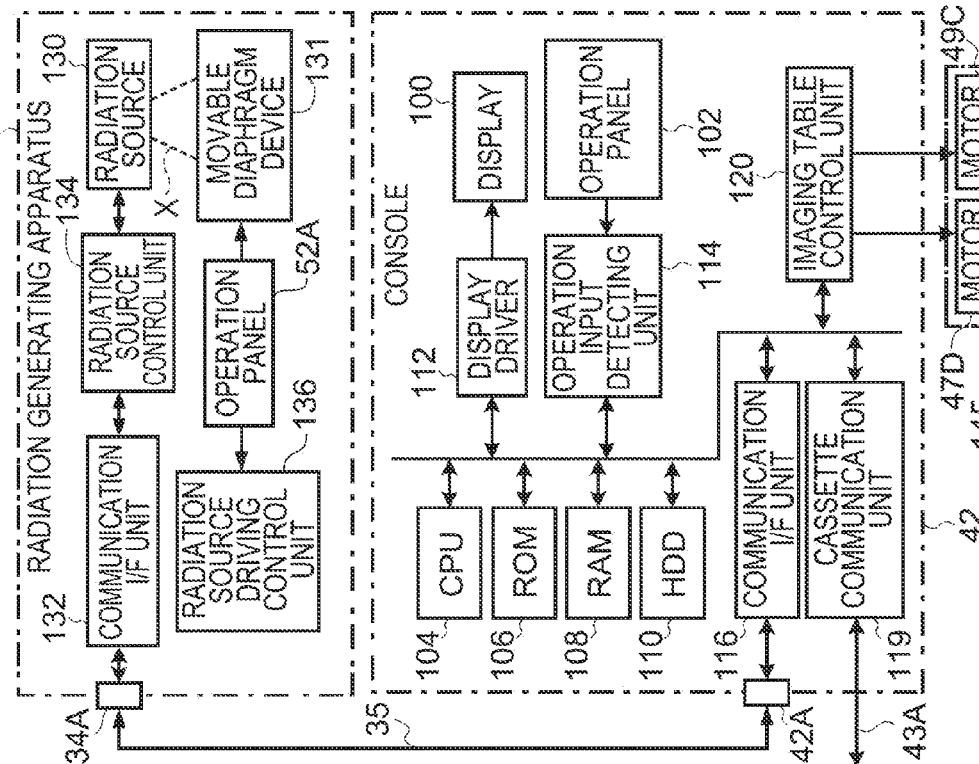
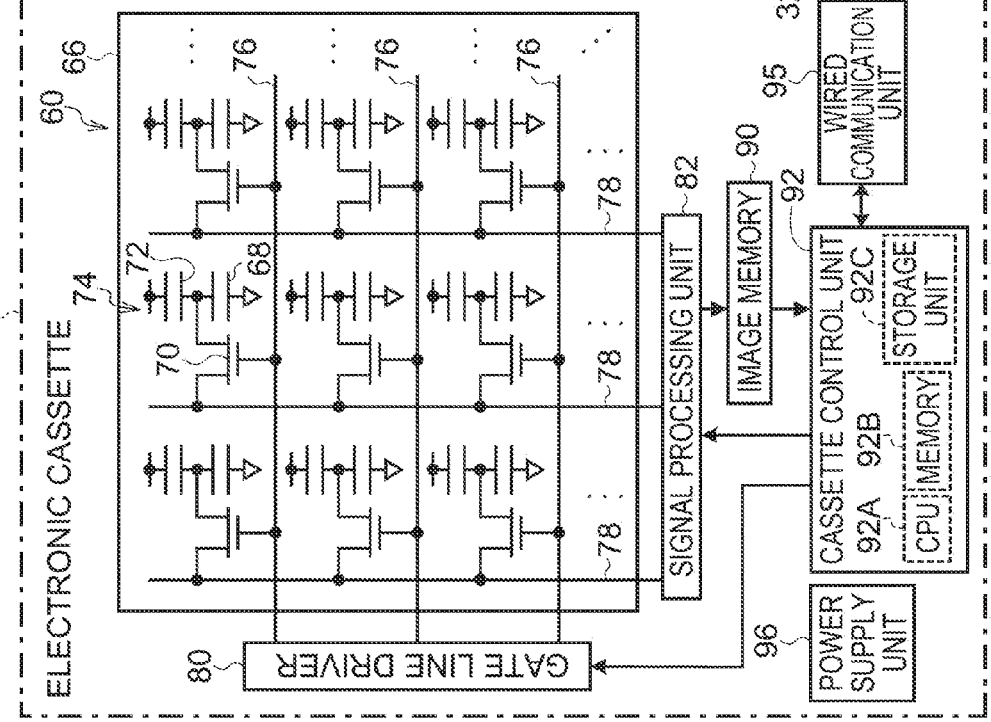

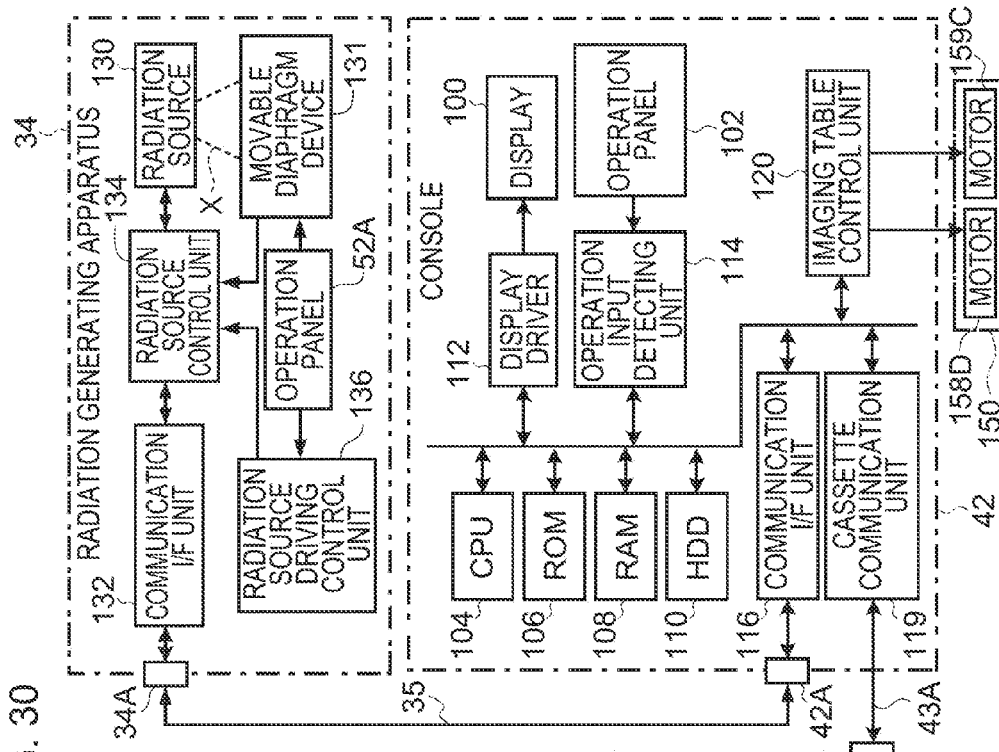
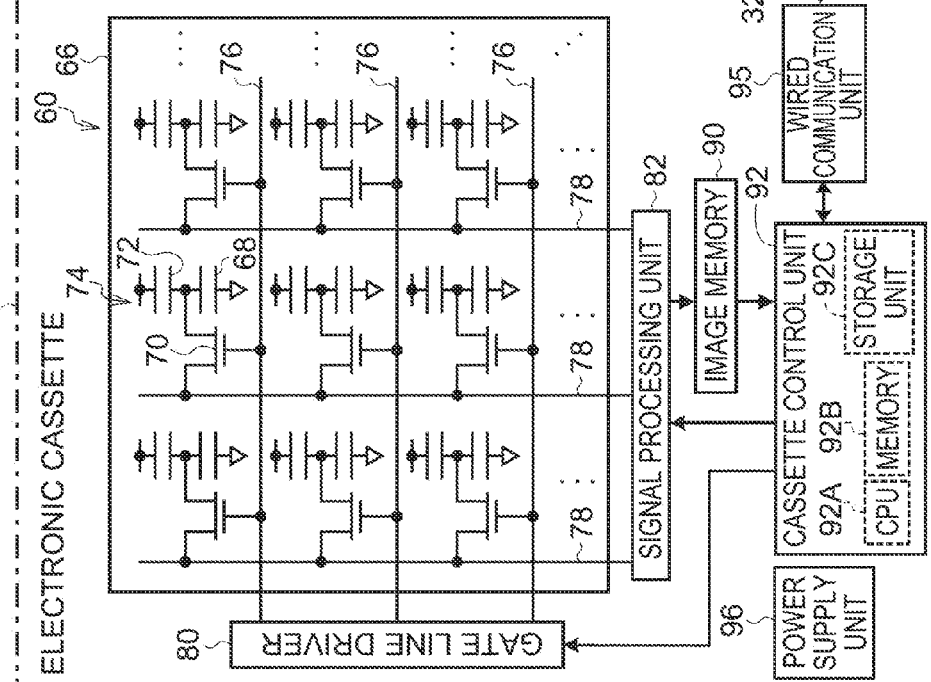
FIG. 30

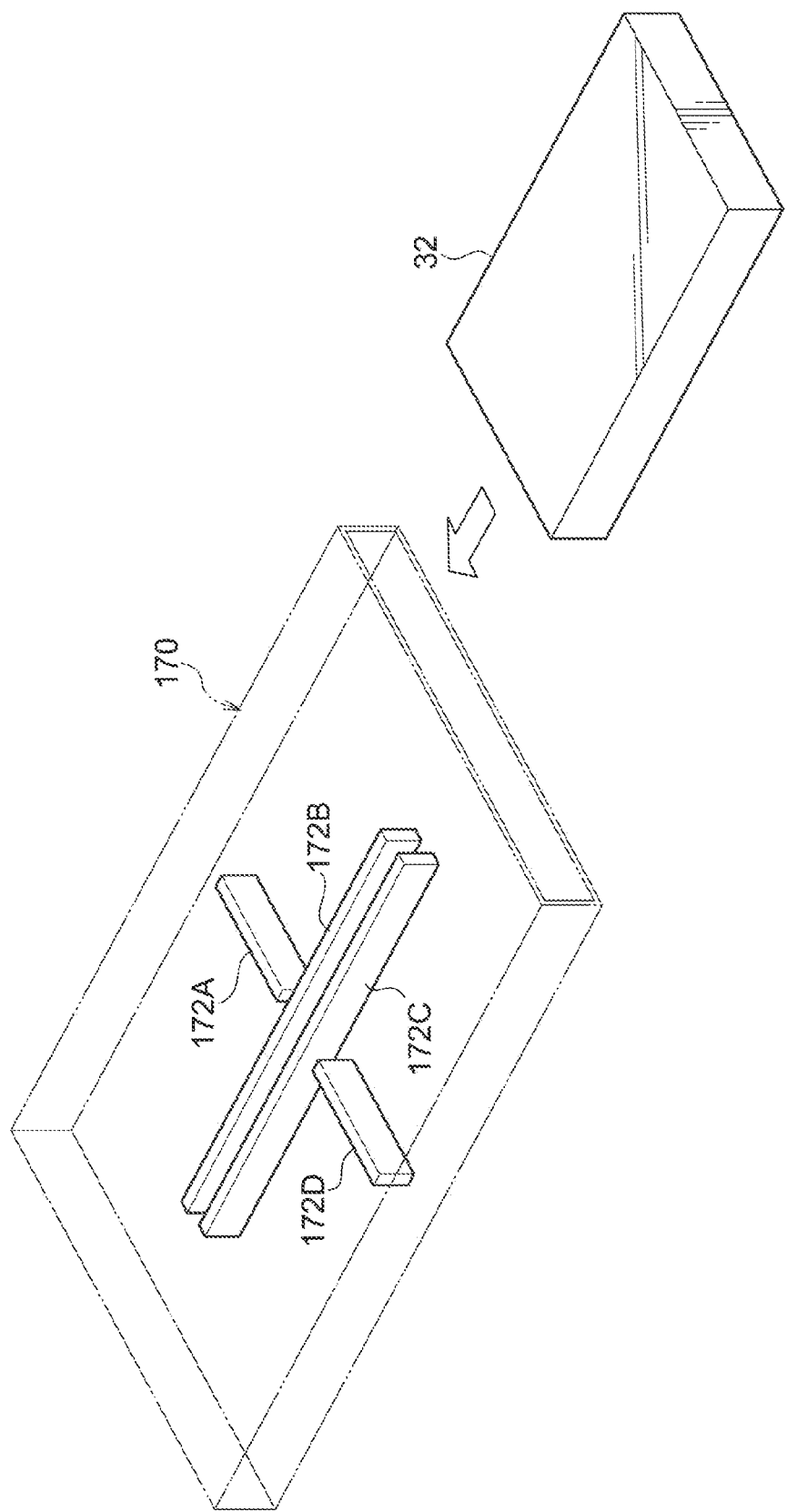

IMAGING AREA SPECIFYING APPARATUS, RADIOGRAPHIC SYSTEM, IMAGING AREA SPECIFYING METHOD, RADIOGRAPHIC APPARATUS, AND IMAGING TABLE

CROSS-REFERENCE TO RELATED APPLICATION

This application is based on and claims priority under 35 USC 119 from Japanese Patent Applications No. 2009-256473 filed on Nov. 9, 2009, No. 2010-000679 filed on Jan. 5, 2010, No. 2010-236810 filed on Oct. 21, 2010 and No. 2010-236811 filed on Oct. 21, 2010, the disclosures of which are incorporated by reference herein.

BACKGROUND OF THE INVENTION

1. Field of the Invention

The present invention relates to an imaging area specifying apparatus, a radiographic system, an imaging area specifying method, a radiographic apparatus, and an imaging table.

2. Description of the Related Art

In recent years, radiation detectors, such as flat panel detectors (FPD) that include a radiation sensitive layer provided on a thin film transistor (TFT) active matrix substrate, detect radiation, such as X-rays emitted, and output an electric signal indicating a radiological image represented by the detected radiation, have been put to practical use. The radiation detector has an advantage in that it enables the user to instantly check images including moving images, as compared to the X-ray film or the imaging plate according to the related art.

In addition, portable radiographic apparatuses (hereinafter, referred to as "electronic cassettes") that include the radiation detector and store radiological image data output from the radiation detector have been put to practical use. Since the electronic cassette has high portability, it can capture the image of the patient lying on a stretcher or a bed as they are, and it is easy to adjust the position of an imaging portion by changing the position of the electronic cassette. Therefore, it is possible to capture the image of a patient who cannot move.

However, in the cassette according to the related art including X-ray film or an imaging plate (IP), imaging is performed with a cassette having a film or an imaging plate with a size corresponding to an imaging portion or an imaging technique. This is because radiography is performed only on an imaging portion that needs to be observed considering the exposure of the patient and the periphery thereof and it is reasonable to use a film with a size corresponding to an imaging portion and the periphery thereof. Therefore, in the related art, cassettes with plural sizes are prepared.

Meanwhile, the electronic cassette is more expensive than the cassette including the X-ray film or the imaging plate. In addition, digital radiological image data is obtained by radiography, and a so-called trimming process of validating only data in a specific area in the radiological image data is easily performed. Therefore, a single-size electronic cassette can respond to plural imaging portions and imaging techniques by capturing images using the entire detection region for detecting radiation, or emitting radiation only to an imaging portion which needs to be observed and the periphery thereof using a portion of the detection region and trimming the image of the irradiated portion.

Japanese Patent Application Laid-Open (JP-A) No. 2003-33343 discloses a technique that divides the detection region into plural regions and performs an imaging operation in each of the divided regions.

Japanese Patent No. 2716949 and JP-A No. 2009-17484 disclose a technique that changes the reading range of pixel information from the radiation detector to narrow the imaging area of a radiological image and limits a region irradiated with radiation in correspondence with the imaging area such that fluorography is performed at a high frame rate, in a fluorography mode that continuously captures the image of an imaging portion which rapidly moves, such as the heart, to obtain a moving image.

However, in the technique disclosed in JP-A No. 2003-33343, in some cases, a specific portion of the detection region of the radiation detector deteriorates.

In the radiation detector, the region to which radiation is emitted deteriorates. Therefore, in a case in which an imaging operation is repeatedly performed using a specific portion of the detection region of the radiation detector, only that portion deteriorates. For example, as shown in FIG. 16, in a case in which there is a mark ("+" mark) indicating the center of the detection region, in many cases, the center of the detection region is used to perform an imaging operation. However, when an imaging operation is repeatedly performed using a central portion of the detection region, the central portion deteriorates, and the quality of the radiological image captured in the central portion deteriorates. In addition, in a case in which an imaging operation is performed using the entire detection region of the radiation detector, there is a difference in quality between the images captured in the central portion and a peripheral portion.

In particular, in fluorography, the number of shots is large and the total amount of radiation emitted to the radiation detector is more than that in the general still image capture mode. Therefore, as in Japanese Patent No. 2716949 and JP-A No. 2009-17484, in a case in which the imaging area of the radiological image is narrowed and the region irradiated with radiation is limited in correspondence with the imaging area, the imaging area deteriorates. For example, in fluorography, in general, the imaging area is limited to the central portion of the radiation detector and the central portion deteriorates. However, Japanese Patent No. 2716949 and JP-A-2009-17484 do not disclose any measures to prevent the deterioration.

In recent years, radiation detectors, such as flat panel detectors (FPD) that include a radiation sensitive layer disposed on a thin film transistor (TFT) active matrix substrate and can directly convert radiation, such as X-rays emitted, into digital data, have been put to practical use. The radiation detector has an advantage in that it enables the user to instantly check images and performs the fluorography mode (moving image capture mode) which continuously captures images, as compared to the X-ray film or the imaging plate according to the related art. Radiation conversion methods performed in the radiation detector include, for example, an indirect conversion method of converting radiation into light using a scintillator and converting the light into charge using a semiconductor layer, such as a photodiode, and a direct conversion method of converting radiation into charge using a semiconductor layer made of, for example, amorphous selenium. In each of the methods, there are various kinds of materials that can be used for the semiconductor layer.

However, a region to which radiation is emitted in the radiation detector deteriorates. Examples of the deterioration include irreversible deterioration in which radiation is repeatedly emitted to the semiconductor layer and the semiconductor layer gradually deteriorates, which causes a defective pixel, and reversible deterioration in which, when radiation is repeatedly emitted to the same region in a short time in the moving image capture mode, residual charge is gradually stored and the quality of the image deteriorates. The irreversible deterioration is likely to occur when the semiconductor layer is made of amorphous selenium. The reversible deterioration occurs when charge is stored in the semiconductor layer in the direct conversion method, and occurs when charge is stored in a photoelectric conversion unit (photodiode) in the indirect conversion method. The reversible deterioration is removed over time or by a removal process of removing the residual charge. However, it is difficult to perform the removal process while a moving image is captured.

JP-A No. 2000-134539 discloses a technique for obtaining a good radiological image using a radiation detector with defective pixels. In the technique, in one radiographic operation, the radiation detector is moved each time the radiological image is read, thereby reading plural radiological images from the radiation detector, and the read plural radiological images overlap each other such that the image of an object overlaps, thereby generating the image data of the radiological image.

JP-A No. 2007-215760 discloses a technique that reads pixel data of a portion of the detection region according to the exposure field range of radiation when an imaging apparatus using the radiation detector captures a moving image, in order to improve the reading speed of image data when the moving image is captured.

However, in the techniques disclosed in JP-A No. 2000-134539 and JP-A No. 2007-215760, in some cases, a specific portion of the detection region of the radiation detector deteriorates.

When an imaging operation is repeatedly performed using a specific portion of the detection region of the radiation detector, only the portion deteriorates. For example, when an imaging operation is repeatedly performed using a central portion of the detection region, the central portion deteriorates, and the quality of the radiological image captured in the central portion deteriorates. In particular, in fluorography, the number of shots is large and the total amount of radiation emitted to the radiation detector is more than that in the general still image capture mode.

SUMMARY OF THE INVENTION

The invention has been made in order to solve the above-mentioned problems, and an object of the invention is to provide an imaging area specifying apparatus, a radiographic system, and a method of specifying an imaging area capable of preventing the deterioration of a specific portion of a detection region of a radiation detector.

Another object of the invention is to provide a radiographic apparatus and an imaging table capable of preventing the deterioration of a specific portion of a detection region of a radiation detector.

A first aspect of the present invention is to provide an imaging area specifying apparatus that includes: a storage component that stores as correlation information a correlation value correlated with the amount of radiation emitted to each of a plurality of predetermined areas divided from a detection region of a radiation detector that outputs an electric signal indicating a radiological image represented by radiation which is emitted to the detection region for detecting the radiation; and a specifying component that specifies an imaging area capable of capturing the radiological image of a predetermined size while preventing variations in the amount of radiation emitted to each of the divided areas in the detection region, on the basis of the correlation information stored in the storage component.

A second aspect of the present invention is to provide the imaging area specifying apparatus of the first aspect that further includes: an acquiring component that acquires imaging portion information indicating an imaging portion, which is an imaging target. The storage component further stores size information indicating the size of an area required to capture the radiological image of each imaging portion of an object whose radiological image is to be captured, and the specifying component calculates the size of an area required to capture the image of the imaging portion indicated by the imaging portion information acquired by the acquiring component on the basis of the size information stored in the storage component, and specifies an imaging area capable of capturing a radiological image with the size while preventing variations in the amount of radiation emitted to each of the divided areas in the detection region on the basis of the correlation information.

A third aspect of the present invention is to provide the imaging area specifying apparatus of the first aspect, wherein the specifying component calculates the sum of the correlation values of the divided areas in each range with the size of an area required to capture the image of an imaging portion in the detection region on the basis of the correlation information and specifies a range with the minimum sum as the imaging area.

A fourth aspect of the present invention is to provide the imaging area specifying apparatus of the first aspect, wherein the specifying component calculates the maximum value of the correlation value of each divided area in each range with the size of an area required to capture the image of an imaging portion in the detection region on the basis of the correlation information and specifies the range with the smallest value of the maximum values as the imaging area.

A fifth aspect of the present invention is to provide the imaging area specifying apparatus of the first aspect that further includes: a presentation component that presents the imaging area specified by the specifying component.

A sixth aspect of the present invention is to provide the imaging area specifying apparatus of the first aspect that further includes: a control component that controls a limiting component, which limits an irradiation range of the radiation, of a radiation generating apparatus which generates radiation such that the radiation is emitted from the radiation generating apparatus to the imaging area specified by the specifying component.

A seventh aspect of the present invention is to provide the imaging area specifying apparatus of the first aspect that further includes: a conversion component. The correlation value is a number of imaging operations or an emission time of radiation in one mode of a still image capture mode that captures one image at a time or a fluorography mode that continuously captures an image, and the conversion component converts the correlation value in the other mode of the still image capture mode or the fluorography mode into the correlation value in the one mode.

An eighth aspect of the present invention is to provide a radiographic system that includes: a radiographic apparatus including a radiation detector that outputs an electric signal indicating a radiological image represented by radiation which is emitted to a detection region for detecting the radiation; an imaging area specifying apparatus including a storage component that stores as correlation information a correlation value correlated with the amount of radiation emitted to each of a plurality of predetermined areas divided from the detection region, and a specifying component that specifies an imaging area capable of capturing the radiological image of a predetermined size while preventing variations in the amount of radiation emitted to each of the divided areas in the detection region, on the basis of the correlation information stored in the storage component; and a presentation component that presents the imaging area specified by the specifying component.

A ninth aspect of the present invention is to provide the radiographic system of the eighth aspect that further includes: a detection component that detects whether an imaging portion is disposed at a position where a radiological image is captured in the imaging area of the radiation detector specified by the specifying component; and a permission component that permits the emission of radiation from a radiation generating apparatus which generates the radiation to the imaging area in a case in which the detection component detects that the imaging portion is disposed at the position where the radiological image is captured in the imaging area.

A tenth aspect of the present invention is to provide the radiographic system of the ninth aspect, wherein the radiation detector converts radiation into light using a scintillator that converts radiation into light and outputs an electric signal indicating a radiological image represented by the light, and the scintillator is formed so as to include a columnar crystal of a phosphor material.

A eleventh aspect of the present invention is to provide the radiographic system of the tenth aspect, wherein the storage component further stores irradiation information related to the intensity and emission time of radiation emitted to each of the divided areas, and the specifying component specifies the imaging area on the basis of the irradiation information such that the divided area in which a recovery period required to recover a temporary variation in sensitivity caused by the emission of radiation with sufficient intensity to cause the temporary variation in sensitivity has not elapsed is out of the imaging area or the divided area does not overlap a portion of interest of the imaging portion.

A twelfth aspect of the present invention is to provide the radiographic system of the eleventh aspect that further includes: a temperature detecting component that detects the temperature of the radiation detector, wherein the specifying component changes the recovery period such that, as the temperature of the radiation detector detected by the temperature detecting component increases, the recovery period is shortened.

A thirteenth aspect of the present invention is to provide a method of specifying an imaging area that includes: storing, as correlation information a correlation value correlated with an amount of radiation emitted to each of a plurality of predetermined areas divided from a detection region of a radiation detector that outputs an electric signal indicating a radiological image represented by radiation which is emitted to the detection region for detecting the radiation in a storage component; and specifying an imaging area capable of capturing the radiological image of a predetermined size while preventing variations in the amount of radiation emitted to each of the divided areas in the detection region, on the basis of the correlation information stored in the storage component.

A fourteenth aspect of the present invention is to provide a radiographic apparatus includes: a radiation detector that outputs an electric signal indicating a radiological image represented by radiation which is emitted to a detection region for detecting the radiation; a radiation source that emits the radiation to the radiation detector; an irradiation region changing component that changes an irradiation region to which the radiation is emitted from the radiation source in the detection region; and a control component that controls the irradiation region changing component to change the position of the irradiation region in the detection region such that the radiation is emitted to the detection region while being dispersed.

A fifteenth aspect of the present invention is to provide the radiographic apparatus of the fourteenth aspect, wherein the irradiation region changing component performs at least one of movement or rotation of the radiation detector with the detection region facing the radiation, movement of the radiation source, or a change in the emission direction of the radiation from the radiation source, thereby changing the irradiation region in the detection region.

A sixteenth aspect of the present invention is to provide the radiographic apparatus of the fourteenth aspect, wherein the control component controls the irradiation region changing component in a fluorography mode that continuously captures an image such that the irradiation region is moved in the detection region during fluorography, and controls the irradiation region changing component in a still image capture mode that captures one image at a time such that the irradiation region is moved in the detection region in synchronization with the capture of a still image, and controls the irradiation region changing component in the fluorography mode that captures a still image such that the irradiation region is moved in the detection region during at least one of a switching timing from the fluorography mode to the still image capture mode and a switching timing from the still image capture mode to the fluorography mode.

A seventeenth aspect of the present invention is to provide the radiographic apparatus of the sixteenth aspect, wherein the control component controls the irradiation region changing component such that the irradiation region is moved in the detection region each time a predetermined number of fluorographic operations are performed or each time a predetermined amount of radiation is emitted during the fluorography.

A eighteenth aspect of the present invention is to provide the radiographic apparatus of the fourteenth aspect that further includes: a storage component that stores as correlation information a correlation value correlated with the amount of radiation emitted to each of a plurality of predetermined areas divided from detection region; and a specifying component that specifies an imaging area capable of capturing a radiological image of a predetermined size while preventing variations in the amount of radiation emitted to each of the divided areas in the detection region, on the basis of the correlation information stored in the storage component. The control component controls the irradiation region changing component such that the imaging area specified by the specifying component is the irradiation region.

A nineteenth aspect of the present invention is to provide the radiographic apparatus of the eighteenth aspect that further includes: an acquiring component that acquires imaging portion information indicating an imaging portion, which is an imaging target. The storage component further stores size information indicating the size of an area required to capture the radiological image of each imaging portion of an object whose radiological image is to be captured, and the specifying component calculates a size of an area required to capture the image of the imaging portion indicated by the imaging portion information acquired by the acquiring component on the basis of the size information stored in the storage component, and specifies an imaging area capable of capturing a radiological image with the size while preventing variations in the amount of radiation emitted to each of the divided areas in the detection region on the basis of the correlation information.

A twentieth aspect of the present invention is to provide the radiographic apparatus of the eighteenth aspect, wherein the specifying component calculates the sum of the correlation values of the divided areas in each range with the size of an area required to capture the image of an imaging portion in the detection region on the basis of the correlation information and specifies a range with the minimum sum as the imaging area.

A twenty-first aspect of the present invention is to provide the radiographic apparatus of the fourteenth aspect, wherein the radiation detector converts radiation into light using a scintillator that converts radiation into light and outputs an electric signal indicating a radiological image represented by the light, and the scintillator is formed so as to include a columnar crystal of a phosphor material.

A twenty-second aspect of the present invention is to provide the radiographic apparatus of the twenty-first aspect, wherein the storage component further stores irradiation information related to the intensity and emission time of radiation emitted to each of the divided areas, and the specifying component specifies the imaging area on the basis of the irradiation information such that the divided area in which a recovery period required to recover a temporary variation in sensitivity caused by the emission of radiation with sufficient intensity to cause the temporary variation in sensitivity has not elapsed is out of the imaging area or the divided area does not overlap a portion of interest of the imaging portion.

A twenty-third aspect of the present invention is to provide the radiographic apparatus of the twenty-second aspect that further includes: a temperature detecting component that detects the temperature of the radiation detector, wherein the specifying component changes the recovery period such that, as the temperature of the radiation detector detected by the temperature detecting component increases, the recovery period is shortened.

A twenty-fourth aspect of the present invention is to provide an imaging table that includes: an accommodating unit that accommodates a cassette including a radiation detector which outputs an electric signal indicating a radiological image represented by radiation which is emitted to a detection region for detecting the radiation; and an irradiation region changing component that performs at least one of movement or rotation of the cassette accommodated in the accommodating unit or a change in the position of the cassette accommodated in the accommodating unit, thereby changing an irradiation region to which radiation is emitted from a radiation source in the detection region.

A twenty-fifth aspect of the present invention is to provide an imaging table that comprises: a radiation detector which outputs an electric signal indicating a radiological image represented by radiation which is emitted to a detection region for detecting the radiation; and an irradiation region changing component that performs at least one of movement or rotation of the radiation detector, thereby changing an irradiation region to which radiation is emitted from a radiation source in the detection region.

According to the invention, it is possible to prevent the deterioration of a specific portion of a detection region of a radiation detector.

BRIEF DESCRIPTION OF THE DRAWINGS

FIG. 8 is a diagram schematically illustrating an example of the data structure of correlation information according to the embodiment;

FIG. 9 is a diagram schematically illustrating an example of the data structure of size information according to the embodiment;

FIG. 10 is a diagram schematically illustrating an example of the data structure of divided area combination information according to the embodiment;

FIG. 25 is a block diagram illustrating the detailed structure of a radiographic system according to the third embodiment;

FIG. 30 is a block diagram illustrating the detailed structure of the radiographic system according to the fourth embodiment;

FIG. 35 is a perspective view illustrating the structure of an accommodating unit of an imaging table according to another embodiment;

DETAILED DESCRIPTION OF THE INVENTION

Hereinafter, exemplary embodiments of the invention will be described in detail with reference to the accompanying drawings.

[First Embodiment]

First, the structure of a radiology information system 10 according to this embodiment will be described.

Figure 1:
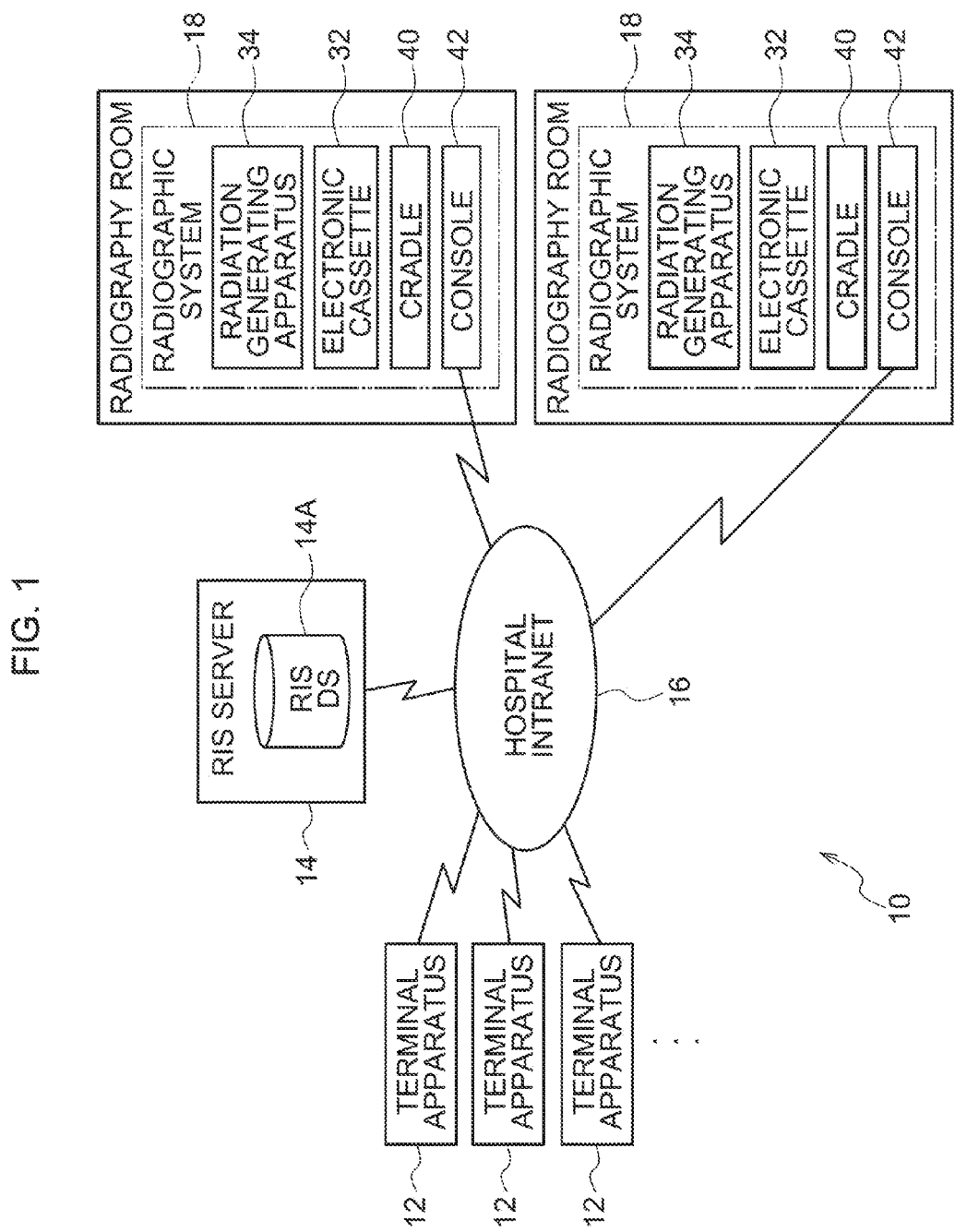
FIG. 1 is a block diagram illustrating the structure of a radiology information system according to an embodiment of the invention.

FIG. 1 is a block diagram illustrating each component of the radiology information system 10 (hereinafter, referred to an "RIS 10") according to this embodiment.

The RIS 10 is a system for managing information, such as a medical reservation and a diagnosis record, in the department of radiology and forms a portion of a hospital information system (hereinafter, referred to as an "HIS").

The RIS 10 includes plural imaging request terminal apparatuses 12 (hereinafter, also referred to as "terminal apparatuses 12"), an RIS server 14, and plural radiographic systems 18 (hereinafter, also referred to as "imaging systems 18") that are provided in each radiography room (or an operating room) in the hospital, and the components are connected to a hospital intranet (a network in a hospital) 16, such as a wired or wireless LAN (Local Area Network). An HIS server that manages the overall operation of the HIS is also connected to the hospital intranet 16.

The terminal apparatus 12 is for the doctor or the radiographer to input or read diagnosis information or equipment reservation, and is also used to input a request to capture a radiological image or an imaging reservation. The terminal apparatuses 12 each include a personal computer having a display device and can communicate with each other through the RIS server 14 and the hospital intranet 16.

The RIS server 14 receives an imaging request from each of the terminal apparatuses 12 and manages the radiography schedule of the imaging system 18. The RIS server 14 includes a database 14A.

The database 14A stores information (hereinafter, referred to as "patient information") about the patient, such as the attribute information of the patient (for example, name, ID, sex, date of birth, age, blood type, and weight), clinical history, medical examination history, and previously captured radiological images, information (hereinafter, referred to as "electronic cassette information") about an electronic cassette 32, which will be described below, used in the imaging system 18, such as an identification number, a type, a size, sensitivity, a usable imaging portion, starting date of use, and the number of times the electronic cassette 32 has been used, and environment information indicating an environment in which the electronic cassette 32 is used to capture a radiological image, that is, an environment in which the electronic cassette 32 is used (for example, a radiography room or an operating room).

The imaging system 18 is operated by the doctor or the radiographer to capture a radiological image according to an instruction from the RIS server 14. The imaging system 18 includes a radiation generating apparatus 34 that irradiates the patient with a dose of radiation X (see FIG. 3) corresponding to exposure conditions from a radiation source 130 (see FIG. 2), the electronic cassette 32 including a radiation detector 60 (see FIG. 3) that absorbs the radiation X passing through an imaging portion of the patient, generates charge, and generates image information indicating a radiological image on the basis of the amount of generated charge, a cradle 40 that charges a battery provided in the electronic cassette 32, and a console 42 that controls the electronic cassette 32, the radiation generating apparatus 34, and the cradle 40.

Figure 2:
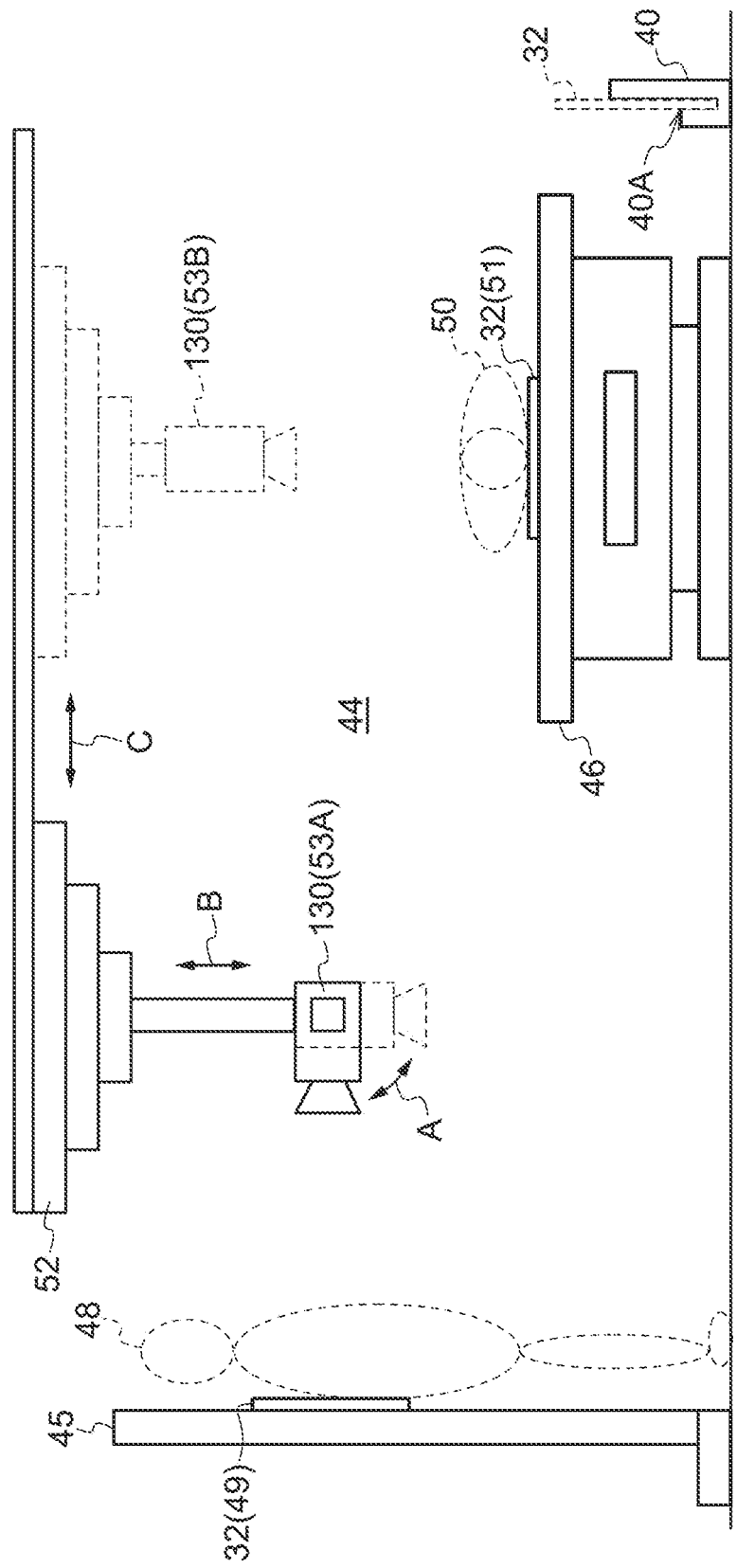
FIG. 2 is a diagram illustrating an example of a radiography room in which a radiographic system according to the embodiment is installed.

FIG. 2 shows an example of the arrangement of the imaging system 18 according to this embodiment in a radiography room 44.

As shown in FIG. 2, the radiography room 44 includes a rack 45 for holding the electronic cassette 32 when radiography is performed at a standing position and a bed 46 on which the patient lies when radiography is performed at a supine position. The front space of the rack 45 is a patient imaging position 48 when radiography is performed at the standing position, and the upper space of the bed 46 is a patient imaging position 50 when radiography is performed at the supine position.

In addition, the radiography room 44 includes a supporting/moving mechanism 52 that can rotate the radiation source 130 about the horizontal axis (the direction of an arrow A in FIG. 2), move the radiation source 130 in the vertical direction (the direction of an arrow B in FIG. 2), and movably support the radiation source 130 in the horizontal direction (the direction of an arrow C in FIG. 2) such that radiography can be performed at both the standing position and the supine position with radiation from a single radiation source 130. The supporting/moving mechanism 52 includes a driving source that rotates the radiation source 130 about the horizontal axis, a driving source that moves the radiation source 130 in the vertical direction, and a driving source that moves the radiation source 130 in the horizontal direction.

The cradle 40 includes an accommodating unit 40A capable of accommodating the electronic cassette 32.

The electronic cassette 32 is accommodated in the accommodating unit 40A of the cradle 40 in a standby state, in which the battery provided in the electronic cassette 32 is charged. When a radiological image is captured, the electronic cassette 32 is taken out from the cradle 40 by the radiographer. When the imaging position is the standing position, the electronic cassette 32 is moved and located at a position 49 where it is held by the rack 45. When the imaging position is the supine position, the electronic cassette 32 is moved and disposed at a position 51 on the bed 46.

In the imaging system 18 according to this embodiment, the radiation generating apparatus 34 and the console 42 are connected to each other by a cable such that various kinds of information can be transmitted therebetween by wired communication. In addition, in the imaging system 18 according to this embodiment, various kinds of information are transmitted between the electronic cassette 32 and the console 42 by wireless communication.

The electronic cassette 32 is used not only in the radiography room or the operating room, but may be used, for example, for a medical examination or doctor's rounds in the hospital since it is portable.

Figure 3:
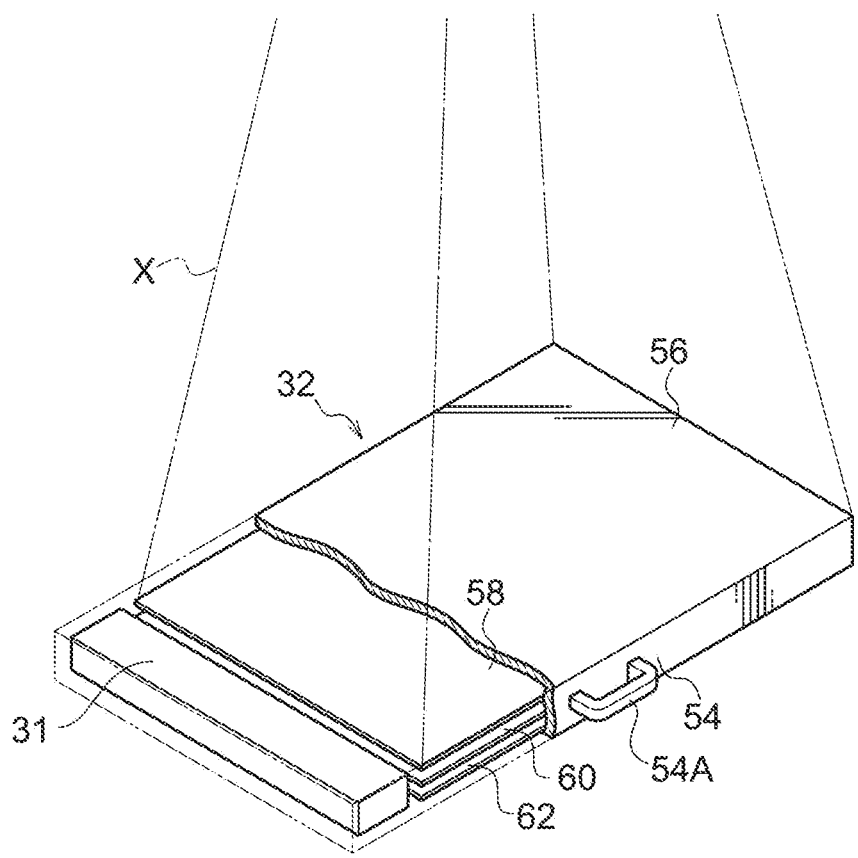
FIG. 3 is a perspective view illustrating the internal structure of an electronic cassette according to the embodiment.

FIG. 3 shows the internal structure of the electronic cassette 32 according to this embodiment.

As shown in FIG. 3, the electronic cassette 32 includes a housing 54 made of a material transmitting the radiation X and has water resistance and airtightness. When the electronic cassette 32 is used in, for example, the operating room, blood or other contaminants are likely to adhere to the electronic cassette 32. Therefore, the electronic cassette 32 is configured so as to have water resistance and airtightness. If necessary, an antiseptic wash is performed on the electronic cassette 32 such that one electronic cassette 32 can be repeatedly used.

A grid 58 that removes scattered rays of the radiation X by the patient, a radiation detector 60 that detects the radiation X passing through the patient, and a lead plate 62 that absorbs back-scattered rays of the radiation X are provided in the housing 54 in sequential order from an irradiation surface 56 of the housing 54 to which the radiation X is emitted. The irradiation surface 56 of the housing 54 may be configured as the grid 58.

A case 31 that accommodates an electronic circuit including a microcomputer and a chargeable secondary battery is provided at one end of the inside of the housing 54. The radiation detector 60 and the electronic circuit are operated by power supplied from the secondary battery in the case 31. It is preferable that, for example, a lead plate be provided on the irradiation surface 56 of the case 31 in order to prevent various kinds of circuits in the case 31 from being damaged by the radiation X. The electronic cassette 32 according to this embodiment has a rectangular parallelepiped shape in which the irradiation surface 56 has a rectangular shape, and the case 31 is arranged at one end of the electronic cassette 32 in the longitudinal direction. A handle 54A used to move the electronic cassette 32 is provided at a predetermined position on the outer wall of the housing 54.

Figure 4:
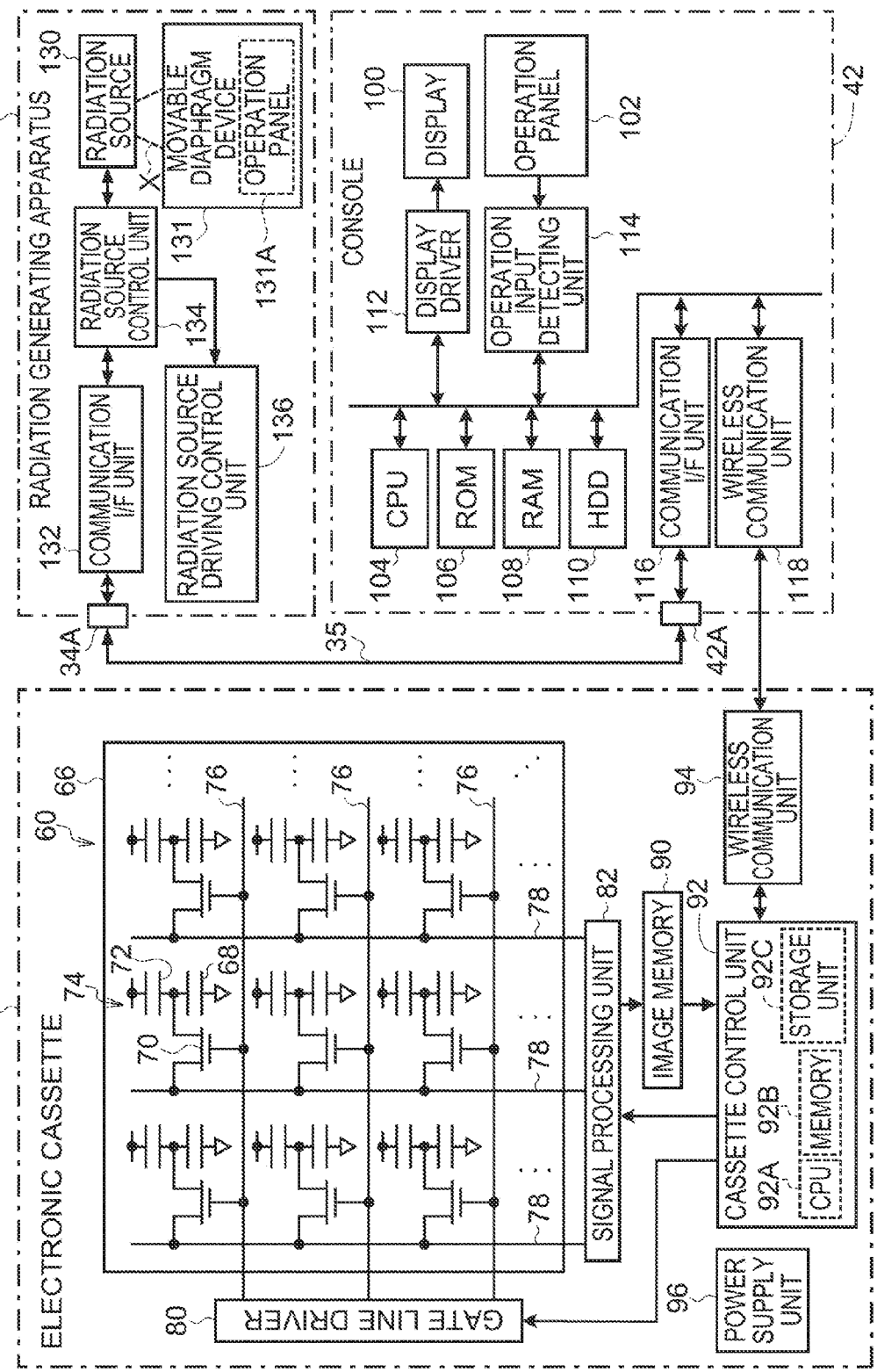
FIG. 4 is a block diagram illustrating the detailed structure of a radiographic system according to a first embodiment.

FIG. 4 is a block diagram illustrating the structure of a main part of an electric system of the radiographic system 18 according to the first embodiment.

As shown in FIG. 4, the radiation generating apparatus 34 includes a connection terminal 34A for communcation with the console 42. The console 42 includes a connection terminal 42A for communication with the radiation generating apparatus 34. The connection terminal 34A of the radiation generating apparatus 34 and the connection terminal 42A of the console 42 are connected to each other by a communication cable 35.

The radiation detector 60 provided in the electronic cassette 32 may be an indirect conversion type that coverts radiation into light using a scintillator and then converts the light into charge using a photoelectric conversion element, such as a photodiode, or a direct conversion type that converts radiation into charge using a semiconductor layer, such as an amorphous selenium layer. The radiation detector 60 of the direct conversion type is formed by laminating a photoelectric conversion layer that absorbs the radiation X and converts it into charge on a TFT active matrix substrate 66. The photoelectric conversion layer is made of, for example, amorphous a-Se (amorphous selenium) including selenium as a main component (for example, the content of selenium is equal to or more than 50%). When the radiation X is emitted to the photoelectric conversion layer, the quantity of charge (a pair of an electron and a hole) corresponding to the amount of radiation emitted is generated in the photoelectric conversion layer. In this way, the photoelectric conversion layer converts the emitted radiation X into charge. The radiation detector 60 of the indirect conversion type converts the radiation into charge using a phosphor material and a photoelectric conversion element (photodiode), instead of the radiation-to-charge conversion material for directly converting the radiation X into charge, such as amorphous selenium. As the phosphor material, gadolinium oxysulfide (GOS) or cesium iodide (CsI) is known. In this case, the phosphor material converts the radiation X into light and the photodiode, which is a photoelectric conversion element, converts light into charge.

In addition, plural storage capacitors 68 that store the charge generated in the photoelectric conversion layer or the photoelectric conversion element and plural pixel units 74 (in FIG. 4, the photoelectric conversion layer or the photoelectric conversion element corresponding to each pixel unit 74 is schematically shown as a sensor unit 72), each having a TFT 70 that reads the charge stored in the storage capacitor 68, are arranged in a matrix on the TFT active matrix substrate 66. When the radiation X is emitted to the electronic cassette 32, the charge generated in the sensor unit is stored in the storage capacitor 68 of each pixel unit 74. In this way, image information carried by the radiation X emitted to the electronic cassette 32 is converted into charge information and is then held in the radiation detector 60.

In addition, plural gate lines 76 that extend in a predetermined direction (row direction) and are used to turn on or off the TFT 70 of each pixel unit 74 and plural data lines 78 that extend in a direction (column direction) orthogonal to the gate lines 76 and are used to read the stored charge from the storage capacitor 68 through the TFT 70 in an on state are provided on the TFT active matrix substrate 66. Each gate line 76 is connected to a gate line driver 80, and each data line 78 is connected to a signal processing unit 82. When charge is stored in the storage capacitor 68 of each pixel unit 74, each row of the TFTs 70 of the pixel units 74 is sequentially turned on in response to the signal supplied from the gate line driver 80 through the gate line 76. The charge stored in the storage capacitor 68 of the pixel unit 74 having the TFT 70 turned on is transmitted as an analog electric signal to the data line 78 and is then input to the signal processing unit 82. Therefore, the charge stored in each row of the storage capacitors 68 of the pixel units 74 is sequentially read.

The signal processing unit 82 includes amplifiers and sample/hold circuits provided for each data line 78. A charge signal transmitted through each data line 78 is amplified by the amplifier and is then held by the sample/hold circuit. A multiplexer and an A/D (analog/digital) convertor are sequentially connected to the output side of the sample/hold circuit, and the charge signal held by the individual sample/hold circuit is sequentially (serially) input to the multiplexer and is then converted into digital image data by the A/D convertor.

An image memory 90 is connected to the signal processing unit 82, and the image data output from the A/D convertor of the signal processing unit 82 is sequentially stored in the image memory 90. The image memory 90 has storage capacity capable of storing image data corresponding to a predetermined number of frames. Whenever radiography is performed, image data obtained by the radiography is sequentially stored in the image memory 90.

The image memory 90 is connected to a cassette control unit 92 that controls the overall operation of the electronic cassette 32. The cassette control unit 92 is configured as a microcomputer and includes a CPU (Central Processing Unit) 92A, a memory 92B including a ROM and a RAM, and a non-volatile storage unit 92C, such as an HDD or a flash memory.

A wireless communication unit 94 is connected to the cassette control unit 92. The wireless communication unit 94 corresponds to a wireless LAN (Local Area Network) standard whose representative example is an IEEE (Institute of Electrical and Electronics Engineers) 802.11a/b/g, and controls the transmission of various kinds of information between an external apparatus and the electronic cassette 32 by wireless communication. The cassette control unit 92 can wirelessly communicate with the console 42 through the wireless communication unit 94 and can transmit or receive various kinds of information to or from the console 42. The cassette control unit 92 stores exposure conditions, which will be described below, received from the console 42 through the wireless communication unit 94 and starts to read charge on the basis of the exposure conditions.

The electronic cassette 32 is also provided with a power supply unit 96 and the above-mentioned various kinds of circuits or elements (the gate line driver 80, the signal processing unit 82, the image memory 90, the wireless communication unit 94, or a microcomputer functioning as the cassette control unit 92) are operated by power supplied from the power supply unit 96. The power supply unit 96 includes a battery (chargeable secondary battery) so as not to impair the portability of the electronic cassette 32 and the charged battery supplies power to various kinds of circuits and elements. In FIG. 4, lines for connecting the power supply unit 96 and various kinds of circuits or elements are not shown.

The console 42 is configured as a server computer and includes a display 100 that displays, for example, an operation menu or a captured radiological image and an operation panel 102 that includes plural keys and receives various kinds of information or operation instructions.

The console 42 according to this embodiment further includes a CPU 104 that controls the overall operation of the console, a ROM 106 that stores in advance various kinds of programs including a control program, a RAM 108 that temporarily stores various kinds of data, an HDD 110 that stores various kinds of data, a display driver 112 that controls the display of various kinds of information on the display 100, and an operation input detecting unit 114 that detects an operation input to the operation panel 102.

The console 42 further includes a communication interface (I/F) unit 116 that is connected to the connection terminal 42A and transmits or receives various kinds of information, such as exposure conditions or positional information, which will be described below, to or from the radiation generating apparatus 34 through the connection terminal 42A and the communication cable 35 and a wireless communication unit 118 that wirelessly transmits or receives various kinds of information, such as exposure conditions or image data, to or from the electronic cassette 32.

The CPU 104, the ROM 106, the RAM 108, the HDD 110, the display driver 112, the operation input detecting unit 114, the communication I/F unit 116, and the wireless communication unit 118 are connected to each other by a system bus BUS. Therefore, the CPU 104 can access the ROM 106, the RAM 108, and the HDD 110. In addition, the CPU 104 can control the display of various kinds of information on the display 100 through the display driver 112, the transmission or reception of various kinds of information to or from the radiation generating apparatus 34 through the communication I/F unit 116, and the transmission or reception of various kinds of information to or from the electronic cassette 32 through the wireless communication unit 118. The CPU 104 can also check an operation input to the operation panel 102 by the user through the operation input detecting unit 114.

The radiation generating apparatus 34 includes a radiation source 130 that emits the radiation X, a movable diaphragm device 131 that limits a region irradiated with the radiation X from the radiation source 130, a communication I/F unit 132 that transmits or receives various types of information, such as exposure conditions, to or from the console 42, a radiation source control unit 134 that controls the radiation source 130 on the basis of the received exposure conditions, and a radiation source driving control unit 136 that controls the supply of power to each driving source provided in the supporting/moving mechanism 52 to control the operation of the supporting/moving mechanism 52.

The radiation source control unit 134 is also implemented by a microcomputer and stores the received exposure conditions or positional information. The exposure conditions received from the console 42 include information, such as a tube voltage, a tube current, and an irradiation period, and the positional information includes information indicating whether the imaging position is a standing position or a supine position. When the imaging position indicated by the received positional information is the standing position, the radiation source control unit 134 controls the supporting/moving mechanism 52 such that the radiation source driving control unit 136 controls the radiation source 130 to be disposed at a position 53A for standing position image capture (see FIG. 2; a position where radiation is emitted to the side of the patient disposed at the imaging position 48). When the imaging position indicated by the received positional information is the supine position, the radiation source control unit 134 controls the supporting/moving mechanism 52 such that the radiation source driving control unit 136 controls the radiation source 130 to be disposed at a position 53B for supine position image capture (see FIG. 2; a position where radiation is emitted to the patient disposed at the imaging position 50 from the upper side). In addition, when receiving an instruction to start exposure, the radiation source control unit 134 controls the radiation source 130 to emit the radiation X on the basis of the received exposure conditions. The radiation X is emitted from the radiation source 130 to the patient through the movable diaphragm device 131.

Figure 5:
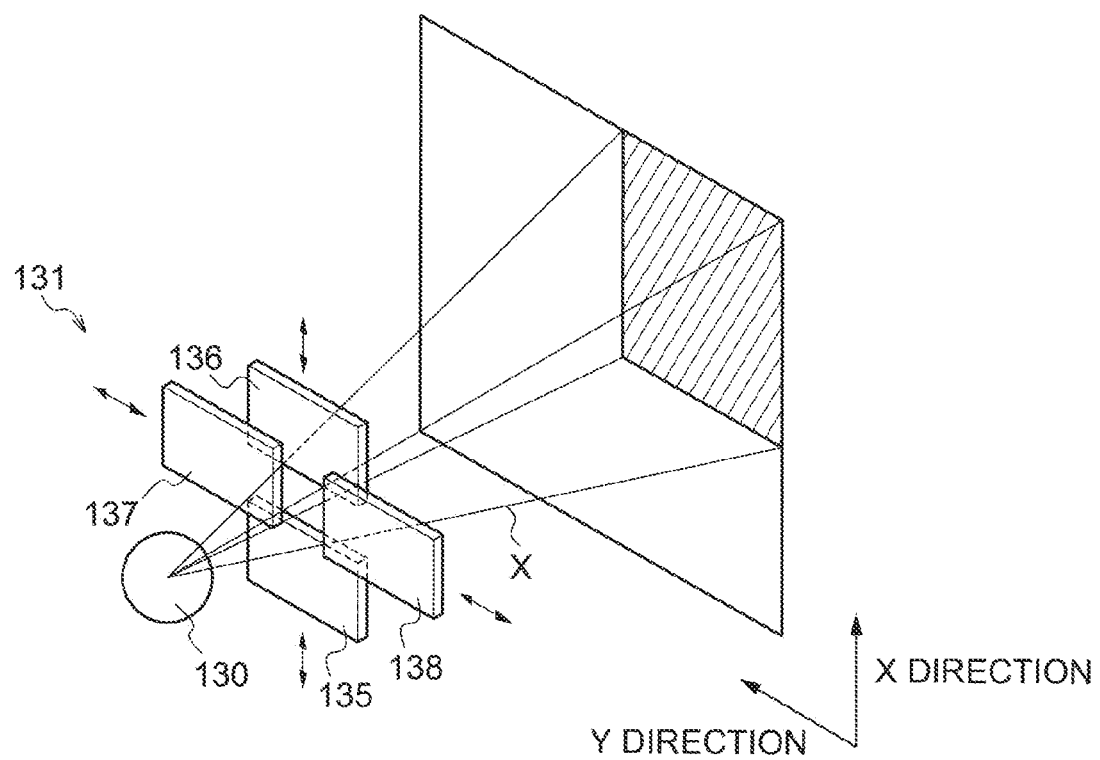
FIG. 5 is a perspective view schematically illustrating the structure of a movable diaphragm device according to the embodiment.

As shown in FIG. 5, the movable diaphragm device 131 includes slit plates 135 and 136 and slit plates 137 and 138. The slit plates 135 and 136 and the slit plates 137 and 138 can be moved by the driving force of a motor or a solenoid. In the movable diaphragm device 131, the slit plates 135 and 136 are individually moved in one direction (X direction) to change the region irradiated with the radiation X from the radiation source 130 in the X direction, and the slit plates 137 and 138 are individually moved in a direction (Y direction) intersecting the one direction to change the region irradiated with the radiation X from the radiation source 130 in the Y direction.

The movable diaphragm device 131 includes an operation panel 131A (see FIG. 4) that is used to instruct the movement of the slit plates 135 and 136 and the slit plates 137 and 138. The doctor or the radiographer operates the operation panel 131A to adjust the arrangement relationship between the slit plates 135 and 136 and the slit plates 137 and 138, thereby changing the region irradiated with the radiation X. For the region irradiated with the radiation X, for example, a camera may be provided in the vicinity of the radiation source 130 to capture the image of a target portion with radiation, and the captured image may be displayed on the display 100 of the console 42 such that the operator can check the captured image. In addition, a visible light lamp that emits visible light may be provided in the vicinity of the radiation source 130 and emit visible light to an imaging portion of the body of the examinee such that the operator can check the imaging portion.

Next, the structure of the indirect-conversion-type radiation detector 60 that indirectly converts radiation into charge using a phosphor material and a photoelectric conversion element will be described.

Figure 38:
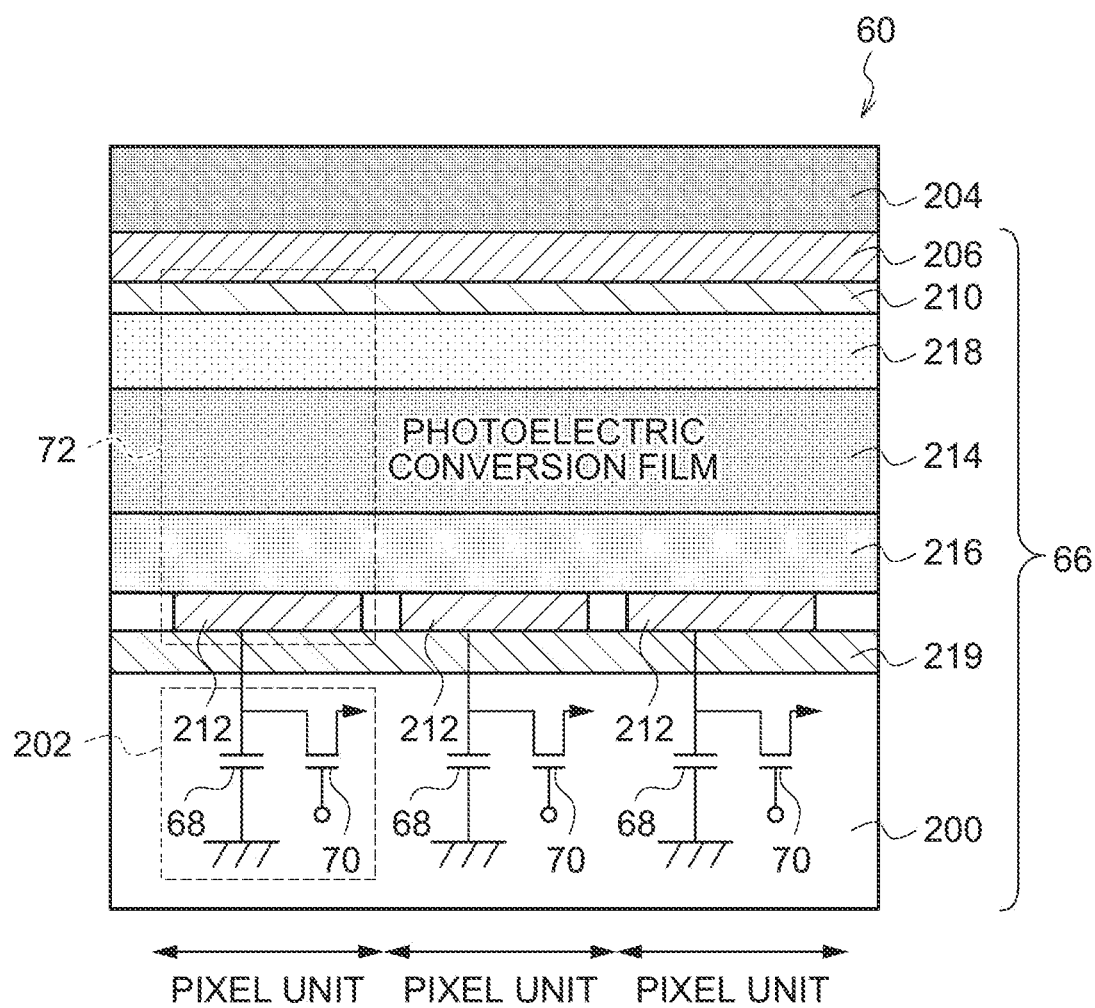
FIG. 38 is a graph illustrating the relationship between the amount of radiation emitted to a scintillator and the amount of light emitted.

FIG. 38 is a cross-sectional view schematically illustrating the structure of three pixel units of the indirect-conversion-type radiation detector 60 according to an embodiment of the invention.

The radiation detector 60 includes a signal output unit 202, a sensor unit 72, and a scintillator 204 that are sequentially laminated on an insulating substrate 200. The signal output unit 202 and the sensor unit 72 form a pixel unit. Plural pixel units are arranged on the substrate 200. In each pixel unit, the signal output unit 202 and the sensor unit 72 are arranged so as to overlap each other.

The scintillator 204 is formed on the sensor unit 72 with a transparent insulating film 206 interposed therebetween, and has a phosphor film that converts radiation incident from the upper side (the side opposite to the substrate 200) into light and emits the light. The provision of the scintillator 204 makes it possible to absorb radiation passing through the object and emit light.

It is preferable that the wavelength range of light emitted by the scintillator 204 be a visible light range (wavelength of 360 nm to 830 nm). It is more preferable that the wavelength range of light include a green wavelength range in order to capture a monochromatic image using the radiation detector 60.

Specifically, in a case in which imaging is performed using X-rays as radiation, it is preferable that the phosphor used for the scintillator 204 include cesium iodide (CsI). It is more preferable to use CsI(T1) having an emission spectrum of 420 nm to 600 nm during the emission of X-rays. The emission peak wavelength of CsI(T1) in the visible light range is 565 nm.

In a case in which the scintillator 204 is made of a columnar crystal, such as CsI(T1), it may be formed on a vapor deposition substrate by vapor deposition. As such, in a case in which the scintillator 204 is formed by vapor deposition, an Al plate is generally used as the vapor deposition substrate in terms of the transmittance of X-rays and manufacturing costs, but the vapor deposition substrate is not limited to the Al plate. In a case in which GOS is used as the scintillator 204, GOS may be applied onto the surface of a TFT active matrix substrate 66 to form the scintillator 204, without using the vapor deposition substrate.

The sensor unit 72 includes an upper electrode 210, a lower electrode 212, and a photoelectric conversion film 214 provided between the upper and lower electrodes.

The upper electrode 210 needs to make light generated by the scintillator 204 incident on the photoelectric conversion film 214. Therefore, it is preferable that the upper electrode 210 be made of a conductive material that is at least transparent with respect to the emission wavelength of the scintillator 204. Specifically, it is preferable that the upper electrode 210 be made of a transparent conducting oxide (TCO) having high transmittance with respect to visible light and a small resistance value. A metal thin film, such as an Au thin film, may be used as the upper electrode 210. However, when the transmittance increases to 90% or more, the resistance value is likely to increase. Therefore, it is preferable that the upper electrode 210 be made of TCO. For example, it is preferable that the upper electrode 210 be made of ITO, IZO, AZO, FTO, $SnO_2$, $TiO_2$, or $ZnO_2$. It is most preferable that the upper electrode 210 be made of ITO in terms of a simple process, low resistance, and transparency. One upper electrode 210 may be common to all pixel units, or the upper electrode 210 may be divided for each pixel unit.

The photoelectric conversion film 214 absorbs light emitted from the scintillator 204 and generates a charge corresponding to the absorbed light. The photoelectric conversion film 214 may be made of a material that receives light and generates charge. For example, the photoelectric conversion film 214 may be made of amorphous silicon or an organic photoelectric conversion material. When the photoelectric conversion film 214 includes amorphous silicon, it has a wide absorption spectrum and can absorb light emitted from the scintillator 204. When the photoelectric conversion film 214 includes an organic photoelectric conversion material, it has a narrow absorption spectrum in the visible light range and absorbs little electromagnetic waves other than the light emitted from the scintillator 204. Therefore, it is possible to effectively reduce noise generated due to the absorption of radiation, such as X-rays, by the photoelectric conversion film 214.

It is preferable that the absorption peak wavelength of the organic photoelectric conversion material forming the photoelectric conversion film 214 be close to the emission peak wavelength of the scintillator 204 in order to most effectively absorb light emitted from the scintillator 204. It is ideal that the absorption peak wavelength of the organic photoelectric conversion material is equal to the emission peak wavelength of the scintillator 204. However, when the difference between the absorption peak wavelength and the emission peak wavelength is small, it is possible to sufficiently absorb light emitted from the scintillator 204. Specifically, the difference between the absorption peak wavelength of the organic photoelectric conversion material and the emission peak wavelength of the scintillator 204 with respect to radiation is preferably equal to or less than 10 nm and more preferably, equal to or less than 5 nm.

Examples of the organic photoelectric conversion material capable of satisfying the above-mentioned conditions include a quinacridone-based organic compound and a phthalocyanine-based organic compound. For example, the absorption peak wavelength of quinacridone in the visible light range is 560 nm. Therefore, when quinacridone is used as the organic photoelectric conversion material and CsI(T1) is used as the material forming the scintillator 204, it is possible to reduce the difference between the peak wavelengths to 5 nm or less and substantially maximize the amount of charge generated by the photoelectric conversion film 214.

Next, the photoelectric conversion film 214 that can be applied to the radiation detector 60 according to this embodiment will be described in detail.

An electromagnetic wave absorption/photoelectric conversion portion of the radiation detector 60 according to the invention may be formed by an organic layer including a pair of the lower electrode 212 and the upper electrode 210 and the organic photoelectric conversion film 214 interposed between the lower electrode 212 and the upper electrode 210. Specifically, the organic layer may be formed by laminating or mixing, for example, an electromagnetic wave absorption portion, a photoelectric conversion portion, an electron transport portion, a hole transport portion, an electron blocking portion, a hole blocking portion, a crystallization prevention portion, an electrode, and an interlayer contact improvement portion.

It is preferable that the organic layer include an organic p-type compound or an organic n-type compound.

The organic p-type semiconductor (compound) is a donor-type organic semiconductor (compound) whose representative example is a hole-transport-type organic compound and means an organic compound which readily donates electrons. Specifically, in a case in which two organic materials are in contact with each other during use, one organic compound with low ionization potential is the organic p-type semiconductor. Therefore, any organic compound may be used as the donor-type organic compound as long as it has an electron donating property.

The organic n-type semiconductor (compound) is an acceptor-type organic semiconductor (compound) whose representative example is an electron-transport-type organic compound and means an organic compound which readily accepts electrons. Specifically, in a case in which two organic compounds are in contact with each other during use, one organic compound with high electron affinity is the organic n-type semiconductor. Therefore, any organic compound may be used as the acceptor-type organic compound as long as it has an electron accepting property.

Materials applicable to the organic p-type semiconductor and the organic n-type semiconductor and the structure of the photoelectric conversion film 214 have been described in detail in JP-A No. 2009-32854 and thus a detailed description thereof will be omitted. The photoelectric conversion film 214 may include fullerene or carbon nanotubes.

It is preferable that the thickness of the photoelectric conversion film 214 be as large as possible in terms of the absorption of light from the scintillator 204. However, when the thickness of the photoelectric conversion film 214 is greater than a predetermined value, the intensity of the electric field of the photoelectric conversion film 214 generated by the bias voltage applied from both ends of the photoelectric conversion film 214 is reduced, which makes it difficult to collect charge. Therefore, the thickness of the photoelectric conversion film 214 is preferably from 30 nm to 300 nm, more preferably from 50 nm to 250 nm, and most preferably from 80 nm to 200 nm.

In the radiation detector 60 shown in FIG. 38, one photoelectric conversion film 214 is common to all pixel units. However, the photoelectric conversion film 214 may be divided for each pixel unit.

The lower electrode 212 is a thin film that is divided for each pixel unit. The lower electrode 212 may be appropriately made of a transparent or opaque conductive material, such as aluminum or silver.

The thickness of the lower electrode 212 may be, for example, from 30 nm to 300 nm.

In the sensor unit 72, a predetermined bias voltage can be applied between the upper electrode 210 and the lower electrode 212 to move one of the charges (a hole and an electron) generated from the photoelectric conversion film 214 to the upper electrode 210 and move the other charge to the lower electrode 212. In the radiation detector 60 according to this embodiment, a wiring line is connected to the upper electrode 210 and the bias voltage is applied to the upper electrode 210 through the wiring line. It is assumed that the polarity of the bias voltage is determined such that the electron generated in the photoelectric conversion film 214 is moved to the upper electrode 210 and the hole is moved to the lower electrode 212. However, the polarity may be reversed.

The sensor unit 72 forming each pixel unit may include at least the lower electrode 212, the photoelectric conversion film 214, and the upper electrode 210. In order to prevent an increase in dark current, it is preferable that at least one of the electron blocking film 216 and the hole blocking film 218 be provided, and it is more preferable that both the electron blocking film 216 and the hole blocking film 218 be provided.

The electron blocking film 216 may be provided between the lower electrode 212 and the photoelectric conversion film 214. In a case in which the bias voltage is applied between the lower electrode 212 and the upper electrode 210, it is possible to prevent an increase in the dark current due to the injection of electrons from the lower electrode 212 into the photoelectric conversion film 214.

The electron blocking film 216 may be made of an electron donating organic material.

In practice, the material used for the electron blocking film 216 may be selected according to a material forming an adjacent electrode and a material forming an adjacent photoelectric conversion film 214. It is preferable that the material used for the electron blocking film 216 have an electron affinity (Ea) that is at least 1.3 eV higher than the work function (Wf) of the material forming the adjacent electrode and have an ionization potential (Ip) equal to or less than that of the material forming the adjacent photoelectric conversion film 214. Materials applicable as the electron donating organic material have been described in detail in JP-A No. 2009-32854 and thus a detailed description thereof will be omitted.

The thickness of the electron blocking film 216 is preferably from 10 nm to 200 nm, more preferably from 30 nm to 150 nm, and most preferably from 50 nm to 100 nm in order to reliably obtain the effect of preventing the dark current and prevent a reduction in the photoelectric conversion efficiency of the sensor unit 72.

The hole blocking film 218 may be provided between the photoelectric conversion film 214 and the upper electrode 210. In a case in which the bias voltage is applied between the lower electrode 212 and the upper electrode 210, it is possible to prevent an increase in the dark current due to the injection of holes from the upper electrode 210 into the photoelectric conversion film 214.

The hole blocking film 218 may be made of an electron accepting organic material.

The thickness of the hole blocking film 218 is preferably from 10 nm to 200 nm, more preferably from 30 nm to 150 nm, and most preferably from 50 nm to 100 nm in order to reliably obtain the effect of preventing the dark current and prevent a reduction in the photoelectric conversion efficiency of the sensor unit 72.

In practice, the material used for the hole blocking film 218 may be selected according to a material forming an adjacent electrode and a material forming an adjacent photoelectric conversion film 214. It is preferable that the material used for the hole blocking film 218 have an ionization potential (Ip) that is at least 1.3 eV higher than the work function (Wf) of the material forming the adjacent electrode and have an electron affinity (Ea) equal to or more than that of the material forming the adjacent photoelectric conversion film 214. Materials applicable as the electron accepting organic material have been described in detail in JP-A No. 2009-32854 and thus a detailed description thereof will be omitted.

In a case in which the bias voltage is set such that, among the charges generated in the photoelectric conversion film 214, holes are moved to the upper electrode 210 and electrons are moved to the lower electrode 212, the positions of the electron blocking film 216 and the hole blocking film 218 may be reversed. In addition, neither the electron blocking film 216 nor the hole blocking film 218 may be provided. When either the electron blocking film 216 or the hole blocking film 218 is provided, it is possible to a certain extent to obtain the effect of preventing the dark current.

The signal output unit 202 is provided on the surface of the substrate 200 below the lower electrode 212 of each pixel unit.

Figure 39:
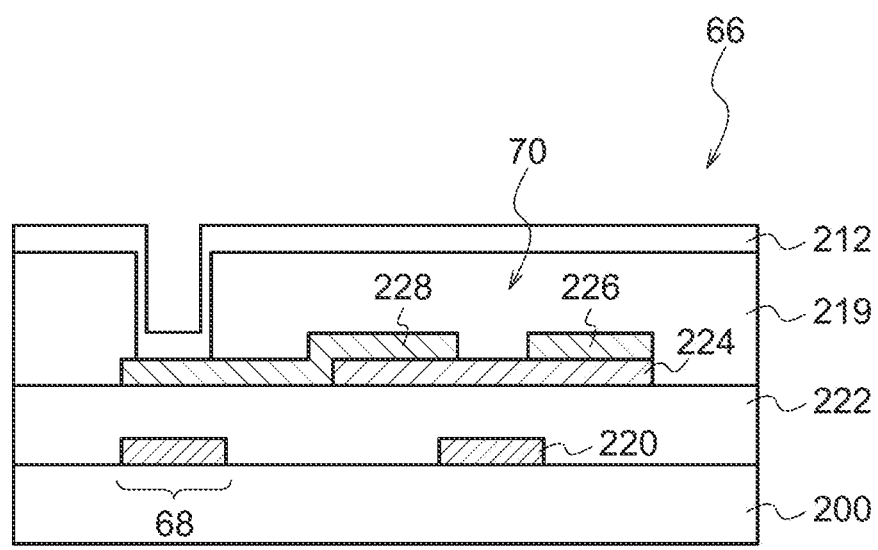
FIG. 39 is a graph illustrating a change in the variation Δ of the gradient of the sensitivity line of the scintillator over time.

FIG. 39 is a diagram schematically illustrating the structure of the signal output unit 202.

A storage capacitor 68 that stores the charge moved to the lower electrode 212 and a TFT 70 that converts the charge stored in the storage capacitor 68 into an electric signal and outputs the electric signal are formed so as to correspond to the lower electrode 212. A region in which the storage capacitor 68 and the TFT 70 are formed has a portion that overlaps the lower electrode 212 in a plan view. In this way, the signal output unit 202 and the sensor unit 72 in each pixel unit overlap each other in the thickness direction. In order to minimize the plane area of the radiation detector 60 (pixel unit), it is preferable that the region in which the storage capacitor 68 and the TFT 70 are formed be completely covered with the lower electrode 212.

The storage capacitor 68 is electrically connected to the lower electrode 212 through a conductive line that is formed so as to pass through the insulating film 219 provided between the substrate 200 and the lower electrode 212. In this way, it is possible to move the charge captured by the lower electrode 212 to the storage capacitor 68.

The TFT 70 is formed by laminating a gate electrode 220, a gate insulating film 222, and an active layer (channel layer) 224 and providing a source electrode 226 and a drain electrode 228 on the active layer 224 with a predetermined gap therebetween. The active layer 224 may be made of, for example, amorphous silicon, an amorphous oxide, an organic semiconductor material, or carbon nanotubes. The material forming the active layer 224 is not limited thereto.

An oxide (for example, an In—O-based oxide) including at least one of In, Ga, and Zn is preferable as the amorphous oxide that can form the active layer 224. An oxide (for example, an In—Zn—O-based oxide, an In—Ga—O-based oxide, or a Ga—Zn—O-based oxide) including at least two of In, Ga, and Zn is more preferable as the amorphous oxide. An oxide including In, Ga, and Zn is most preferable as the amorphous oxide. As an In—Ga—Zn—O-based amorphous oxide, an amorphous oxide having a composition represented by $InGaO_3(ZnO)_m$ (m is a natural number smaller than 6) in a crystalline state is preferable, and $InGaZnO_4$ is more preferable. The amorphous oxide that can form the active layer 224 is not limited thereto.

A phthalocyanine compound, pentacene, or vanadyl phthalocyanine may be given as an example of the organic semiconductor material that can form the active layer 224, but the organic semiconductor material is not limited thereto. The structure of the phthalocyanine compound has been described in detail in JP-A No. 2009-212389 and thus a detailed description thereof will be omitted.

When the active layer 224 of the TFT 70 is made of an amorphous oxide, an organic semiconductor material, or carbon nanotubes, radiation, such as X-rays, is not absorbed. Even though the radiation is absorbed, a very small amount of radiation remains. Therefore, it is possible to effectively prevent the generation of noise in the signal output unit 202.

In a case in which the active layer 224 is made of carbon nanotubes, it is possible to improve the switching speed of the TFT 70 and form the TFT 70 with low light absorptance in the visible light range. In addition, in a case in which the active layer 224 is made of carbon nanotubes, even though a very small amount of metallic impurities is mixed with the active layer 224, the performance of the TFT 70 is significantly reduced. Therefore, it is necessary to separate and extract carbon nanotubes with very high purity using, for example, centrifugal separation and form the active layer with the carbon nanotube.

All of the amorphous oxide, the organic semiconductor material, the carbon nanotubes, and the organic photoelectric conversion material can be used to form a film at a low temperature. The substrate 200 is not limited to a substrate with high heat resistance, such as a semiconductor substrate, a quartz substrate, or a glass substrate, but a flexible substrate, such as a plastic substrate, an aramid substrate, or a bio-nanofiber substrate may be used as the substrate 200. Specifically, for example, a flexible substrate made of the following materials may be used: polyester, such as polyethylene terephthalate, polybutylene phthalate, or polyethylene naphthalate, polystyrene, polycarbonate, polyether sulfone, polyarylate, polyimide, polycycloolefin, norbornene resin, and poly(chlorotrifluoroethylene). When the flexible substrate made of plastic is used, it is possible to reduce the weight of the substrate. For example, this structure has an advantage in portability.

In addition, for example, an insulating layer for ensuring an insulating property, a gas barrier layer for preventing the penetration of water or oxygen, and an undercoating layer for improving flatness or the adhesion of, for example, the electrode may be provided on the substrate 200.

Since aramid can be applied to a high-temperature process of 200 degrees or more, a transparent electrode material can be cured at a high temperature to have low resistance, and the aramid can respond to the automatic mounting of a driver IC including a solder reflow process. In addition, the thermal expansion coefficient of aramid is close to that of ITO (indium tin oxide) or a glass substrate. Therefore, after an aramid substrate is manufactured, the warping of the aramid substrate is small and the aramid substrate is less likely to be cracked. In addition, aramid is capable of forming a substrate thinner than, for example, a glass substrate. Aramid may be laminated on a super-thin glass substrate to form the substrate 200.

The bio-nanofiber is a composite of a cellulose microfibril bundle generated by bacteria (Acetobacter Xylinum) (bacterial cellulose) and a transparent resin. The cellulose microfibril bundle has a width of 50 nm, a size of one-tenth of the visible light wavelength, high strength, high elasticity, and a low thermal expansion coefficient. A transparent resin, such as an acrylic resin or an epoxy resin, is impregnated into the bacterial cellulose and is then cured to obtain bio-nanofiber that has a light transmittance of about 90% at a wavelength of 500 nm while including 60 to 70% of fiber. The bio-nanofiber has a low thermal expansion coefficient (3 to 7 ppm) equal to that of a silicon crystal, strength (460 MPa) similar to that of iron, high elasticity (30 GPa), and flexibility. Therefore, the bio-nanofiber is capable of forming a substrate 200 thinner than, for example, a glass substrate.

In this embodiment, the signal output unit 202, the sensor unit 72, and the transparent insulating film 206 are sequentially formed on the substrate 200 and the scintillator 204 is bonded to the substrate 200 by an adhesive resin with low light absorptance, thereby forming the radiation detector 60. Hereinafter, the substrate 200 including up to the transparent insulating film 206 formed thereon is referred to as the TFT active matrix substrate (hereinafter, referred to as a "TFT substrate") 66.

Next, the overall operation of the RIS 10 according to this embodiment will be described briefly.

When a radiological image is captured, the terminal apparatus 12 (see FIG. 1) receives an imaging request from the doctor or the radiographer. The usage environment of the electronic cassette 32, the date of imaging, an imaging portion, which is an imaging target, a tube voltage, an imaging position, and a dose of radiation are designated by the imaging request.

The terminal apparatus 12 notifies the RIS server 14 of the content of the received imaging request. The RIS server 14 stores the content of the imaging request notified by the terminal apparatus 12 in the database 14A.

The console 42 accesses the RIS server 14 to acquire the content of the imaging request from the RIS server 14, and displays the content of the imaging request on the display 100 (see FIG. 4).

In addition, the console 42 transmits positional information indicating an imaging position for radiography that now is performed to the radiation generating apparatus 34. Then, the radiation source control unit 134 of the radiation generating apparatus 34 controls the radiation source driving control unit 136 such that the radiation source 130 is disposed at a position corresponding to the imaging position designated by the received positional information.

The doctor or the radiographer starts to capture a radiological image on the basis of the content of the imaging request displayed on the display 100.

For example, when the radiological image of a patient 50 who lies down on the bed 46 shown in FIG. 2 is captured, the doctor or the radiographer arranges the electronic cassette 32 between the bed 46 and an imaging portion of the patient 50 according to the imaging portion of the patient 50. Then, the doctor or the radiographer arranges the radiation generating apparatus 34 above the imaging portion, and operates the operation panel 131A of the movable diaphragm device 131 to limit the region irradiated with the radiation X such that the radiation X is emitted only to the imaging portion and the periphery thereof. In addition, the doctor or the radiographer uses the operation panel 102 of the console 42 to designate the exposure conditions, such as a tube voltage, a tube current, and an irradiation period when the radiation X is emitted, according to the imaging portion of the patient or imaging conditions.

However, when radiography is repeatedly performed using a specific portion of a detection region 61 of the radiation detector 60 capable of detecting radiation, only the portion of the detection region deteriorates.

Figure 6:
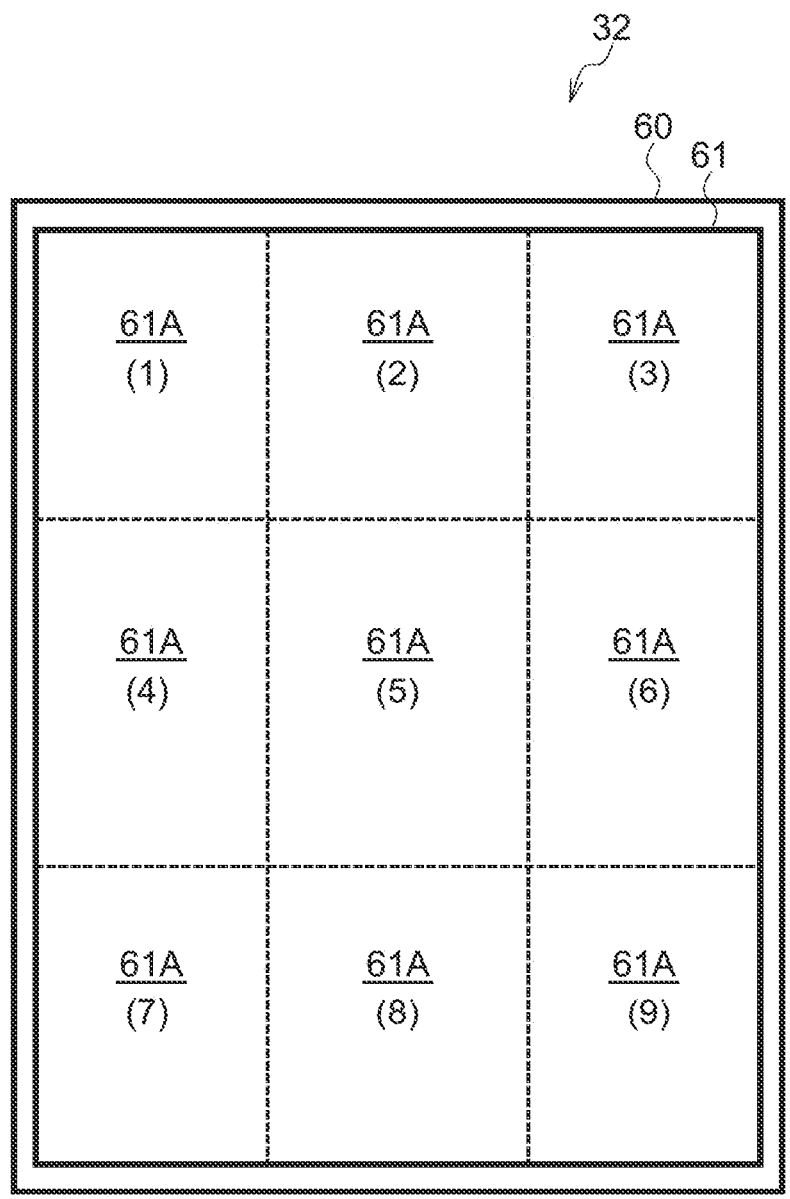
FIG. 6 is a plan view illustrating an example of the division of a detection region of a radiation detector according to the embodiment into nine areas.

Therefore, in this embodiment, as shown in FIG. 6, the detection region 61 of the radiation detector 60 is divided into 3×3 (=9) divided areas 61A, and a correlation value correlated with the amount of radiation emitted to each of the divided areas 61A is stored as correlation information in the HDD 110. In each of the divided areas 61A, a number in parentheses (for example, (1)) indicates an identification number for identifying each divided area 61A.

Figure 7:
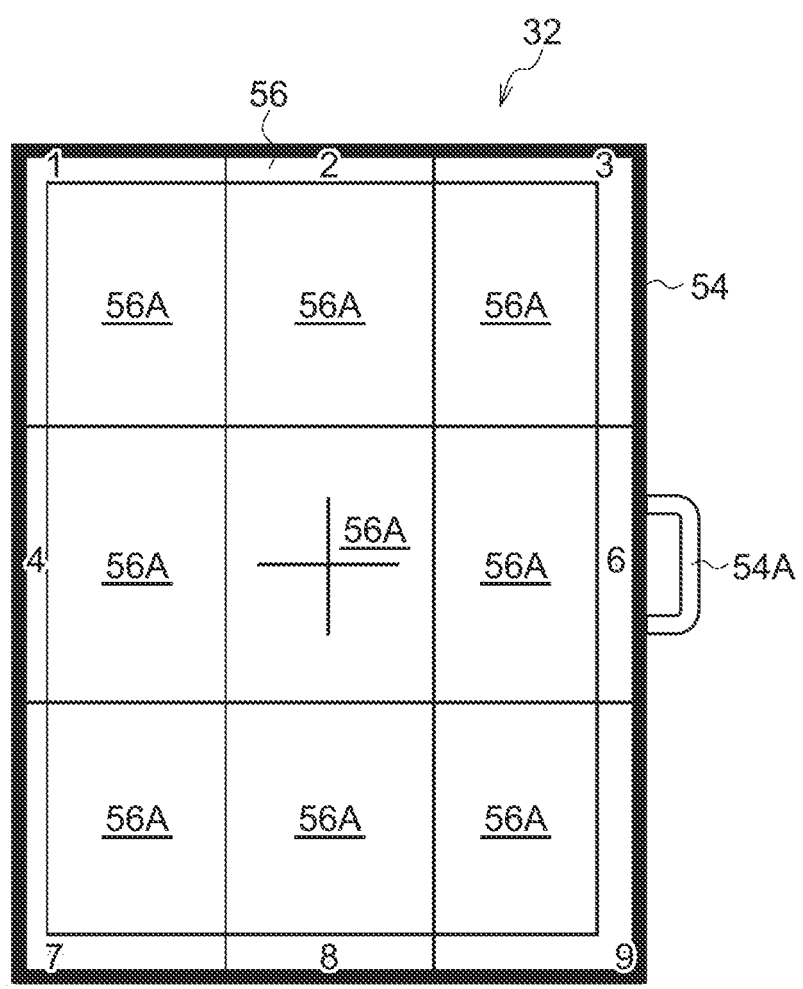
FIG. 7 is a plan view illustrating an example of an irradiation surface of an electronic cassette according to the first embodiment.

As shown in FIG. 7, an irradiation surface 56 of the housing 54 of the electronic cassette 32 to which the radiation X is emitted is divided into areas 56A corresponding to the divided areas 61A of the radiation detector 60, and identification numbers corresponding to the divided areas 61A of the radiation detector 60 are given to the peripheral portions of the areas 56A other than a central area 56A.

FIG. 8 shows an example of the data structure of the correlation information stored in the HDD 110.

In this embodiment, the number of imaging operations using the divided areas 61A is stored as the correlation value for each of the identification numbers of the divided areas 61A.

In this embodiment, for each imaging portion of the patient whose radiological image is captured, size information indicating the size of the area required to capture the radiological image of the imaging portion is stored in the HDD 110.

FIG. 9 shows an example of the data structure of the size information stored in the HDD 110.

In this embodiment, the number of divided areas 61A in the vertical direction and the horizontal direction is stored as size information required to capture the radiological image of each imaging portion. For example, when the image of the hand, which is an imaging portion, is captured, a total of four (2×2 (two in the vertical direction and two in the horizontal direction)) divided areas 61A are needed.

In this embodiment, divided area combination information indicating combinations of the divided areas 61A by which each size of the area required for imaging is obtained in the detection region 61 is stored in the HDD 110.

FIG. 10 shows an example of the data structure of the divided area combination information stored in the HDD 110.

In this embodiment, combinations of the identification numbers of the divided areas 61A by which each size of the area required for imaging is obtained are stored. For example, when the size of the area required for imaging is 2×2, four combinations of the identification numbers of the divided areas 61A, that is, (1, 2, 4, 5), (2, 3, 5, 6), (4, 5, 7, 8), and (5, 6, 8, 9) are stored.

When a predetermined operation instruction to prepare for imaging is input to the operation panel 102, the console 42 performs an imaging area specifying process of specifying an imaging area capable of capturing the radiological image of an imaging portion while preventing variations in the amount of radiation emitted to each of the divided areas 61A of the radiation detector 60.

Figure 11:
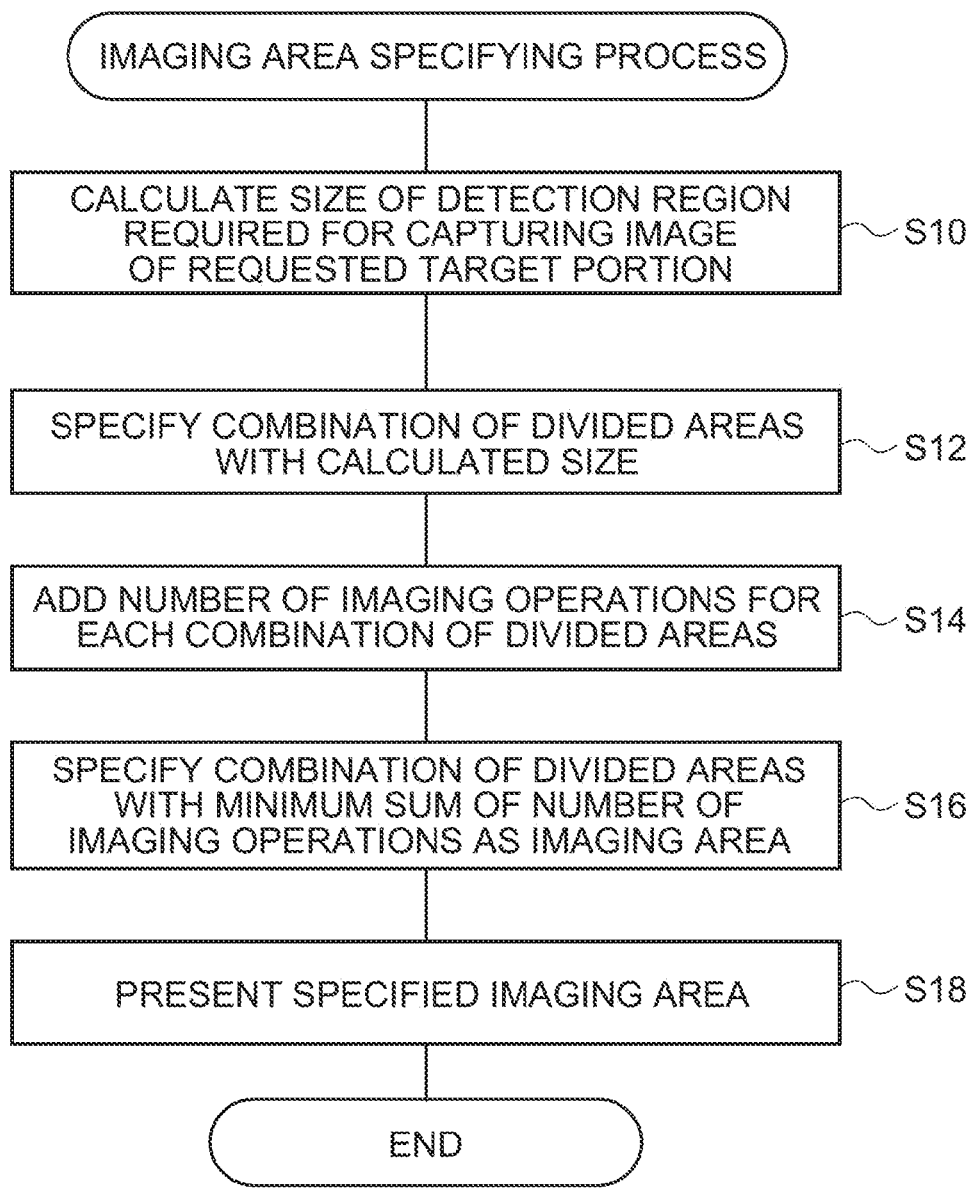
FIG. 11 is a flowchart illustrating the flow of a process of an imaging area specifying program according to the embodiment.

FIG. 11 is a flowchart illustrating the flow of a process of an imaging area specifying program executed by the CPU 104 according to this embodiment. The program is stored in a predetermined area of the HDD 110 in advance.

In Step S10 of FIG. 11, the size of the divided area 61A corresponding to a target portion that is requested to be captured by the imaging request is read from the size information stored in the HDD 110.

In Step S12, a combination of the divided areas 61A by which the size read in Step S12 is obtained is specified on the basis of the divided area combination information stored in the HDD 110.

In Step S14, the number of imaging operations in each divided area 61A which is indicated by the correlation information stored in the HDD 110 is summed for each combination of the divided areas 61A specified in Step S14.

In Step S16, a combination of the divided areas 61A with the minimum sum of the number of imaging operations calculated in Step S14 is specified as an imaging area.

In Step S18, the divided area 61A specified as the imaging area in Step S16 is displayed on the display 100, and the process ends.

Figure 12:
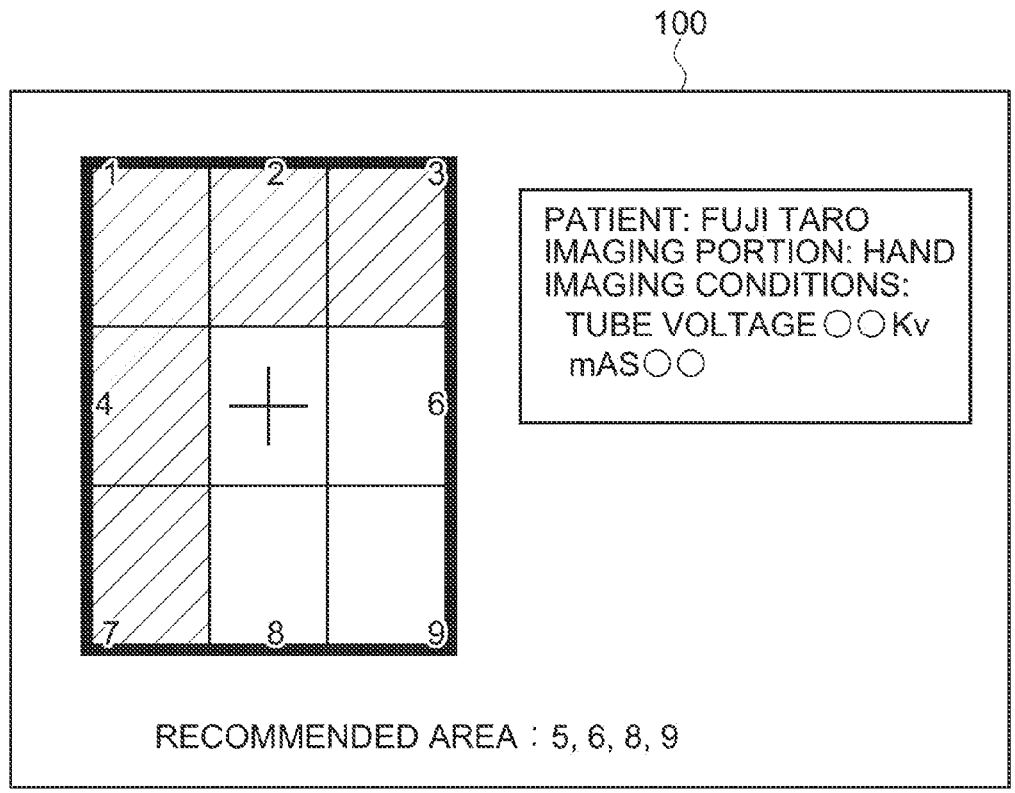
FIG. 12 is a diagram illustrating an example of the display of an imaging area according to the embodiment on a display.

FIG. 12 shows an example of the display aspect of the display 100. FIG. 12 shows the name of the patient whose image is captured, an imaging portion, and imaging conditions, in addition to the divided area 61A specified as the imaging area.

In this embodiment, among all of the divided areas 61A, the divided area 61A specified as the imaging area is displayed in white and the identification number of the divided area 61A specified as the imaging area is displayed as a recommended area.

The doctor or the radiographer arranges the electronic cassette 32 such that the area 56A with the identification number displayed on the display 100 corresponds to the imaging portion. When preparation for imaging is completed, the doctor or the radiographer operates the operation panel 102 of the console 42 to input an imaging instruction.

When the imaging instruction is input through the operation panel 102, the console 42 transmits instruction information to start exposure to the radiation generating apparatus 34 and the electronic cassette 32. Then, the radiation source 130 generates and emits radiation at a tube voltage and a tube current and for an irradiation period corresponding to the exposure conditions received by the radiation generating apparatus 34 from the console 42.

In this way, radiation is emitted to the divided area 61A of the radiation detector 60 specified as the imaging area and the radiological image is captured. Therefore, it is possible to prevent only a specific portion of the detection region 61 from deteriorating.

After the irradiation period designated in the exposure conditions has elapsed from the reception of the instruction information to start exposure, the cassette control unit 92 of the electronic cassette 32 controls the gate line driver 80 to sequentially output an on signal to each gate line 76, thereby sequentially turning on each line of the TFTs 70 connected to each gate line 76.

In the radiation detector 60, when each line of the TFTs 70 connected to each gate line 76 is sequentially turned on, charge stored in each line of the storage capacitors 68 flows as an electric signal to each data line 78. The electric signal flowing to each data line 78 is converted into digital image data by the signal processing unit 82 and is then stored in the image memory 90.

After the imaging operation ends, the cassette control unit 92 transmits the image information stored in the image memory 90 to the console 42 by wireless communication.

The console 42 performs various kinds of correction processes, such as shading correction, on the received image information and performs image processing for trimming the image of a portion corresponding to the divided area 61A specified as the imaging area. Then, the console 42 stores the image information subjected to image processing in the HDD 110. The image information stored in the HDD 110 is displayed on the display 100 such that the captured radiological image can be checked. In addition, the image information is transmitted to the server computer forming the RIS (Radiology Information System) through the network and is then stored in the database. In this way, the doctor can interpret the captured radiological image or make a diagnosis.

After the image information subjected to image processing is stored in the HDD 110, the console 42 performs a correlation information update process of updating the correlation information stored in the HDD 110.

Figure 13:
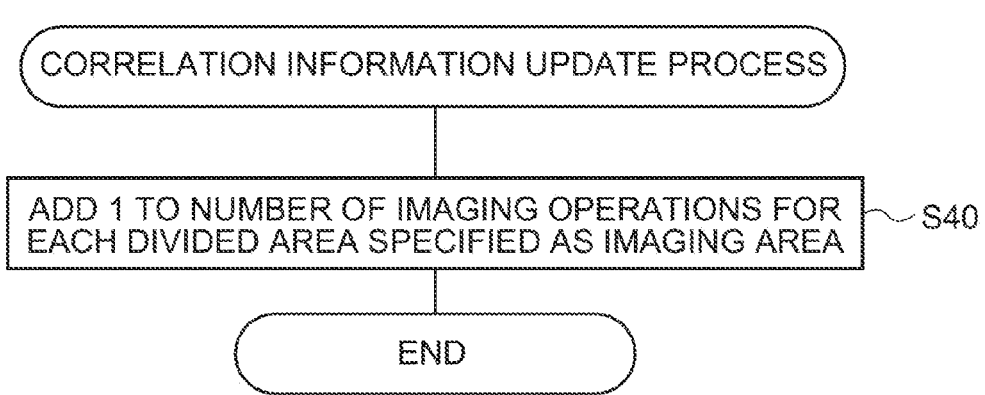
FIG. 13 is a flowchart illustrating the flow of a process of a correlation information update program according to the embodiment.

FIG. 13 is a flowchart illustrating the flow of a process of a correlation information update program executed by the CPU 104 according to this embodiment. The program is stored in a predetermined area of the HDD 110 in advance.

In Step S40 of FIG. 13, in the number of imaging operations in each divided area 61A indicated by the correlation information stored in the HDD 110, 1 is added to the number of imaging operations in the divided area 61A specified as the imaging area by the process of the imaging area specifying program, and the process ends.

In this way, the number of imaging operations in each divided area 61A which is stored as the correlation information is updated.

As described above, according to this embodiment, the detection region 61 of the radiation detector 60 is divided into plural predetermined areas, and the correlation value correlated with the amount of radiation emitted to each of the plural divided areas 61A is stored as the correlation information. In addition, the imaging area capable of capturing a radiological image of a predetermined size is specified on the basis of the stored correlation information while variations in the amount of radiation emitted to each of the divided areas 61A of the detection region 61 is prevented, and the specified imaging area is used to capture the radiological image. Therefore, it is possible to prevent the deterioration of a specific portion of the detection region 61.

According to this embodiment, since the specified imaging area is displayed on the display 100, it is possible to introduce the imaging area without changing the electronic cassette 32.

[Second Embodiment]

Next, a second embodiment will be described.

The structure of a radiology information system 10 according to the second embodiment is the same as that according to the first embodiment (see FIGS. 1 and 2) and thus a description thereof will be omitted.

Figure 14:
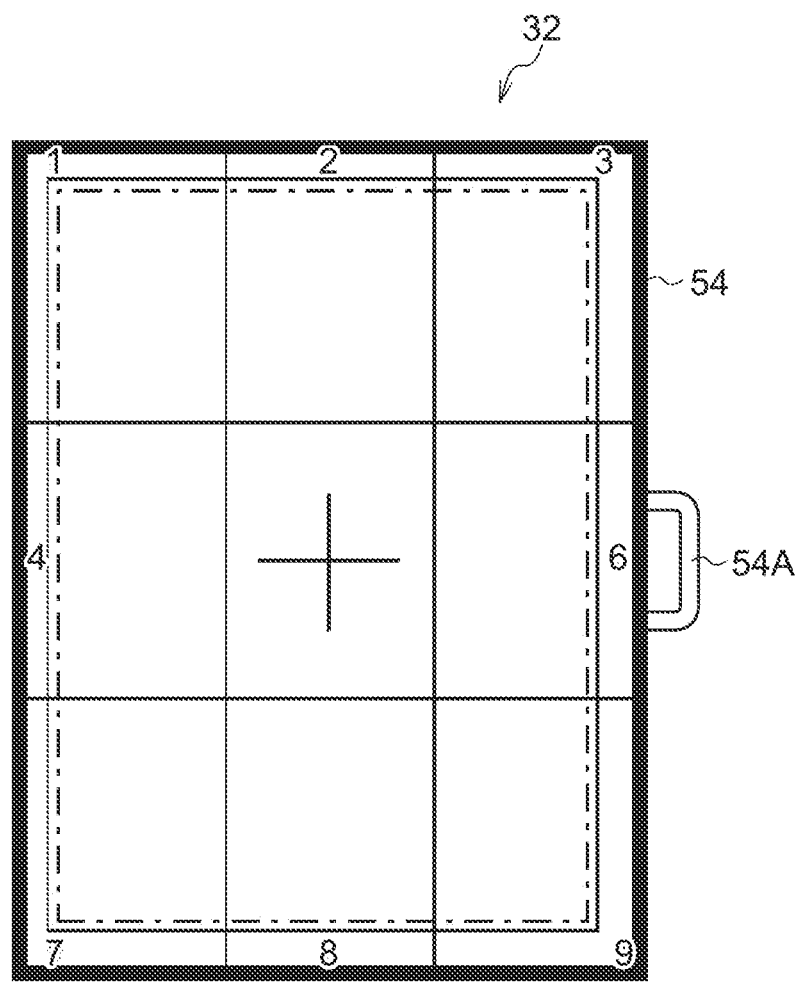
FIG. 14 is a plan view illustrating an example of an irradiation surface of an electronic cassette according to a second embodiment.

FIG. 14 shows the structure of an electronic cassette 32 according to the second embodiment. The same components as those in the first embodiment (see FIG. 7) are denoted by the same reference numerals and a description thereof will be omitted.

The electronic cassette 32 according to the second embodiment includes a touch panel 57 that is provided integrally with an irradiation surface 56. The touch panel 57 may be any of a pressure-sensitive type, a resistance film type, a capacitance type, an optical scanning type, and an ultrasonic type. In this embodiment, one touch panel 57 is provided for the irradiation surface 56. However, the touch panel 57 may be provided for each area 56A.

Figure 15:
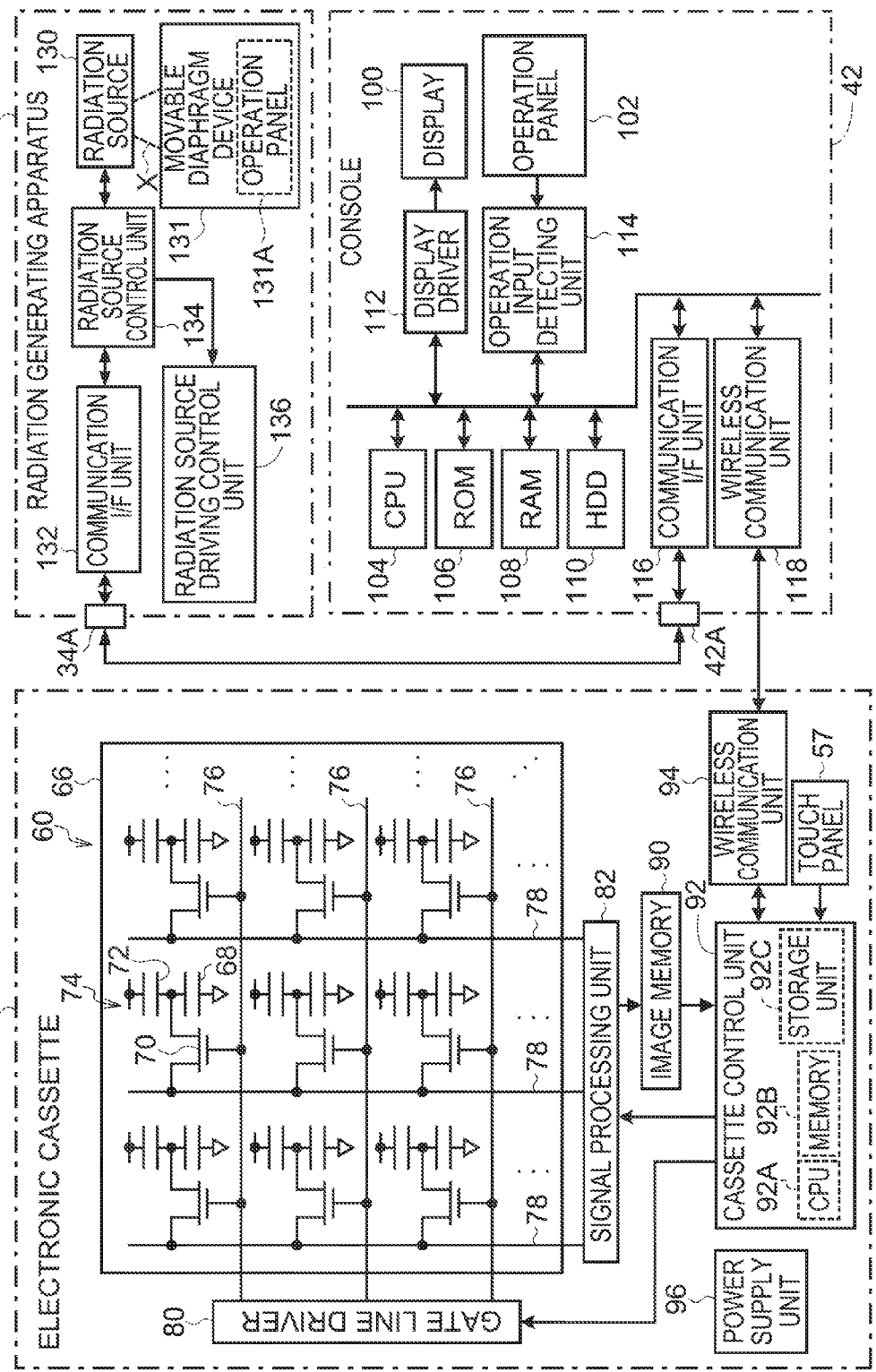
FIG. 15 is a block diagram illustrating the detailed structure of a radiographic system according to the second embodiment.

FIG. 15 is a block diagram illustrating the detailed structure of a radiographic system 18 according to the second embodiment. The same components as those in the first embodiment (FIG. 4) are denoted by the same reference numerals and a description thereof will be omitted.

The touch panel 57 is connected to a cassette control unit 92. The cassette control unit 92 can check which one of the areas 56A of the irradiation surface 56 contacts an object on the basis of the detection result of the touch panel 57.

The console 42 transmits the identification number of the divided area 61A specified as the imaging area by the imaging area specifying process to the electronic cassette 32 by wireless communication. The console 42 displays the divided area 61A specified as the imaging area and a message for prompting the operator to arrange an imaging portion in the imaging area on the display 100. The console 42 waits for imaging until an exposure permission notice for permitting the emission of radiation, which will be described below, is received from the electronic cassette 32. Even when an imaging instruction operation is input through the operation panel 102, the console 42 invalidates the imaging instruction operation and does not transmit instruction information to start exposure to the radiation generating apparatus 34 and the electronic cassette 32.

The doctor or the radiographer arranges the electronic cassette 32 such that the divided area 61A displayed on the display 100 corresponds to an imaging portion.

When receiving the identification number of the divided area 61A specified as the imaging area from the console 42, the cassette control unit 92 of the electronic cassette 32 performs an imaging portion arrangement waiting process of detecting whether the imaging portion is disposed at a position corresponding to the imaging area of the irradiation surface 56 corresponding to the received identification number.

Figures 16, 17:
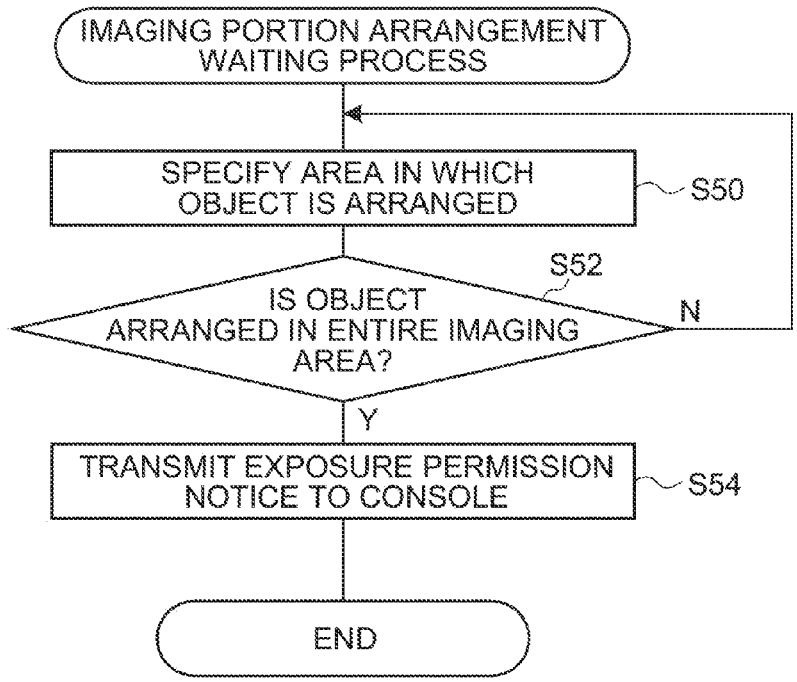
FIG. 16 is a flowchart illustrating the flow of a process of an imaging portion arrangement waiting program according to the second embodiment.
FIG. 17 is a diagram illustrating an example of the amount of radiation and operation conditions in the fluorography mode and the still image capture mode according to another embodiment.

FIG. 16 is a flowchart illustrating the flow of a process of an imaging portion arrangement waiting program executed by a CPU 92A according to this embodiment. The program is stored in a predetermined area of the storage unit 92C in advance.

In Step S50 of FIG. 16, the area 56A of the irradiation surface 56 in which an object is arranged is specified on the basis of the detection result of the touch panel 57.

In Step S52, it is detected whether an object is arranged in all of the areas 56A of the irradiation surface 56 corresponding to the received identification number. When the determination result is "Yes", the process proceeds to Step S54. When the determination result is "No", the process proceeds to Step S50.

In Step S54, an exposure permission notice for permitting the emission of radiation is transmitted to the console 42 by wireless communication and the process ends.

In this way, when an imaging portion is disposed at a position corresponding to the imaging area of the irradiation surface 56 of the electronic cassette 32, the emission of radiation is permitted.

When receiving the radiation permission notice from the electronic cassette 32, the console 42 also displays a message indicating that imaging has been prepared on the display 100. The console 42 validates the reception of the imaging instruction operation through the operation panel 102. When the imaging instruction operation is received, the console 42 transmits the instruction information to start exposure to the radiation generating apparatus 34 and the electronic cassette 32.

As such, according to this embodiment, it is detected whether the imaging portion is disposed at a position where a radiological image is captured in the specified imaging area. When it is detected that the imaging portion is disposed at the position where the radiological image is captured in the imaging area, the radiation generating apparatus 34 is permitted to emit radiation to the imaging area. Therefore, it is possible to prevent radiation from being emitted to the imaging area where no imaging portion is arranged.

In each of the above-described embodiments, the invention is applied to the electronic cassette in a portable radiographic apparatus, but is not limited thereto. The invention may be applied to a stationary radiographic apparatus.

In each of the above-described embodiments, the number of imaging operations is used as the correlation value correlated with the amount of radiation emitted, but the invention is not limited thereto. For example, the correlation value may be the amount of radiation or the irradiation time.

In a case in which the radiographic apparatus performs a still image capture mode that captures one image at a time and a fluorography mode that continuously captures images to obtain a moving image, in some cases, the amount of radiation generated from the radiation generating apparatus 34, an operation for reading the charge stored in the storage capacitor 68 of each pixel unit 74 of the radiation detector 60, and the operation conditions, such as the gain of a charge signal in the signal processing unit 82, are changed in the still image capture mode and the fluorography mode (for example, see Japanese Patent No. 2716949 and JP-A-2009-17484).

FIG. 17 shows an example of the amount of radiation and the operation conditions in the fluorography mode and the still image capture mode.

In the still image capture mode, radiation is emitted to the patient for the time required for imaging to capture an image. However, in the fluorography mode, radiation is continuously emitted to the patient for the imaging period to capture an image. Therefore, in the fluorography mode, in order to significantly reduce the amount of radiation emitted to the patient, the amount of radiation per unit time is several tenths to one-hundredth of that in the still image capture mode. In addition, the fluorography mode requires a maximum of 60 frames/second to 90 frames/second. In order to read the image, the fluorography mode requires sensitivity and a high speed that are several tens of times higher than those of the still image capture mode. Meanwhile, in order to obtain a high-resolution image for diagnosis, the still image capture mode requires a dynamic range close to four digits, but the fluorography mode may require a dynamic range of about two digits.

For example, the fluorography mode is performed for one minute under the following conditions: the frame rate is 30 FPS and the amount of radiation per unit time is 0.1 times that of the still image capture mode. In this case, the amount of radiation emitted once in the fluorography mode is 180 times (0.1×30 FPS×60 SEC=180) the amount of radiation emitted once in the still image capture mode. The number of imaging operations for one minute in the fluorography mode is 1800 (30 FPS×60 SEC=1800).

For example, in a case in which the correlation value is the number of imaging operations and one frame in the fluorography mode is counted as one imaging operation, the number of imaging operations in the fluorography mode is very small, that is, one-tenth of the amount of radiation emitted in a case in which the still images are captured by the same number of imaging operations. In a case in which a series of fluorography is counted as one imaging operation, the number of imaging operations in the fluorography mode is very large, that is, 180 times the amount of radiation emitted by one still image capture operation.

In a case in which the number of imaging operations is used as the correlation value, the number of imaging operations may be counted in one of the still image capture mode and the fluorography mode, and the number of imaging operations in the other mode may be converted into the number of imaging operations in the one mode and then counted. For example, in a case in which the number of imaging operations in the still image capture mode is counted, the amount of radiation per unit time with respect to the still image capture mode×the frame rate×the fluorography period (seconds) is calculated from fluorography conditions (the amount of radiation per unit time with respect to the still image capture mode and the frame rate) and the fluorography period (seconds). In this way, it is possible to convert the number of imaging operations in the fluorography mode into the number of imaging operations in the still image capture mode. For example, when the number of imaging operations in the fluorography mode is counted, the division of the number of imaging operations in the still image capture mode by 0.1 is calculated from the amount of radiation (0.1 times) per unit time with respect to the still image capture mode. In this way, it is possible to convert the number of imaging operations in the still image capture mode into the number of imaging operations in the fluorography mode.

Figure 18:
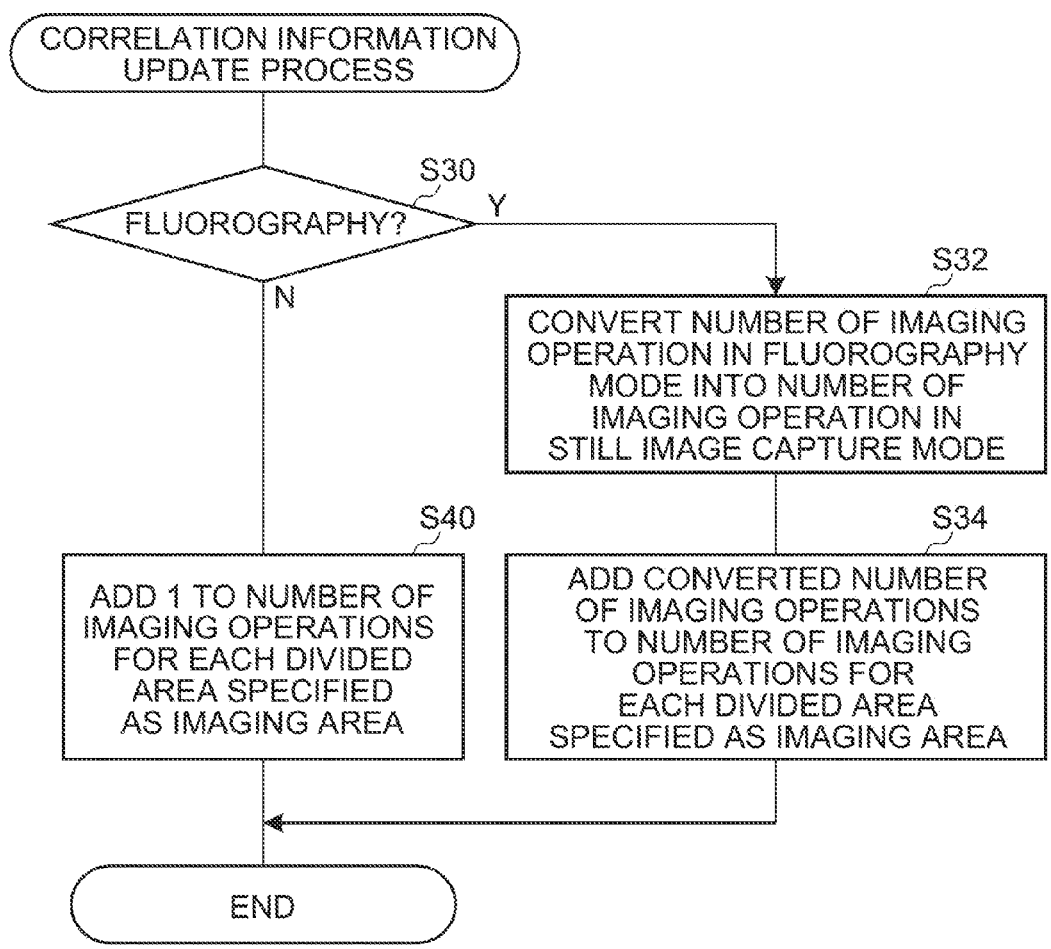
FIG. 18 is a flowchart illustrating the flow of a process of a correlation information update program according to another embodiment.

FIG. 18 shows an example of a correlation information update program in a case in which the number of imaging operations in the still image capture mode is counted. The same portions as those in the first embodiment (FIG. 13) are denoted by the same reference numerals and a description thereof will be omitted.

In Step S30, it is determined whether the fluorography mode is performed. When the determination result is "Yes", the process proceeds to Step 32. On the other hand, when the determination result is "No", the process proceeds to Step S40. When the still image capture mode is performed, the process proceeds to Step S40.

In Step S32, a conversion process of converting the number of imaging operations in the fluorography mode into the number of imaging operations in the still image capture mode is performed.

For example, when the fluorography mode is performed for one minute under the following conditions: the frame rate is 30 FPS and the amount of radiation per unit time is 0.1 times that of the still image capture mode, the number of imaging operations in the fluorography mode is converted into 180 imaging operations (0.1×30 FPS×60 SEC=180) in the still image capture mode.

In Step S34, in the number of imaging operations in each divided area 61A indicated by the correlation information stored in the HDD 110, the number of imaging operations converted in Step S32 is added to the number of imaging operations in the divided area 61A specified as the imaging area by the process of the imaging area specifying program, and the process ends.

The correspondence between fluorography conditions (for example, the amount of radiation per unit time with respect to the still image capture mode, the frame rate, and the imaging time (the time from the first frame to the last n-th frame)) and the number of imaging operations in the still image capture mode may be stored as correspondence information in the HDD 110 in advance, and the number of imaging operations in the still image capture mode corresponding to the number of imaging operations in the fluorography mode may be calculated on the basis of the correspondence information which is stored in the HDD 110 in advance. In this way, in Step S32, the number of imaging operations in the fluorography mode may be converted into the number of imaging operations in the still image capture mode.

Even in a case in which the irradiation time is used as the correlation value, the irradiation time in one of the still image capture mode and the fluorography mode may be accumulated. Then, the irradiation time in the other mode may be converted into the irradiation time in the one mode and then accumulated. For example, in a case in which the irradiation time in the still image capture mode is accumulated, the product of the amount of radiation per unit time in the still image capture mode and the fluorography period (seconds) may be calculated from the fluorography conditions (the amount of radiation per unit time with respect to the still image capture mode) and the fluorography period (seconds). In this way, the irradiation time in the fluorography mode may be converted into the irradiation time in the still image capture mode. In addition, for example, in a case in which the irradiation time in the fluorography mode is accumulated, the division of the irradiation time in the still image capture mode by 0.1 is calculated from the irradiation time (0.1 times) per unit time with respect to the still image capture mode. In this way, it is possible to convert the irradiation time in the still image capture mode into the irradiation time in the fluorography mode.

In the fluorography mode, in some cases, the radiation generating apparatus 34 generates radiation in synchronization with the imaging timing of each frame, and emits radiation in a pulse shape to the electronic cassette 32. In this case, when the irradiation time and the amount of radiation are used as the correlation value, it is preferable that the time between the frames in the fluorography mode is not considered as the irradiation time.

The sensitivity of CsI is reduced as the amount of radiation emitted increases. Therefore, in a case in which the CsI of the scintillator 204 is a columnar crystal, the indirect-conversion-type radiation detector 60 is used to calculate the cumulative amount of radiation for each of predetermined plural divided areas 61A divided from the detection region 61. In a case in which the cumulative amount of radiation is equal to an allowable value, it is possible to prevent a partial reduction in sensitivity by changing the imaging area. In particular, in the moving image capture mode, the amount of radiation for one frame is small, but the number of captured images is large. Therefore, the total amount of radiation is large. Therefore, in the moving image capture mode, it is preferable to change the imaging area in order to maintain the sensitivity.

The correlation value correlated with the amount of radiation may be stored for each imaging date and time. For example, the correlation values may be accumulated and stored for each predetermined period, such as a day. In addition, information related to the intensity (energy) of radiation may be stored together with the correlation value.

Figure 41:
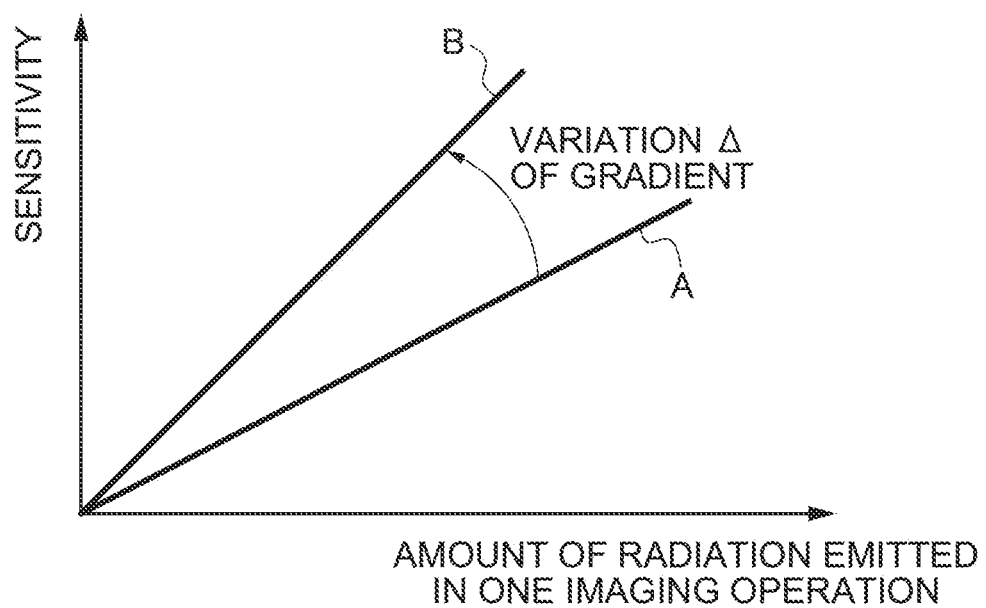
FIG. 41 is a cross-sectional view schematically illustrating the structure of a signal output unit corresponding to one pixel unit of the radiation detector according to the embodiment.
Figure 42:
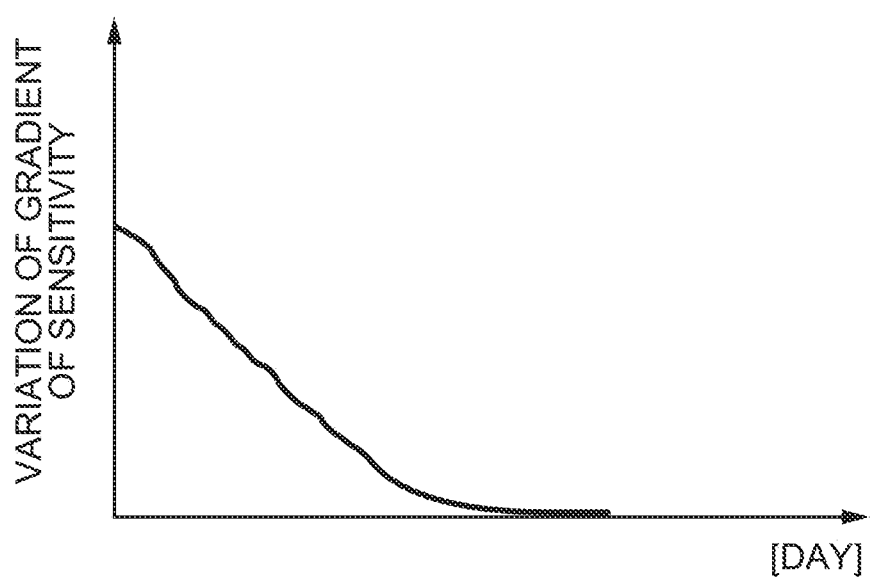
FIG. 42 is a side cross-sectional view illustrating a front surface reading type and a rear surface reading type of the radiation detector for radiation.

When high-intensity (high-energy) radiation is emitted, a temporary variation (so-called deep trap) in the sensitivity of CsI occurs. Specifically, as shown in FIG. 41, the gradient of the amount of light emitted with respect to the amount of radiation emitted in one imaging operation is changed from a line A to a line B, and the sensitivity is improved. As shown in FIG. 42, a variation $\Delta$ in the gradient of the sensitivity line is reduced over about several days. The degree of recovery of the reduction in the variation $\Delta$ of the gradient of the sensitivity line varies depending on the temperature of the CsI. As the temperature of the CsI increases, the reduction rate of the variation $\Delta$ increases. When a recovery coefficient is 1 at a general operation temperature and storage temperature (for example, 25° C.), the recovery coefficient at, for example, 10° C. or less is 0.5 and the recovery coefficient at 40° C. or more is 2.

Therefore, in the electronic cassette 32, in a case in which an imaging area including a specific portion in which sensitivity is changed is used to perform an imaging operation after radiation with a predetermined intensity or more, which causes a variation in sensitivity, is emitted to a specific portion of the detection region 61 of the radiation detector 60, image sticking (so-called ghosting) occurs due to unevenness in the sensitivity of the captured radiological image since the sensitivity of the specific portion is changed.

Irradiation information related to the intensity or emission time of radiation emitted to each of the divided areas 61A may be further stored in the HDD 110, and the imaging area may be specified on the basis of the irradiation information such that the divided area in which the recovery period required to recover a temporary variation in sensitivity caused by the emission of radiation with sufficient intensity to cause the temporary variation in sensitivity has not elapsed is out of the imaging area or the divided area does not overlap a portion of interest of the imaging portion. For example, irradiation information indicating whether radiation with a predetermined intensity or more causing a variation in sensitivity each predetermined period, such as a day, is emitted to each of the divided areas 61A may be stored. When a radiological image is captured, the imaging area may be specified such that the divided area 61A in which a predetermined recovery period (for example, 2 days) required to recover a temporary variation in sensitivity has not elapsed is excluded, or the imaging area may be specified such that the divided area 61A in which the recovery period has not elapsed does not overlap a portion of interest of the imaging portion. In this way, it is possible to prevent image sticking due to a temporary variation in the sensitivity of the CsI and maintain the imaging performance.

Information related to the position of the portion of interest may be stored for each imaging portion in advance, the operator may input the information using the operation panel 102, or the information may be received from another server computer through the network. In addition, plural threshold values of the intensity of radiation causing a variation in sensitivity may be set, the intensity of radiation emitted may be compared with each threshold value, the intensity of radiation emitted may be divided into plural levels, and the recovery period corresponding to each level may be determined.

As described above, the recovery period of the variation in the sensitivity of CsI also varies depending on the temperature.

A temperature sensor may be provided at, for example, the end of the radiation detector 60, the temperature of the radiation detector 60 may be detected by the temperature sensor at any time, and the detected temperature may be stored together with the detection date and time. When a radiological image is captured, the recovery period may be changed on the basis of the temperature state (the average temperature, the maximum temperature, the minimum temperature, and the accumulated temperature) of the radiation detector 60 after radiation with predetermined intensity or more is emitted. For example, in a case in which the average temperature of the radiation detector 60 is 10° C. after radiation with a predetermined intensity or more is emitted, the recovery period may be changed so as to be two times longer than that in a case in which the average temperature of the radiation detector 60 is 25° C. after radiation with a predetermined intensity or more is emitted, or in a case in which the average temperature is 40° C., the recovery period may be changed so as to be half of that in a case in which the average temperature is 25° C.

In each of the above-described embodiments, the size information is stored in order to respond to plural imaging portions, but the invention is not limited thereto. For example, when the size of the area required for imaging is predetermined, it is not necessary to store the size information for each imaging portion.

Figure 19:
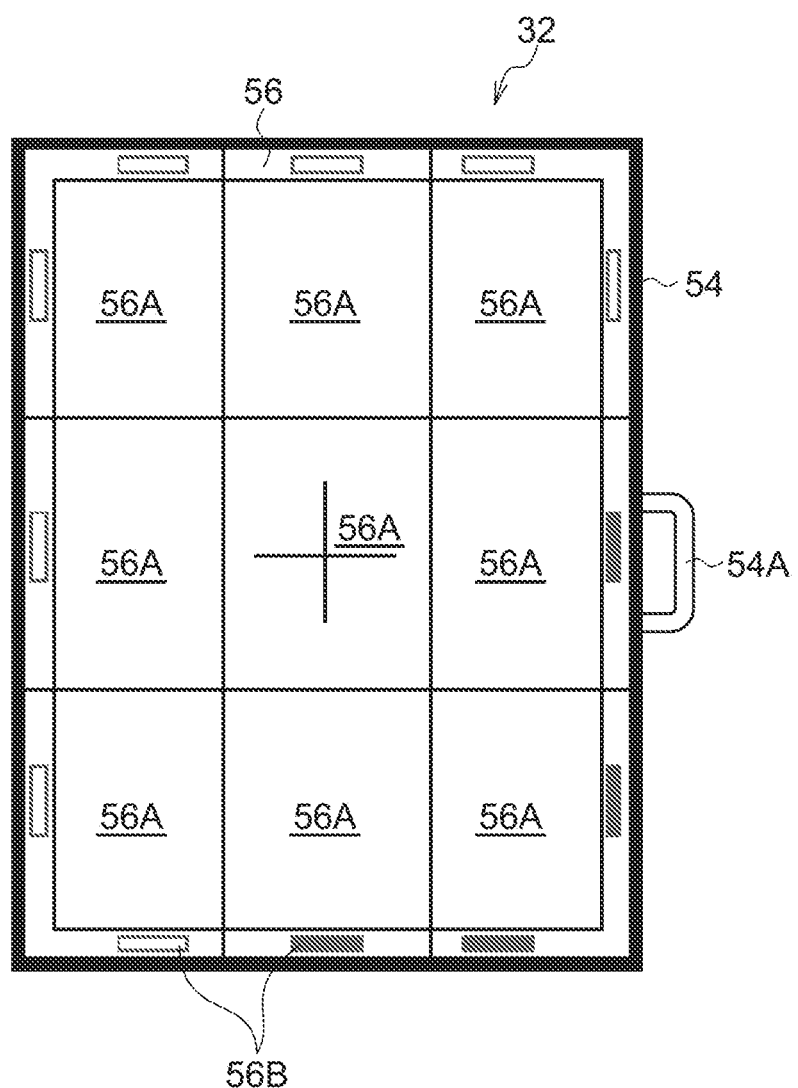
FIG. 19 is a diagram illustrating an example of a presentation component that presents an imaging area according to another embodiment.
Figure 20:
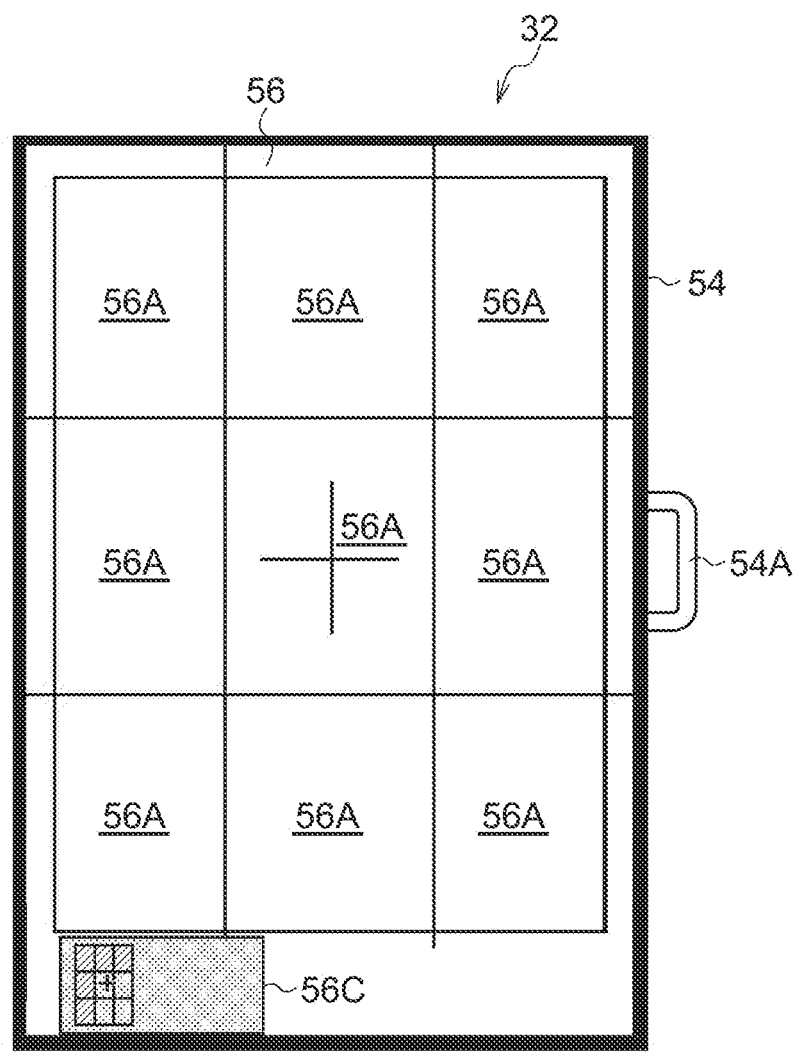
FIG. 20 is a diagram illustrating an example of a presentation component that presents an imaging area according to another embodiment.

In each of the above-described embodiments, the specified imaging area is displayed on the display 100, but the invention is not limited thereto. For example, a presentation component that presents the imaging area may be provided on the irradiation surface 56 of the housing 54 of the electronic cassette 32. FIG. 19 shows an example in which display lamps 56B, such as LEDs, are provided as the presentation components at the ends of each column of the area 56A in the vertical direction and the horizontal direction. The display lamps 56B arranged at the ends of the area 56A specified as the imaging area, are turned on to present the imaging area. FIG. 20 shows an example in which a display portion 56C is provided as the presentation component at the end of the housing 54. The display portion 56C presents the area 56A specified as the imaging area. For example, a visible light lamp and a diaphragm device for presenting an imaging area that is limited as a region illuminated by light emitted from the visible light lamp may be separately provided in the radiation generating apparatus 34, and the imaging area may be presented to the irradiation surface 56 of the housing 54 of the electronic cassette 32 by light emitted from the visible light lamp of the radiation generating apparatus 34. In the case of a stationary radiographic apparatus, since the positional relationship between the radiation generating apparatus 34 and the radiographic apparatus is fixed, it is possible to present the imaging area by controlling the arrangement of the radiation generating apparatus 34 or controlling the diaphragm device for presenting an imaging area. In the case of the electronic cassette 32, for example, an imaging apparatus, such as a camera, may be provided in the radiation generating apparatus 34, and the position and direction of the electronic cassette 32 may be specified from the image captured by the imaging apparatus. Then, the arrangement of the radiation generating apparatus 34 may be controlled on the basis of the specified position and direction of the electronic cassette 32, or the diaphragm device for presenting an imaging area may be controlled to present the imaging area. In addition, for example, a display unit may be provided in the cradle 40 and the area 56A specified as the imaging area may be presented to the display unit.

In each of the above-described embodiments, the number of imaging operations for each combination of the divided areas 61A by which a size capable of capturing an imaging portion is obtained is summed, and the combination of the divided areas 61A with the minimum sum is specified as the imaging area. However, the invention is not limited thereto. For example, the maximum value of the number of imaging operations in each divided area 61A may be calculated for each combination of the divided areas 61A by which a size capable of capturing an imaging portion is obtained, and a combination of the divided areas 61A with the smallest value of the maximum value may be specified as the imaging area.

In each of the above-described embodiments, the detection region 61 is divided into 3×3 (=9) divided areas 61A, but the invention is not limited thereto. For example, the detection region 61 may be finely divided into 5×4 divided areas, and an area corresponding to each pixel unit 74 may be used as the divided area.

In each of the above-described embodiments, combinations of the identification numbers of the divided areas 61A by which each size of the area required for imaging is obtained are stored as the divided area combination information in advance, but the invention is not limited thereto. For example, combinations of the identification numbers of the divided areas 61A by which the size of the area required for imaging is obtained may be calculated by an operation.

In each of the above-described embodiments, the arrangement of the radiation generating apparatus 34 may be controlled or the movable diaphragm device 131 may be controlled such that radiation is emitted to the imaging area. In the case of a stationary radiographic apparatus, since the positional relationship between the radiation generating apparatus 34 and the radiographic apparatus is fixed, it is possible to emit radiation to the imaging area by controlling the arrangement of the radiation generating apparatus 34 or controlling the movable diaphragm device 131. In the case of the electronic cassette 32, for example, an imaging apparatus, such as a camera, may be provided in the radiation generating apparatus 34, and the position and direction of the electronic cassette 32 may be specified from the image captured by the imaging apparatus. Then, the arrangement of the radiation generating apparatus 34 may be controlled on the basis of the specified position and direction of the electronic cassette 32, or the movable diaphragm device 131 may be controlled to emit radiation to the imaging area.

In the second embodiment, the touch panel 57 is provided on the irradiation surface 56 of the electronic cassette 32 and it is detected whether an imaging portion is disposed at a position where a radiological image is captured in the imaging area on the basis of the detection result of the touch panel 57. However, the invention is not limited thereto. For example, an imaging apparatus, such as a camera, may be provided in the radiation generating apparatus 34, the position and direction of the electronic cassette 32 may be specified from the image captured by the imaging apparatus, and it may be detected whether an imaging portion is disposed at a position where a radiological image is captured in the imaging area.

In addition, the structure of the RIS 10 (see FIG. 1), the structure of the radiography room 44 (see FIG. 2), the structure of the electronic cassette 32 (see FIGS. 3, 6, 7, 14, 19, and 20), the structure of the movable diaphragm device 131 (see FIG. 5), the structure of the radiation detector 60 (see FIGS. 38 and 39), and the structure of the imaging system 18 (see FIGS. 4 and 15) according to each of the above-described embodiments are only illustrative. An unnecessary portion may be removed, a new component may be added, or the connection state may be changed, without departing from the scope and spirit of the invention.

The structure of the correlation information, the size information, and the divided area combination information (see FIGS. 8 to 10) according to the above-described embodiments are only illustrative. An unnecessary portion may be removed, a new component may be added, or the information may be changed, without departing from the scope and spirit of the invention.

The flow of the processes of the imaging area specifying program, the correlation information update program, and the imaging portion arrangement waiting program (see FIGS. 11, 13, 16, and 18) are only illustrative. An unnecessary step may be removed, a new step may be added, or the procedure may be changed, without departing from the scope and spirit of the invention.

Next, a case in which the invention is applied to a portable radiographic apparatus (hereinafter, referred to as an "electronic cassette") that is provided with a radiation detector and captures a radiological image represented by emitted radiation will be described.

[Third Embodiment]

First, the structure of a radiology information system 10 according to this embodiment will be described.

FIG. 1 is a block diagram illustrating each component of the radiology information system 10 (hereinafter, referred to an "RIS 10") according to this embodiment.

The RIS 10 is a system for managing information, such as a medical reservation and a diagnosis record, in the department of radiology and forms a portion of a hospital information system (hereinafter, referred to as an "HIS").

The RIS 10 includes plural imaging request terminal apparatuses 12 (hereinafter, also referred to as "terminal apparatuses 12"), an RIS server 14, and plural radiographic systems 18 (hereinafter, also referred to as "imaging systems 18") that are provided in each radiography room (or an operating room) in the hospital, and the components are connected to a hospital intranet 16, such as a wired or wireless LAN (Local Area Network). An HIS server that manages the overall operation of the HIS is also connected to the hospital intranet 16.

The terminal apparatus 12 is for the doctor or the radiographer to input or read diagnosis information or equipment reservation, and is also used to input a request to capture a radiological image or an imaging reservation. The terminal apparatuses 12 each include a personal computer having a display device and can communicate with each other through the RIS server 14 and the hospital intranet 16.

The RIS server 14 receives an imaging request from each of the terminal apparatuses 12 and manages the radiography schedule of the imaging system 18. The RIS server 14 includes a database 14A.

The database 14A stores information (hereinafter, referred to as "patient information") about the patient, such as the attribute information of the patient (for example, name, ID, sex, date of birth, age, blood type, and weight), clinical history, medical examination history, and previously captured radiological images, information (hereinafter, referred to as "electronic cassette information") about an electronic cassette 32, which will be described below, used in the imaging system 18, such as an identification number, a type, a size, sensitivity, a usable imaging portion, starting date to use, and the number of times the electronic cassette 32 is used, and environment information indicating an environment in which the electronic cassette 32 is used to capture a radiological image, that is, an environment in which the electronic cassette 32 is used (for example, a radiography room or an operating room).

The imaging system 18 is operated by the doctor or the radiographer to capture a radiological image according to an instruction from the RIS server 14. The imaging system 18 includes a radiation generating apparatus 34 that irradiates the patient with a dose of radiation X (see FIG. 23) corresponding to exposure conditions from a radiation source 130 (see FIG. 21), the electronic cassette 32 including a radiation detector 60 (see FIG. 23) that outputs an electric signal indicating a radiological image represented by the radiation which passes through an imaging portion of the patient and is then emitted to a detection region, a cradle 40 that charges a battery provided in the electronic cassette 32, and a console 42 that controls the electronic cassette 32, the radiation generating apparatus 34, and the cradle 40.

Figure 21:
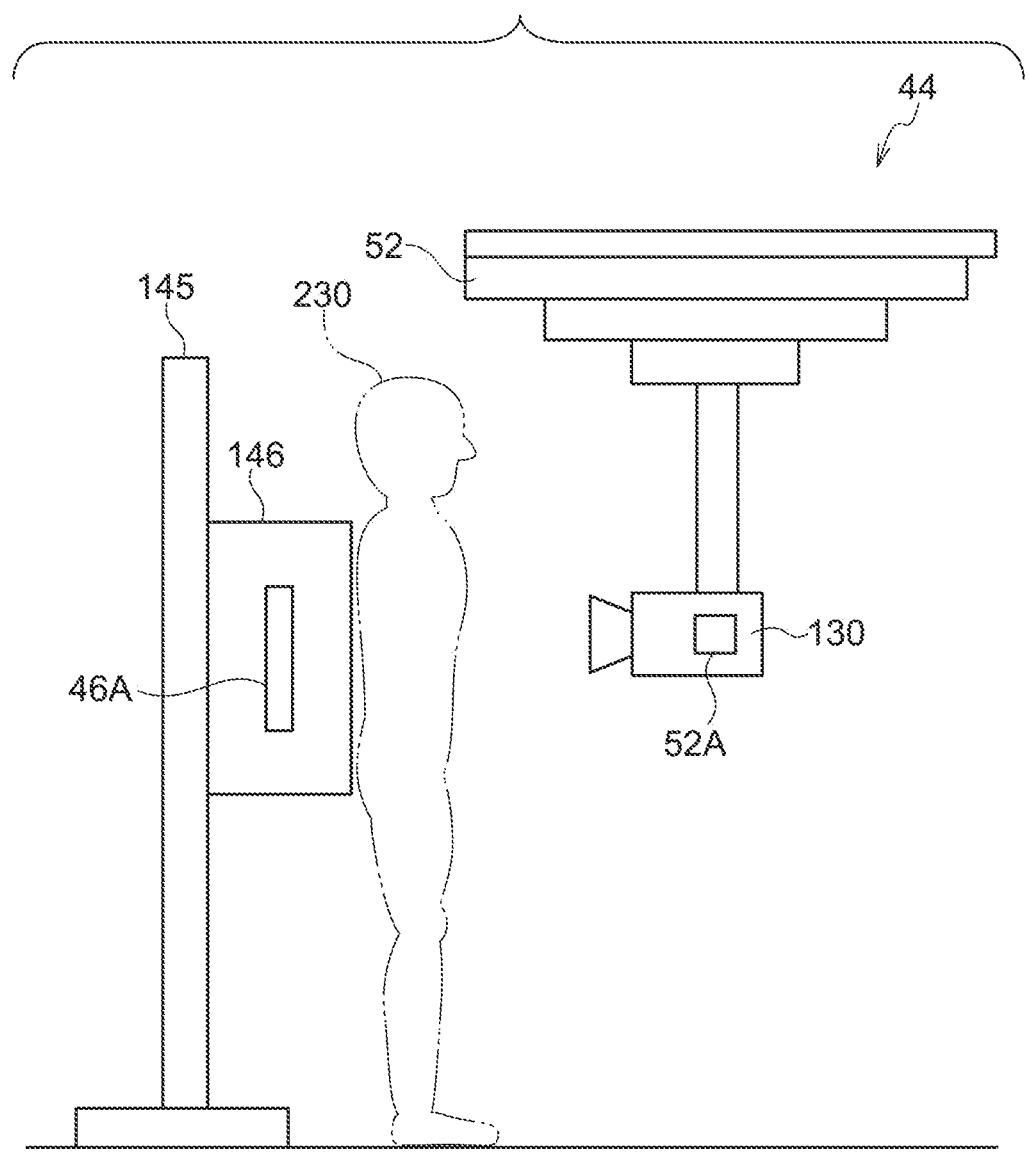
FIG. 21 is a diagram illustrating an example of a radiography room in which a radiographic system according to a third embodiment is installed.
Figure 22:
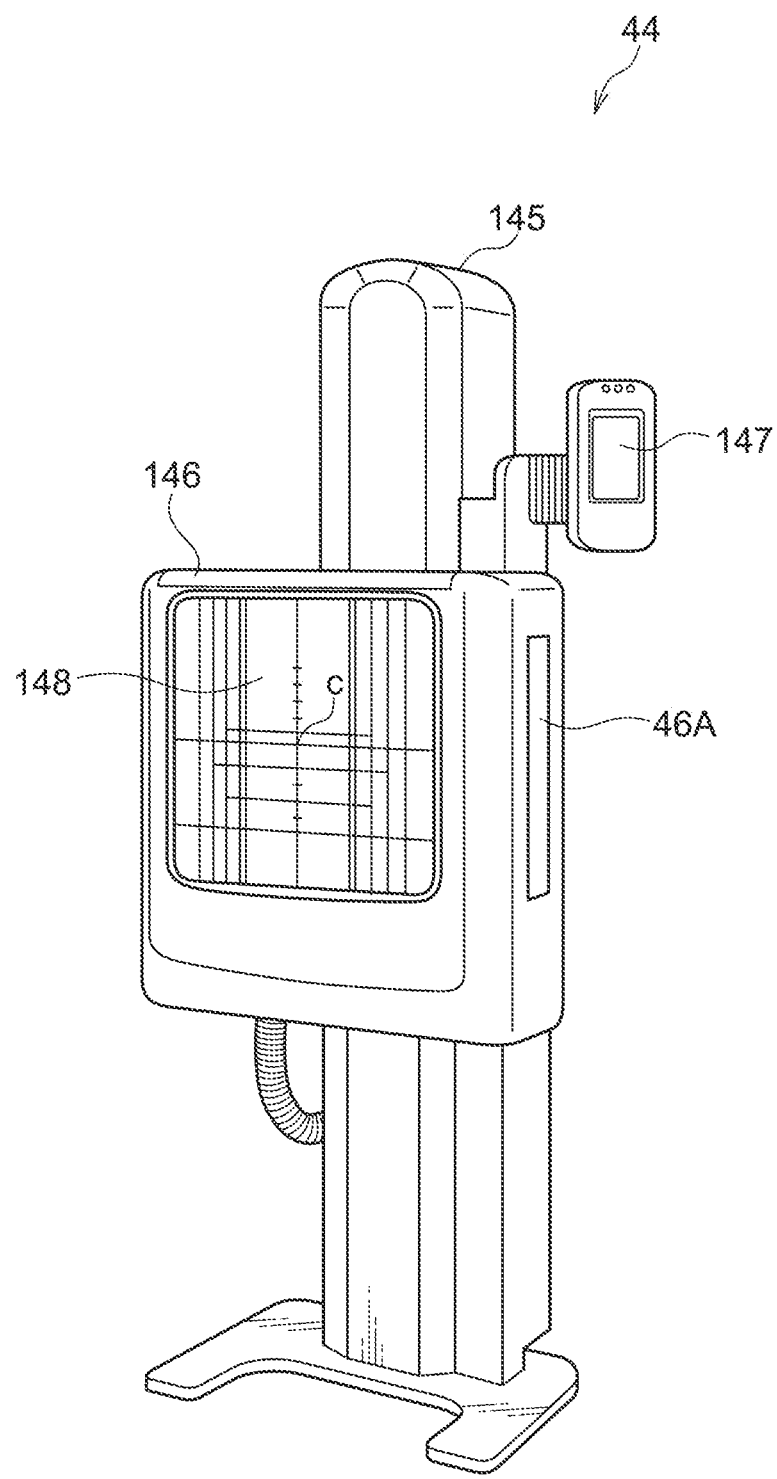
FIG. 22 is a perspective view illustrating the structure of an imaging table according to the third embodiment.

FIGS. 21 and 22 show an example of the arrangement of the imaging system 18 according to the third embodiment in a radiography room 44.

As shown in FIG. 21, the radiography room 44 includes a standing position imaging table 45 for holding the electronic cassette 32 when radiography is performed at a standing position. The front space of the standing position imaging table 45 is a patient imaging position when radiography is performed at the standing position.

In addition, the radiography room 44 includes a supporting/moving mechanism 52 that supports the radiation source 130 so as to be movable in the vertical direction. The supporting/moving mechanism 52 includes an operation panel 52A that controls the movement of the radiation source 130 in the vertical direction and a driving source that moves the radiation source 130 in the vertical direction.

As shown in FIG. 22, the standing position imaging table 45 is configured such that an imaging unit 46 can be moved up and down and includes an operation panel 147 for moving the imaging unit 46 up and down. The imaging unit 46 includes an accommodating unit 46A capable of accommodating the electronic cassette 32. In addition, the center C of an imaging area and the range of the imaging area with each size are indicated in an imaging surface 48 of the imaging unit 46 to which the radiation X is emitted from the radiation source 130.

The electronic cassette 32 is accommodated in the accommodating unit 46A of the imaging unit 46 and is arranged with a gap from the radiation generating apparatus 34 in a case in which a radiological image is captured, as shown in FIG. 21. An imaging position where the patient 30 is disposed is between the radiation generating apparatus 34 and the electronic cassette 32. In a case in which radiography is instructed, the radiation generating apparatus 34 emits a predetermined dose of the radiation X corresponding to predetermined imaging conditions. The radiation X emitted from the radiation generating apparatus 34 passes through the patient 30 disposed at the imaging position. Then, the radiation X having image information carried thereon is emitted to the electronic cassette 32.

The electronic cassette 32 is used not only in the radiography room or the operating room, but may be used for, for example, in a medical examination or on doctor's rounds in the hospital since it is portable.

Figure 23:
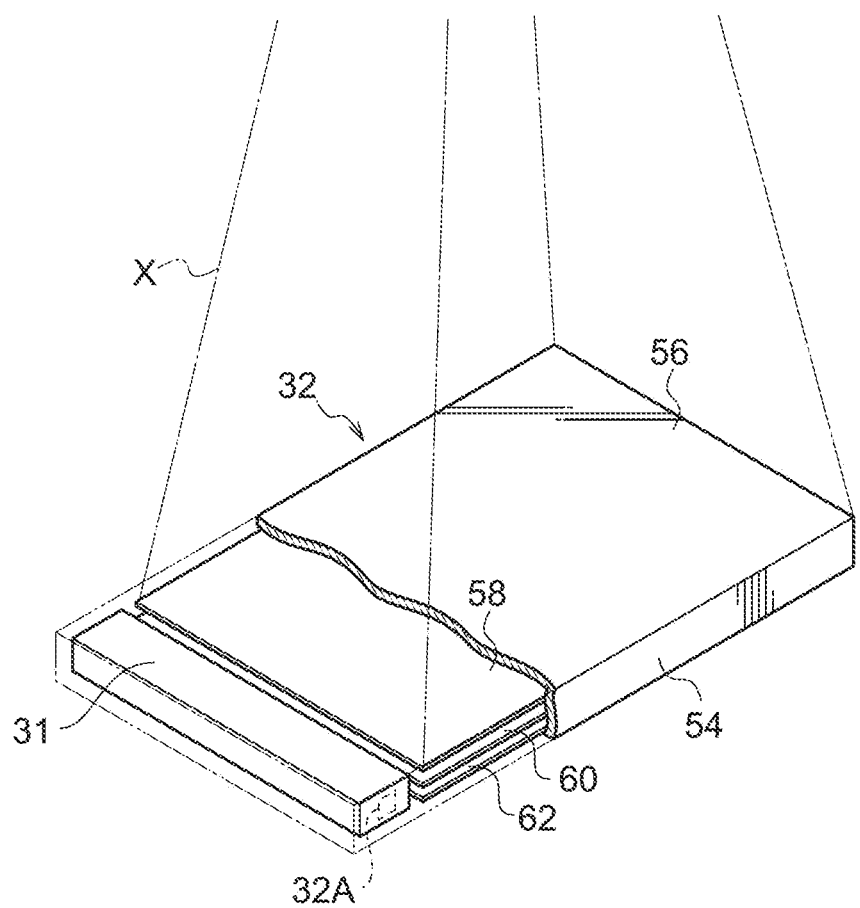
FIG. 23 is a perspective view illustrating the internal structure of an electronic cassette according to the embodiment.

FIG. 23 shows the internal structure of the electronic cassette 32 according to this embodiment.

As shown in FIG. 23, the electronic cassette 32 includes a housing 54 made of a material transmitting the radiation X and has water resistance and airtightness. In a case in which the electronic cassette 32 is used in, for example, the operating room, blood or other contaminants are likely to adhere to the electronic cassette 32. Therefore, the electronic cassette 32 is configured so as to have water resistance and airtightness. If necessary, an antiseptic wash is performed on the electronic cassette 32 such that one electronic cassette 32 can be repeatedly used. A connection terminal 32A is provided on the side surface of the housing 54.

A grid 58 that removes scattered rays of the radiation X by the patient, a radiation detector 60 that detects the radiation X passing through the patient, and a lead plate 62 that absorbs back-scattered rays of the radiation X are provided in the housing 54 in sequential order from an irradiation surface 56 of the housing 54 to which the radiation X is emitted. The irradiation surface 56 of the housing 54 may be configured as the grid 58.

A case 31 that accommodates an electronic circuit including a microcomputer and a chargeable secondary battery is provided at one end of the inside of the housing 54. The radiation detector 60 and the electronic circuit are operated by power supplied from the secondary battery in the case 31. It is preferable that, for example, a lead plate be provided on the irradiation surface 56 of the case 31 in order to prevent various kinds of circuits in the case 31 from being damaged by the radiation X. The electronic cassette 32 according to this embodiment has a rectangular parallelepiped shape in which the irradiation surface 56 has a rectangular shape, and the case 31 is arranged at one end of the electronic cassette 32 in the longitudinal direction.

Figure 24:
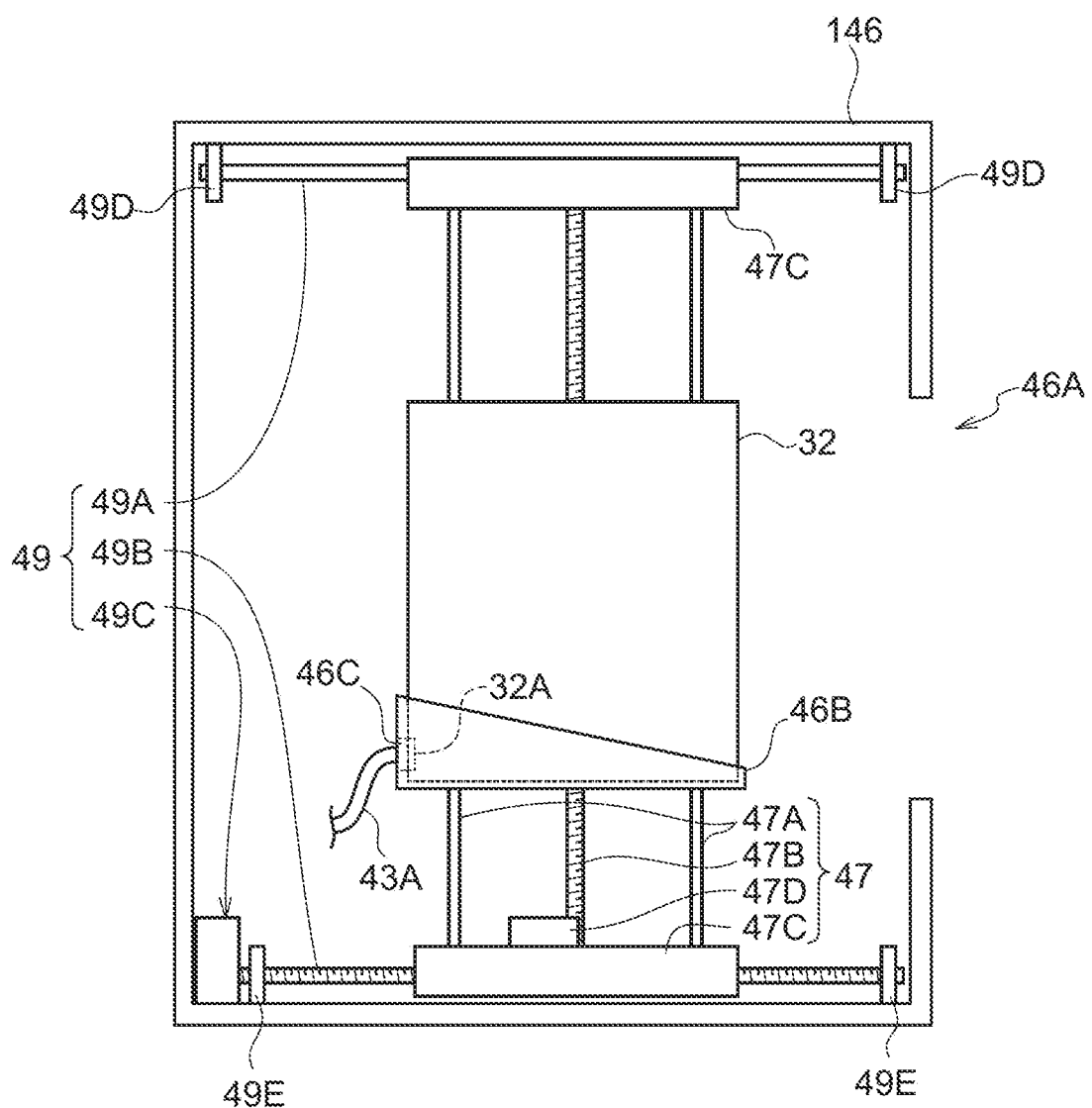
FIG. 24 is a diagram illustrating the internal structure of an imaging unit according to the third embodiment.

As shown in FIG. 24, a holder 46B that holds the electronic cassette 32 accommodated in the accommodating unit 46A is provided in the imaging unit 46. A connection terminal 46C is provided in the holder 46B at a position corresponding to the connection terminal 32A when the electronic cassette 32 is accommodated. The connection terminal 46C comes into contact with the connection terminal 32A when the electronic cassette 32 is accommodated in the accommodating unit 46A such that the electronic cassette 32 can perform communication. The electronic cassette 32 accommodated in the accommodating unit 46A is connected to a console 42 through the connection terminal 32A and a communication cable 43A.

A vertical movement mechanism 47 that moves the holder 46B in the vertical direction in the vertical plane and a horizontal movement mechanism 49 that moves the holder 46B and the vertical movement mechanism 47 in the horizontal direction are provided in the accommodating unit 46A.

The vertical movement mechanism 47 includes a pair of guide rails 47A, a ball screw 47B, a pair of supporting members 47C, and a motor 47D. The pair of guide rails 47A is arranged in parallel to the vertical direction with a predetermined gap therebetween and both ends thereof are fixed to the pair of supporting members 47C. The ball screw 47B is vertically arranged between the pair of guide rails 47A and both ends thereof are rotatably supported by the pair of supporting members 47C. The ball screw 47B is rotated by the motor 47D.

The holder 46B is movably supported by the pair of guide rails 47A and is threadably connected to the ball screw 47B. Therefore, when the ball screw 47B is rotated by the driving force of the motor 47D, the holder 46B is moved in the vertical direction.

The horizontal movement mechanism 49 includes a guide rail 49A, a ball screw 49B, and a motor 49C. The guide rail 49A is provided at an upper part of the accommodating unit 46A in the horizontal direction in the vertical plane parallel to the imaging surface 48, and both ends thereof are fixed to a pair of supporting members 49D. The ball screw 49B is provided at a lower part of the accommodating unit 46A in the horizontal direction in the vertical plane parallel to the imaging surface 48, and both ends thereof are rotatably supported by a pair of supporting members 49E. The ball screw 49B is rotated by the driving force of the motor 49C.

The supporting member 47C on the upper side is movably supported by the guide rail 49A and the supporting member 47C on the lower side is threadably connected to the ball screw 49B. In this way, when the ball screw 49B is rotated by the driving force of the motor 49C, the holder 46B is moved in the horizontal direction together with vertical movement mechanism 47.

FIG. 25 is a block diagram illustrating the structure of a main part of an electric system of the radiographic system 18 according to the third embodiment.

As shown in FIG. 25, the radiation generating apparatus 34 includes a connection terminal 34A for communcation with the console 42. The console 42 includes a connection terminal 42A for communication with the radiation generating apparatus 34. The connection terminal 34A of the radiation generating apparatus 34 and the connection terminal 42A of the console 42 are connected to each other by a communication cable 35.

The radiation detector 60 provided in the electronic cassette 32 may be an indirect conversion type that coverts radiation into light using a scintillator and then converts the light into charge using a photoelectric conversion element, such as a photodiode, or a direct conversion type that converts radiation into charge using a semiconductor layer, such as an amorphous selenium layer. The radiation detector 60 of the direct conversion type is formed by laminating a photoelectric conversion layer that absorbs the radiation X and converts it into charge on a TFT active matrix substrate 66. The photoelectric conversion layer is made of, for example, amorphous a-Se (amorphous selenium) including selenium as a main component (for example, the content of selenium is equal to or more than 50%). When the radiation X is emitted to the photoelectric conversion layer, the quantity of charge (a pair of an electron and a hole) corresponding to the amount of radiation emitted is generated in the photoelectric conversion layer. In this way, the photoelectric conversion layer converts the emitted radiation X into charge. The radiation detector 60 of the indirect conversion type converts the radiation X into charge using a phosphor material and a photoelectric conversion element (photodiode), instead of the radiation-to-charge conversion material for directly converting the radiation X into charge, such as amorphous selenium. As the phosphor material, gadolinium oxysulfide (GOS) or cesium iodide (CsI) is known. In this case, the phosphor material converts the radiation X into light and the photodiode, which is a photoelectric conversion element, converts light into charge.

In addition, plural storage capacitors 68 that store the charge generated in the photoelectric conversion layer or the photoelectric conversion element and plural pixel units 74 (in FIG. 25, the photoelectric conversion layer or the photoelectric conversion element corresponding to each pixel unit 74 is schematically shown as a sensor unit 72), each having a TFT 70 that reads the charge stored in the storage capacitor 68, are arranged in a matrix on the TFT active matrix substrate 66. When the radiation X is emitted to the electronic cassette 32, charge generated in the sensor unit is stored in the storage capacitor 68 of each pixel unit 74. In this way, image information carried by the radiation X emitted to the electronic cassette 32 is converted into charge information and is then held in the radiation detector 60.

In addition, plural gate lines 76 that extend in a predetermined direction (row direction) and are used to turn on or off the TFT 70 of each pixel unit 74 and plural data lines 78 that extend in a direction (column direction) orthogonal to the gate lines 76 and are used to read the stored charge from the storage capacitor 68 through the TFT 70 in an on state are provided on the TFT active matrix substrate 66. Each gate line 76 is connected to a gate line driver 80, and each data line 78 is connected to a signal processing unit 82. When charge is stored in the storage capacitor 68 of each pixel unit 74, each row of the TFTs 70 of the pixel units 74 is sequentially turned on in response to the signal supplied from the gate line driver 80 through the gate line 76. The charge stored in the storage capacitor 68 of the pixel unit 74 having the TFT 70 turned on is transmitted as an analog electric signal to the data line 78 and is then input to the signal processing unit 82. Therefore, the charge stored in each row of the storage capacitors 68 of the pixel units 74 is sequentially read.

The signal processing unit 82 includes amplifiers and sample/hold circuits provided for each data line 78. A charge signal transmitted through each data line 78 is amplified by the amplifier and is then held by the sample/hold circuit. A multiplexer and an A/D (analog/digital) convertor are sequentially connected to the output side of the sample/hold circuit, and the charge signal held by the individual sample/hold circuit is sequentially (serially) input to the multiplexer and is then converted into digital image data by the A/D convertor.

An image memory 90 is connected to the signal processing unit 82, and the image data output from the A/D convertor of the signal processing unit 82 is sequentially stored in the image memory 90. The image memory 90 has storage capacity capable of storing image data corresponding to a predetermined number of frames. Whenever radiography is performed, image data obtained by the radiography is sequentially stored in the image memory 90.

The image memory 90 is connected to a cassette control unit 92 that controls the overall operation of the electronic cassette 32. The cassette control unit 92 is configured as a microcomputer and includes a CPU (Central Processing Unit) 92A, a memory 92B including a ROM and a RAM, and a non-volatile storage unit 92C, such as an HDD or a flash memory.

A wired communication unit 95 is connected to the cassette control unit 92. The wired communication unit 95 is connected to the connection terminal 32A and controls the transmission or reception of various kinds of information to or from the console 42 through the connection terminal 32A and a communication cable 43A. The cassette control unit 92 stores exposure conditions, which will be described below, received from the console 42 through the wired communication unit 95 and starts to read charge on the basis of the exposure conditions.

The electronic cassette 32 is also provided with a power supply unit 96 and the above-mentioned various kinds of circuits or elements (the gate line driver 80, the signal processing unit 82, the image memory 90, the wired communication unit 95, or a microcomputer functioning as the cassette control unit 92) are operated by power supplied from the power supply unit 96. The power supply unit 96 includes a battery (chargeable secondary battery) so as not to impair the portability of the electronic cassette 32 and the charged battery supplies power to various kinds of circuits and elements. In FIG. 25, lines for connecting the power supply unit 96 and various kinds of circuits or elements are not shown.

The console 42 is configured as a server computer and includes a display 100 that displays, for example, an operation menu or a captured radiological image and an operation panel 102 that includes plural keys and receives various kinds of information or operation instructions.

The console 42 according to this embodiment further includes a CPU 104 that controls the overall operation of the console, a ROM 106 that stores in advance various kinds of programs including a control program, a RAM 108 that temporarily stores various kinds of data, an HDD 110 that stores various kinds of data, a display driver 112 that controls the display of various kinds of information on the display 100, and an operation input detecting unit 114 that detects an operation input to the operation panel 102.

The console 42 further includes a communication interface (I/F) unit 116 that transmits or receives various kinds of information, such as exposure conditions, which will be described below, to or from the radiation generating apparatus 34 through the connection terminal 42A and the communication cable 35, a cassette communication unit 118 that transmits or receives various kinds of information, such as exposure conditions or image data, to or from the electronic cassette 32, and an imaging table control unit 120 that controls the driving of the motor 47D provided in the vertical movement mechanism 47 and the driving of the motor 49C provided in the horizontal movement mechanism 49 of the standing position imaging table 45.

The CPU 104, the ROM 106, the RAM 108, the HDD 110, the display driver 112, the operation input detecting unit 114, the communication I/F unit 116, the cassette communication unit 118, and the imaging table control unit 120 are connected to each other by a system bus BUS. Therefore, the CPU 104 can access the ROM 106, the RAM 108, and the HDD 110. In addition, the CPU 104 can control the display of various kinds of information on the display 100 through the display driver 112, the transmission or reception of various kinds of information to or from the radiation generating apparatus 34 through the communication I/F unit 116, the transmission or reception of various kinds of information to or from the electronic cassette 32 through the cassette communication unit 118, and the driving of the motors 47D and 49C, thereby controlling the arrangement position of the electronic cassette 32 in the imaging unit 46. The CPU 104 can also check an operation input to the operation panel 102 by the user through the operation input detecting unit 114.

The radiation generating apparatus 34 includes a radiation source 130 that emits the radiation X, a movable diaphragm device 131 that limits a region irradiated with the radiation X from the radiation source 130, a communication I/F unit 132 that transmits or receives various types of information, such as exposure conditions, to or from the console 42, a radiation source control unit 134 that controls the radiation source 130 on the basis of the received exposure conditions, and a radiation source driving control unit 136 that controls the supply of power to the driving source provided in the supporting/moving mechanism 52 to control the movement of the radiation source 130 in the vertical direction.

The radiation source control unit 134 is also implemented by a microcomputer and stores the received exposure conditions or positional information. The exposure conditions received from the console 42 include information, such as a tube voltage, a tube current, and an irradiation period. When receiving an instruction to start exposure, the radiation source control unit 134 controls the radiation source 130 to emit the radiation X on the basis of the received exposure conditions. The radiation X from the radiation source 130 is emitted to the patient through the movable diaphragm device 131.

As shown in FIG. 5, the movable diaphragm device 131 includes slit plates 135 and 136 and slit plates 137 and 138. The slit plates 135 and 136 and the slit plates 137 and 138 can be moved by the driving force of a motor or a solenoid. In the movable diaphragm device 131, the slit plates 135 and 136 are individually moved in one direction (X direction) to change the region irradiated with the radiation X from the radiation source 130 in the X direction, and the slit plates 137 and 138 are individually moved in a direction (Y direction) intersecting the one direction to change the region irradiated with the radiation X from the radiation source 130 in the Y direction.

An operation panel 52A is used to instruct the vertical movement of the radiation source 130 and the movement of the slit plates 135 and 136 and the slit plates 137 and 138 of the movable diaphragm device 131. The doctor or the radiographer operates the operation panel 52A to adjust the arrangement relationship between the slit plates 135 and 136 and the slit plates 137 and 138, thereby changing the region irradiated with the radiation X. For the region irradiated with the radiation X, for example, a camera may be provided in the vicinity of the radiation source 130 to capture the image of an imaging portion with radiation, and the captured image may be displayed on the display 100 of the console 42 such that the operator can check the captured image. In addition, a visible light lamp that emits visible light may be provided in the vicinity of the radiation source 130 and emit visible light to an imaging portion of the body of the examinee such that the operator can check the imaging portion.

The structure of the indirect-conversion-type radiation detector 60 that indirectly converts radiation into charge using a phosphor material and a photoelectric conversion element is described in the above and thus a detailed description thereof will be omitted.

Next, the operation of this embodiment will be described. First, the overall operation of the RIS 10 according to this embodiment will be described briefly.

In a case in which a radiological image is captured, the terminal apparatus 12 (see FIG. 1) receives an imaging request from the doctor or the radiographer. The usage environment of the electronic cassette 32, the date of imaging, an imaging portion, which is an imaging target, a tube voltage, and a dose of radiation are designated by the imaging request.

The terminal apparatus 12 notifies the RIS server 14 of the content of the received imaging request. The RIS server 14 stores the content of the imaging request notified by the terminal apparatus 12 in the database 14A.

The console 42 accesses the RIS server 14 to acquire the content of the imaging request from the RIS server 14, and displays the content of the imaging request on the display 100 (see FIG. 25).

The doctor or the radiographer starts to capture a radiological image on the basis of the content of the imaging request displayed on the display 100.

For example, in a case in which the radiological image of the breast of a patient 230 shown in FIG. 21 is captured, the doctor or the radiographer puts the electronic cassette 32 in the accommodating unit 46A of the imaging unit 46, and adjusts the height of the imaging unit 46 such that the center of the imaging surface 48 of the imaging unit 46 corresponds to the breast of the patient 230. Then, the doctor or the radiographer operates the operation panel 52A to arrange the radiation generating apparatus 34 in front of an imaging portion, and operates the movable diaphragm device 131 to limit the region irradiated with the radiation X such that the radiation X is emitted only to the imaging portion and the periphery thereof. In addition, the doctor or the radiographer uses the operation panel 102 of the console 42 to designate exposure conditions, such as a tube voltage, a tube current, and an irradiation period when the radiation X is emitted, according to the imaging portion of the patient or the imaging conditions. The designated exposure conditions are transmitted to the radiation generating apparatus 34 and the electronic cassette 32.

However, in a case in which radiography is repeatedly performed using a specific portion of a detection region 161 of the radiation detector 60 capable of detecting radiation, only the portion of the detection region deteriorates.

Therefore, in this embodiment, as shown in FIG. 6, the detection region 161 of the radiation detector 60 is divided into 3×3 (=9) divided areas 161A, and a correlation value correlated with the amount of radiation emitted to each of the divided areas 161A is stored as correlation information in the HDD 110. In each of the divided areas 161A, a number in parentheses (for example, (1)) indicates an identification number for identifying each divided area 161A.

FIG. 8 shows an example of the data structure of the correlation information stored in the HDD 110.

In this embodiment, the number of imaging operations using the divided areas 161A is stored as the correlation value for each of the identification numbers of the divided areas 161A.

In this embodiment, for each imaging portion of the patient whose radiological image is captured, size information indicating the size of the area required to capture the radiological image of the imaging portion is stored in the HDD 110.

FIG. 9 shows an example of the data structure of the size information stored in the HDD 110.

In this embodiment, the number of divided areas 161A in the vertical direction and the horizontal direction is stored as size information required to capture the radiological image of each imaging portion. For example, in a case in which the image of the hand, which is an imaging portion, is captured, a total of four (2×2 (two in the vertical direction and two in the horizontal direction)) divided areas 161A are needed.

In this embodiment, divided area combination information indicating combinations of the divided areas 161A by which each size of the area required for imaging is obtained in the detection region 161 is stored in the HDD 110.

FIG. 10 shows an example of the data structure of the divided area combination information stored in the HDD 110.

In this embodiment, combinations of the identification numbers of the divided areas 161A by which each size of the area required for imaging is obtained are stored. For example, in a case in which the size of the area required for imaging is 2×2, four combinations of the identification numbers of the divided areas 161A, that is, (1, 2, 4, 5), (2, 3, 5, 6), (4, 5, 7, 8), and (5, 6, 8, 9) are stored.

When a predetermined operation instruction to prepare for imaging is input to the operation panel 102, the console 42 performs an imaging area specifying process of specifying an imaging area capable of capturing the radiological image of an imaging portion while preventing variations in the amount of radiation emitted to each of the divided areas 161A of the radiation detector 60.

Figure 26:
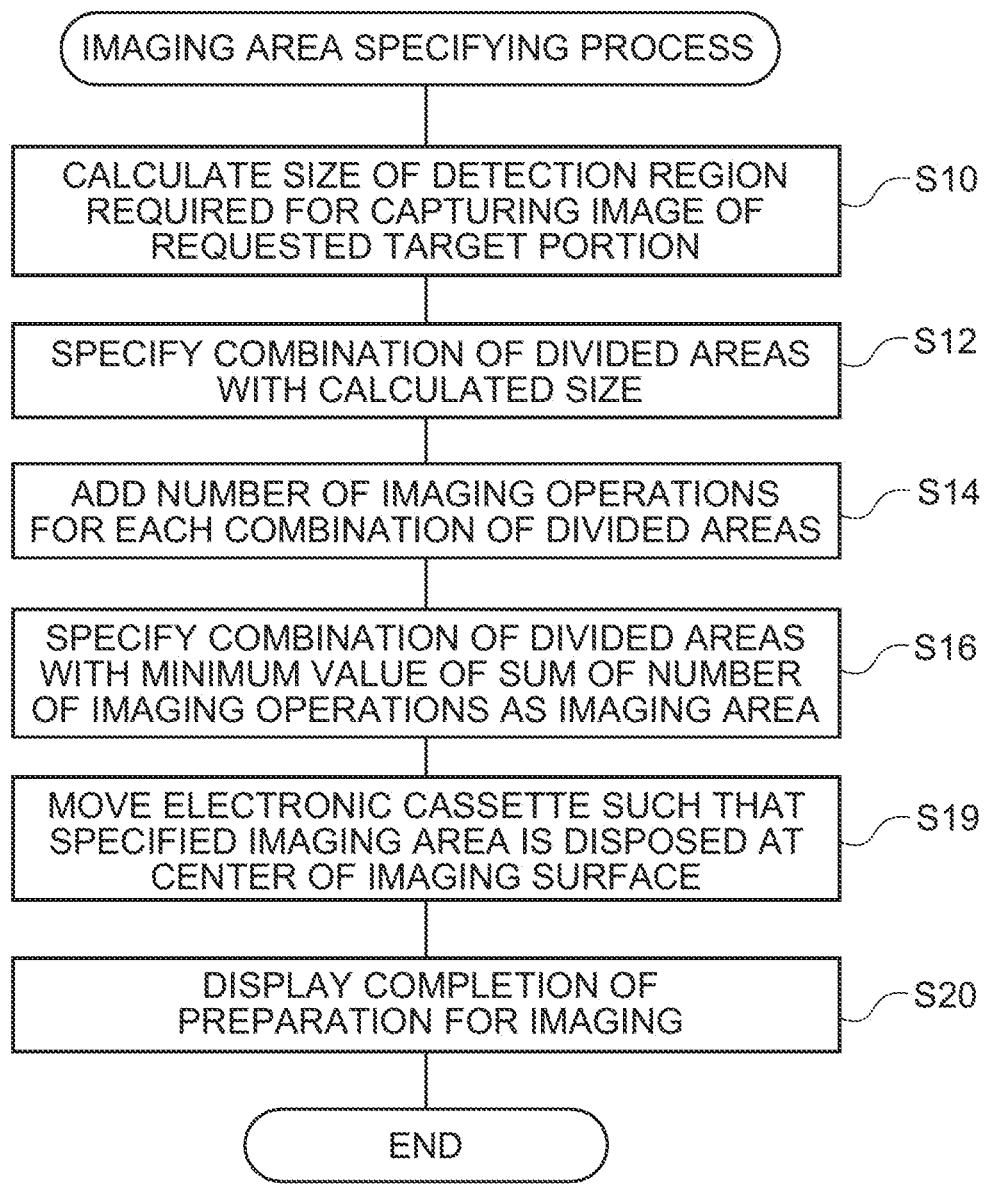
FIG. 26 is a flowchart illustrating the flow of a process of an imaging area specifying program according to the third embodiment.

FIG. 26 is a flowchart illustrating the flow of a process of an imaging area specifying program executed by the CPU 104 according to this embodiment. The program is stored in a predetermined area of the HDD 110 in advance.

In Step S10 of FIG. 26, the size of the divided area 161A corresponding to an imaging portion that is requested to be captured by the imaging request is read from the size information stored in the HDD 110.

In Step S12, a combination of the divided areas 161A by which the size read in Step S12 is obtained is specified on the basis of the divided area combination information stored in the HDD 110.

In Step S14, the number of imaging operations in each divided area 161A which is indicated by the correlation information stored in the HDD 110 is summed for each combination of the divided areas 161A specified in Step S14.

In Step S16, a combination of the divided areas 161A with the minimum sum of the number of imaging operations calculated in Step S14 is specified as an imaging area.

In Step S19, the position of the electronic cassette 32 is moved such that the center of the imaging area specified in Step S16 is disposed at the center C of the imaging surface 48 of the imaging unit 46.

In Step S20, the completion of preparation for imaging is displayed on the display 100, and the process ends.

When the completion of preparation for imaging is displayed on the display 100, the doctor or the radiographer operates the operation panel 102 of the console 42 to input an imaging instruction.

When the imaging instruction is input through the operation panel 102, the console 42 transmits instruction information to start exposure to the radiation generating apparatus 34 and the electronic cassette 32. Then, the radiation source 130 generates and emits radiation at a tube voltage and a tube current and for an irradiation period corresponding to the exposure conditions received from the console 42.

In this way, radiation is emitted to the divided area 161A of the radiation detector 60 specified as the imaging area and the radiological image is captured. Therefore, it is possible to prevent only a specific portion of the detection region 161 from deteriorating.

After the irradiation period designated in the exposure conditions has elapsed from the reception of the instruction information to start exposure, the cassette control unit 92 of the electronic cassette 32 instructs the gate line driver 80 to sequentially output an on signal to each gate line 76, thereby sequentially turning on each line of the TFTs 70 connected to each gate line 76.

In the radiation detector 60, when each line of the TFTs 70 connected to each gate line 76 is sequentially turned on, charge stored in each line of the storage capacitors 68 flows as an electric signal to each data line 78. The electric signal flowing to each data line 78 is converted into digital image data by the signal processing unit 82 and is then stored in the image memory 90.

After the imaging operation ends, the cassette control unit 92 transmits the image information stored in the image memory 90 to the console 42.

The console 42 performs various kinds of correction processes, such as shading correction, on the received image information and performs image processing for trimming the image of a portion corresponding to the divided area 161A specified as the imaging area. Then, the console 42 stores the image information subjected to image processing in the HDD 110. The image information stored in the HDD 110 is displayed on the display 100 such that the captured radiological image can be checked. In addition, the image information is transmitted to the server computer forming the RIS (Radiology Information System) through the network and is then stored in the database. In this way, the doctor can interpret the captured radiological image or make a diagnosis.

After the image information subjected to image processing is stored in the HDD 110, the console 42 performs a correlation information update process of updating the correlation information stored in the HDD 110.

FIG. 13 is a flowchart illustrating the flow of a process of a correlation information update program executed by the CPU 104 according to this embodiment. The program is stored in a predetermined area of the HDD 110 in advance.

In Step S40 of FIG. 13, in the number of imaging operations in each divided area 161A indicated by the correlation information stored in the HDD 110, 1 is added to the number of imaging operations in the divided area 161A specified as the imaging area by the process of the imaging area specifying program, and the process ends.

In this way, the number of imaging operations in each divided area 161A which is stored as the correlation information is updated.

As described above, according to this embodiment, the position of the electronic cassette 32 is moved such that the divided area 161A of the radiation detector 60 specified as the imaging area is disposed at the center C of the imaging surface 48 of the imaging unit 46, and radiation X is emitted to the imaging area to perform image capture. Therefore, the radiation X is emitted to the detection region 161 of the radiation detector 60 while being scattered. As a result, it is possible to prevent the deterioration of a specific portion of the detection region 161 of the radiation detector 60.

[Fourth Embodiment]

Next, a case in which the invention is applied to fluorography will be described.

The structure of a radiology information system 10 according to a fourth embodiment is the same as that of the third embodiment (see FIG. 1) and thus a description thereof will be omitted.

Figure 27:
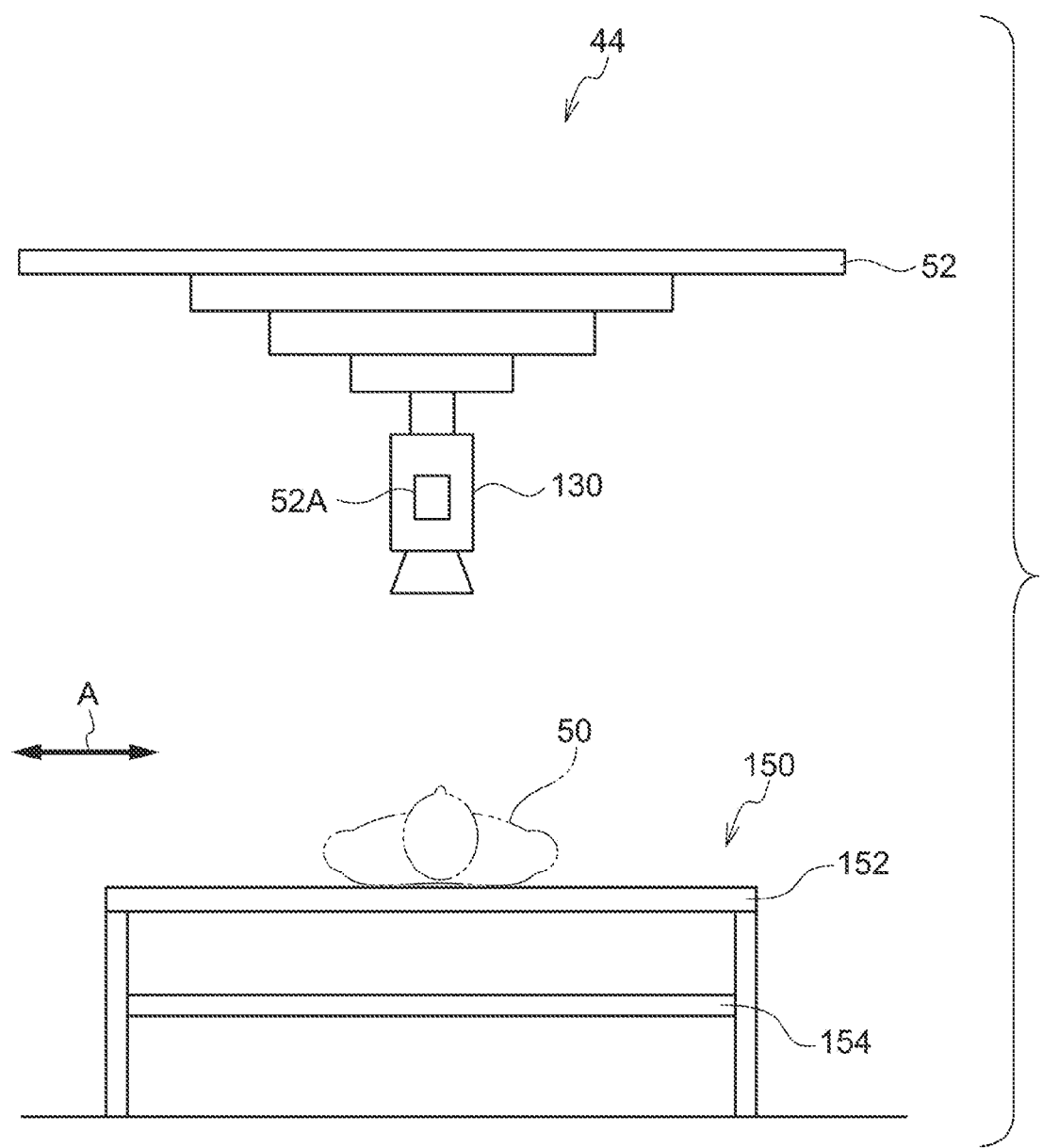
FIG. 27 is a diagram illustrating an example of a radiography room in which a radiographic system according to a fourth embodiment is installed.
Figure 28:
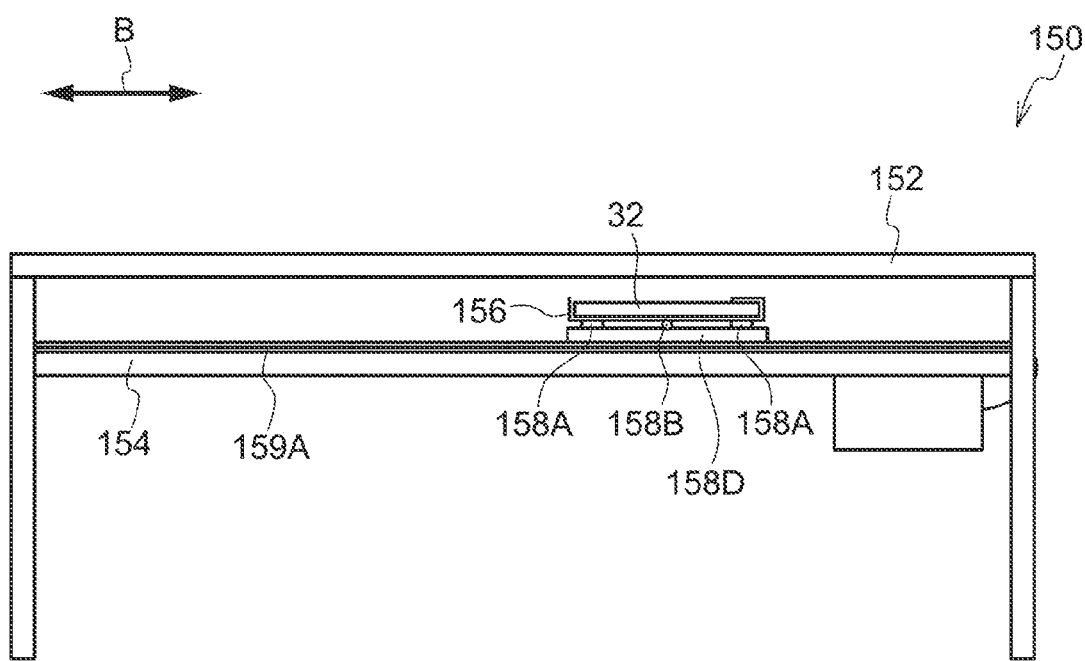
FIG. 28 is a side view illustrating the structure of an imaging table according to the fourth embodiment.
Figure 29:
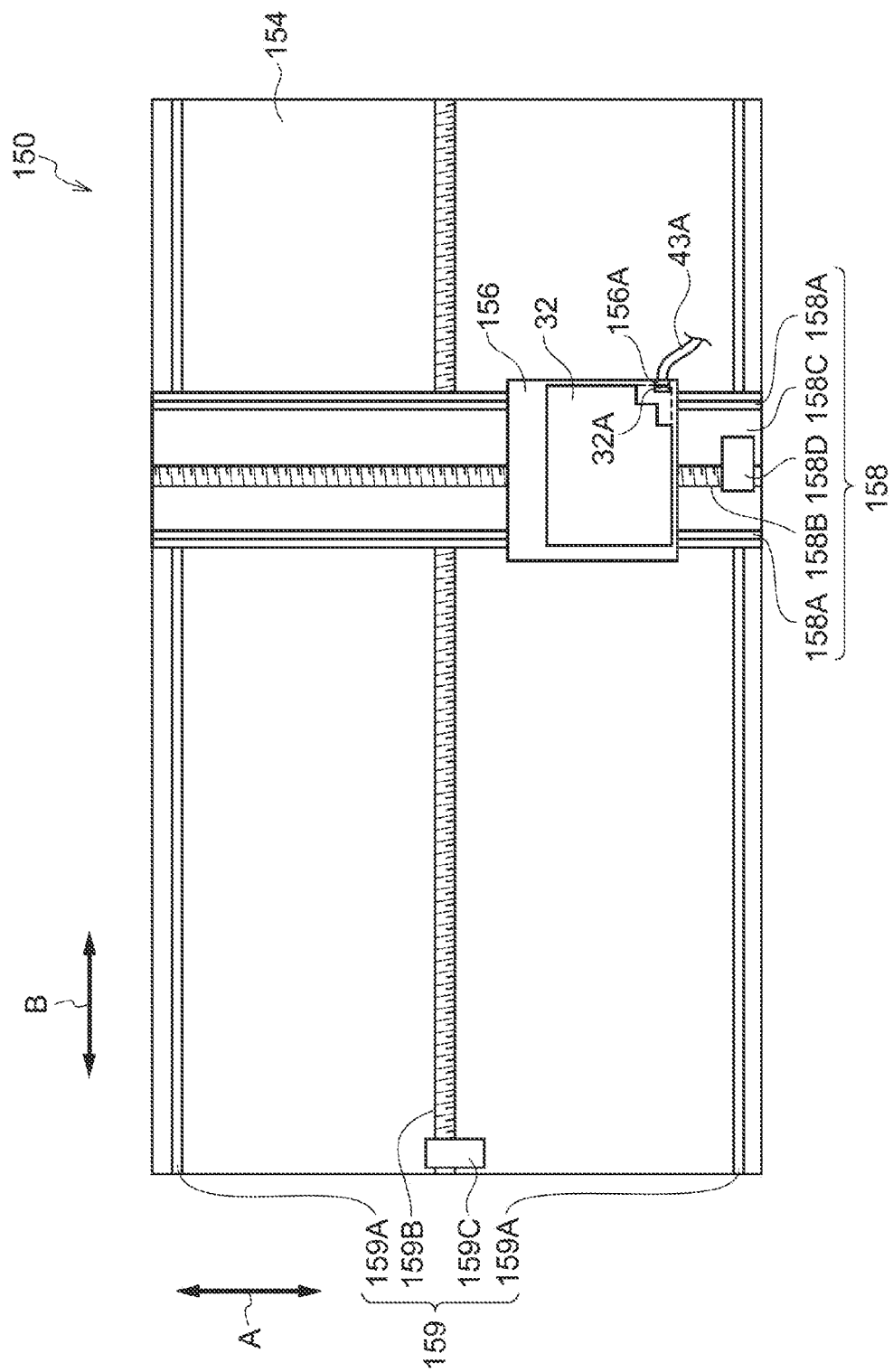
FIG. 29 is a plan view illustrating the structure of a cassette mounting plate portion of the imaging table according to the fourth embodiment.

FIGS. 27 to 29 show an example of the arrangement of an imaging system 18 according to the fourth embodiment in a radiography room 44.

As shown in FIG. 27, the radiography room 44 includes a supine position imaging table 150 on which the patient lies when radiography is performed at a supine position. The upper space of the supine position imaging table 150 is a patient imaging position when radiography is performed at the supine position.

In addition, a supporting/moving mechanism 52 supports the radiation source 130 so as to be movable in the horizontal plane and in the vertical direction. The supporting/moving mechanism 52 includes an operation panel 52A that instructs the movement of the radiation source 130 in the horizontal plane and in the vertical direction and a driving source that moves the radiation source 130 in the horizontal plane and in the vertical direction.

As shown in FIG. 28, the supine position imaging table 150 has a double-deck structure of a top plate 152 and a cassette mounting plate 154. A tray 156 on which the electronic cassette 32 is mounted is provided on the cassette mounting plate 154.

As shown in FIG. 29, a connection terminal 156A is provided in the tray 156 at a position corresponding to the connection terminal 32A in a case in which the electronic cassette 32 is accommodated. The connection terminal 32A comes into contact with the connection terminal 156A such that the electronic cassette 32 can perform communication in a case in which the electronic cassette 32 is accommodated in an accommodating unit 46A. The electronic cassette 32 accommodated in the tray 156 is connected to the console 42 through the connection terminal 156A and a communication cable 43A.

The supine position imaging table 150 is provided with a width direction movement mechanism 158 that moves the tray 156 in the width direction (direction A in FIG. 28) of the supine position imaging table 150 and a length direction movement mechanism 159 that moves the tray 156 and the width direction movement mechanism 158 in the horizontal plane in the length direction (direction B).

The width direction movement mechanism 158 includes a pair of guide rails 158A, a ball screw 158B, a supporting table 158C, and a motor 158D.

The supporting table 158C is a flat plate, has a length that is substantially equal to the width of the cassette mounting plate 154, and is arranged in the width direction of the cassette mounting plate 154. The pair of guide rails 158A is arranged in parallel to the width direction with a predetermined gap therebetween and is fixed to the supporting table 158C. The ball screw 158B is arranged in the width direction between the pair of guide rails 158A and both ends thereof are rotatably supported by the supporting table 158C. The ball screw 158B is rotated by the driving force of a motor 158D.

The tray 156 is movably supported by the pair of guide rails 158A and is threadably connected to the ball screw 158B. Therefore, when the ball screw 158B is rotated by the driving force of the motor 158D, the tray 156 is moved in the width direction along the guide rails 158A.

The length direction movement mechanism 159 includes a pair of guide rails 159A, a ball screw 159B, and a motor 159C. The pair of guide rails 159A is provided in parallel to each other in the length direction with a predetermined gap therebetween. The ball screw 159B is arranged in the length direction between the pair of guide rails 159A and is rotated by the driving force of the motor 159C.

The supporting table 158C is movably supported by the pair of guide rails 159A and is threadably connected to the ball screw 159B. Therefore, when the ball screw 159B is rotated by the driving force of the motor 159C, the supporting table 158C supporting the tray 156 is moved in the length direction along the guide rails 159A.

FIG. 30 is a block diagram illustrating the structure of a main part of an electric system of the radiographic system 18 according to the fourth embodiment. In FIG. 30, the same components as those in the third embodiment (see FIG. 25) are denoted by the same reference numerals and a description thereof will be omitted.

The imaging table control unit 120 provided in the console 42 controls the driving of the motor 158D provided in the horizontal movement mechanism 158 and the driving of the motor 159C provided in the length direction movement mechanism 159 of the supine position imaging table 150.

The radiation source driving control unit 136 controls the supply of power to each driving source provided in the supporting/moving mechanism 52 to control the movement of the radiation source 130 in the horizontal plane and in the vertical direction. The radiation source control unit 134 specifies the irradiation range of the radiation X from the radiation source 130 to the supine position imaging table 150 on the basis of the operations of the radiation source driving control unit 136 and the movable diaphragm device 131 and notifies the console 42 of the specified irradiation range.

Next, the operation of this embodiment will be described.

In a case in which fluorography is performed, the doctor or the radiographer operates the console 42 to designate fluorography and exposure conditions, such as a tube voltage and a tube current. The designated exposure conditions are transmitted to the radiation generating apparatus 34 and the electronic cassette 32. Then, the doctor or the radiographer puts the electronic cassette 32 in the tray 156 of the supine position imaging table 150. In addition, the doctor or the radiographer operates the operation panel 52A to arrange the radiation generating apparatus 34 above an imaging portion and control the movable diaphragm device 131 to limit the region irradiated with the radiation X such that the radiation X is emitted only to the imaging portion and the periphery thereof. In addition, when the doctor or the radiographer operates the operation panel 52A to operate the radiation source driving control unit 136 and the movable diaphragm device 131, the radiation source control unit 134 specifies the irradiation range of the radiation X emitted from the radiation source 130 to the supine position imaging table 150 on the basis of the operation state of the radiation source driving control unit 136 and the movable diaphragm device 131 and notifies the console 42 of the specified irradiation range.

The console 42 controls the driving of the motor 158D and the motor 159C to arrange the electronic cassette 32 such that the detection region 161 is disposed within the notified irradiation range, and displays the completion of preparation for imaging on the display 100.

When the completion of preparation for imaging is displayed on the display 100, the doctor or the radiographer operates the operation panel 102 of the console 42 to input an instruction to start an imaging operation.

When the imaging start instruction is input through the operation panel 102, the console 42 transmits instruction information to start exposure to the radiation generating apparatus 34 and the electronic cassette 32. Then, the radiation source 130 starts to emit radiation at a tube voltage and a tube current corresponding to the exposure conditions received by the radiation generating apparatus 34 from the console 42.

When receiving the instruction information to start exposure, the cassette control unit 92 of the electronic cassette 32 repeatedly performs a process of controlling the gate line driver 80 to sequentially output an on signal to each gate line 76 with a predetermined period and sequentially turning on each line of the TFTs 70 connected to each gate line 76 to read an image, thereby continuously reading images. The electric signal flowing to each data line 78 of the radiation detector 60 is converted into digital image data by the signal processing unit 82 and is then stored in the image memory 90. In addition, the images are transmitted one by one to the console 42.

The console 42 performs various kinds of correction processes, such as shading correction, on the received image information and performs image processing for trimming the image in the irradiation range of the radiation X. Then, the console 42 displays the image information subjected to image processing on the display 100 and stores the image information as moving image data in the HDD 110. In a case in which an imaging end instruction is input through the operation panel 102, the console 42 transmits instruction information to end exposure to the radiation generating apparatus 34 and the electronic cassette 32. Then, the radiation source 130 stops the emission of radiation and the electronic cassette 32 ends the reading of images.

However, when fluorography is repeated such that the radiation X is emitted only to a specific portion of the radiation detector 60 as the irradiation range, only the portion deteriorates.

Therefore, in this embodiment, the position of the electronic cassette 32 is moved such that the irradiation range of the radiation X is not out of the detection region 161 during fluorography.

When an instruction to start an imaging operation is input through the operation panel 102, the console 42 performs a movement process of moving the position of the electronic cassette 32 periodically.

Figure 31:
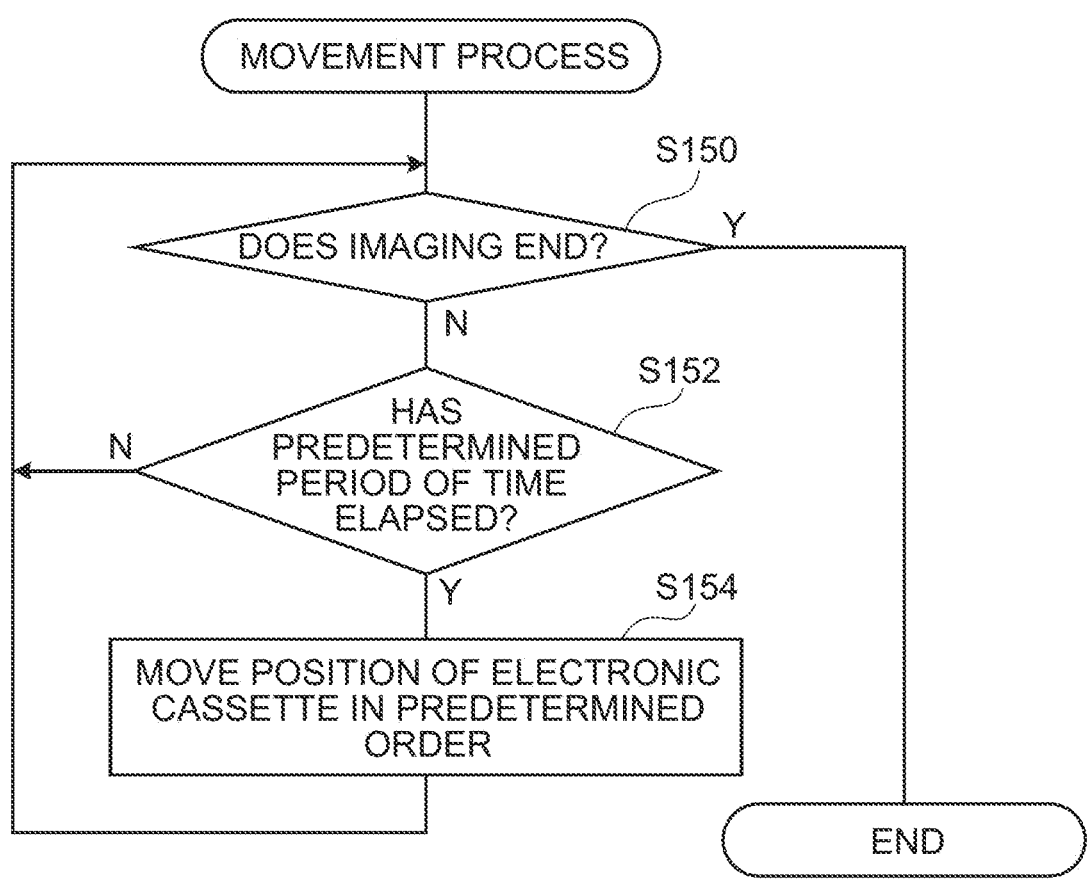
FIG. 31 is a flowchart illustrating the flow of a process of a movement processing program according to the fourth embodiment.

FIG. 31 is a flowchart illustrating the flow of a movement processing program executed by the CPU 104 according to this embodiment. The program is stored in a predetermined area of the HDD 110 in advance.

In Step S150 of FIG. 31, whether fluorography ends is determined. When the determination result is "Yes", the process ends. When the determination result is "No", the process proceeds to Step S152.

In Step S152, whether a predetermined period of time (for example, 30 seconds) has elapsed from the movement of the previous position of the electronic cassette 32 is determined. When the determination result is "Yes", the process proceeds to Step S154. When the determination result is "No", the process proceeds to Step S150.

Figure 32:
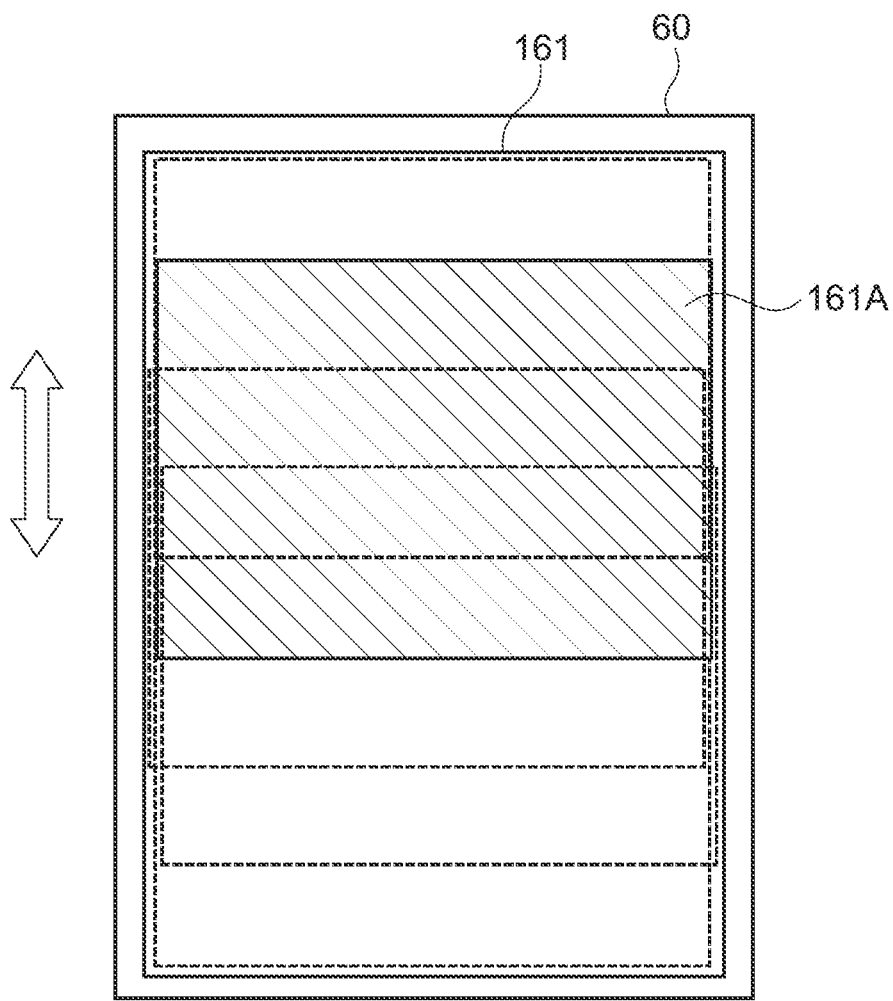
FIG. 32 is a diagram illustrating an example of the order in which an electronic cassette according to the fourth embodiment is moved.
Figure 33:
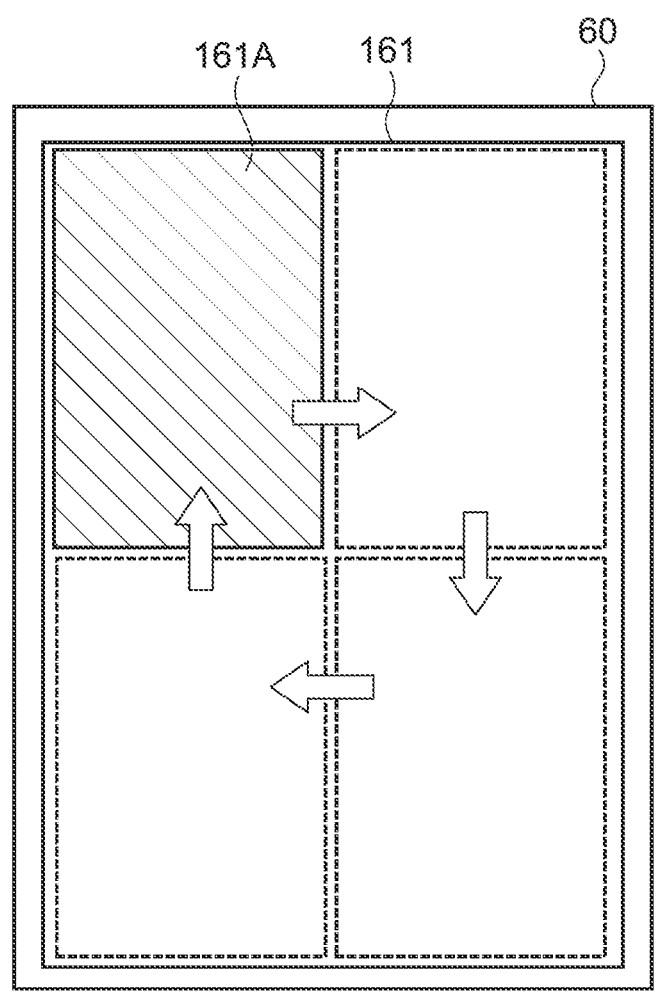
FIG. 33 is a diagram illustrating an example of the order in which the electronic cassette according to the fourth embodiment is moved.
Figure 37:
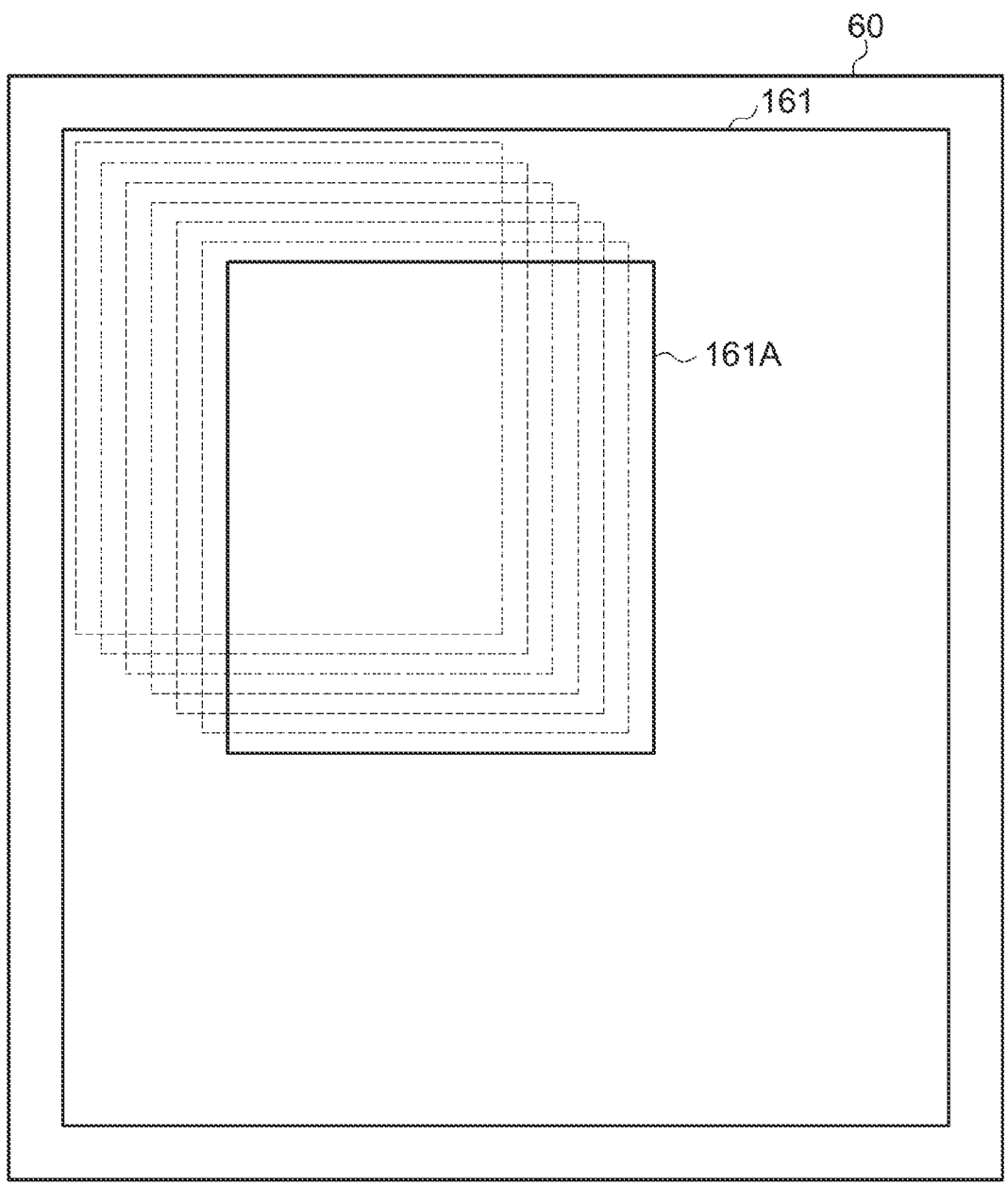
FIG. 37 is a diagram illustrating an example of the order in which the electronic cassette according to the fourth embodiment is moved.

In Step S154, the driving of the motors 158D and 158G is controlled to move the position of the electronic cassette 32 in a predetermined order. After the movement ends, the process proceeds to Step S150. The electronic cassette 32 may be moved such that the region irradiated with the radiation X in the detection region 161 of the radiation detector 60 is not scattered, for example, the electronic cassette 32 may be moved such that the regions irradiated with the radiation X do not overlap each other. In addition, the electronic cassette 32 may be moved at a predetermined distance interval such that portions of the irradiation regions overlap each other. FIG. 32 shows a case in which the electronic cassette 32 is sequentially moved up and down such that portions of a region 161A irradiated with the radiation X in the detection region 161 of the radiation detector 60 overlap each other. FIG. 37 shows a case in which the region 161A irradiated with the radiation X is moved in the unit of pixel columns in the detection region 161 of the radiation detector 60. FIG. 33 shows a case in which the electronic cassette 32 is sequentially moved such that the regions 161A irradiated with the radiation X, which are rectangular blocks, do not overlap each other in the detection region 161 of the radiation detector 60. In FIG. 32, a portion of the irradiation region represented by a dashed line is displaced in order to discriminate the moved irradiation region. In a case in which the frame rate of fluorography is low, the irradiation region 161A may be moved by any method. However, in a case in which the frame rate is high, the methods shown in FIGS. 31 and 37 are preferable.

As described above, according to this embodiment, the position of the electronic cassette 32 is moved such that the irradiation range of the radiation X is not out of the detection region 161 during fluorography. Therefore, the radiation X is emitted to the detection region 161 of the radiation detector 60 while being dispersed. As a result, it is possible to prevent the deterioration of a specific portion of the detection region 161 of the radiation detector 60.

In each of the above-described embodiments, the invention is applied to the radiographic apparatus that performs radiography using the electronic cassette, but it is not limited thereto. The invention may be applied to a stationary radiographic apparatus including the radiation detector 60.

In each of the above-described embodiments, the electronic cassette 32 is moved two-dimensionally while the detection region 161 is maintained so as to face the radiation X, but the invention is not limited thereto. For example, the electronic cassette 32 may be rotated while the detection region 161 is maintained so as to face the radiation X. The rotation of the electronic cassette 32 makes it possible to move the region irradiated with the radiation X in the detection region 161.

Figure 34:
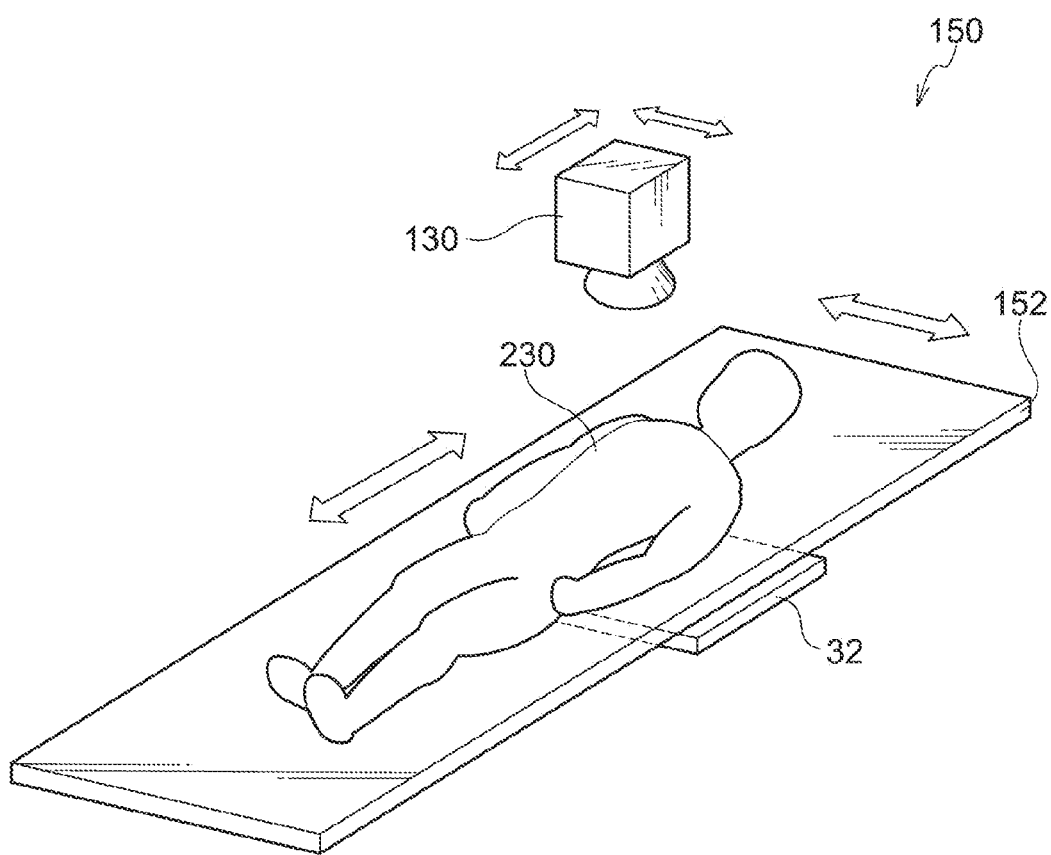
FIG. 34 is a perspective view schematically illustrating a supine position imaging table according to another embodiment in which a top board can be moved in the horizontal direction.

In each of the above-described embodiments, the region irradiated with the radiation X is moved in the detection region 161 of the radiation detector 60 by the movement of the electronic cassette 32, but the invention is not limited thereto. For example, in order to move the region irradiated with the radiation X in the detection region 161 of the radiation detector 60, the radiation source 130 may be moved, the radiation source 130 may be configured so as to be swung, or a diaphragm device capable of changing the region irradiated with radiation may be provided to change the emission direction of radiation from the radiation source 130. For example, as shown in FIG. 34, the supine position imaging table 150 is configured such that the top board 152 can be moved in the horizontal direction, the radiation source 130 and the top board 152 are moved in the horizontal direction in synchronization with each other, and the trimming range of the captured image is moved in correspondence with the horizontal movement. In this way, it is possible to move the region irradiated with the radiation X in the detection region 161 of the radiation detector 60 while performing fluorography on an imaging portion.

In the third embodiment, the number of imaging operations is used as the correlation value correlated with the amount of radiation emitted, but the invention is not limited thereto. For example, the correlation value may be the amount of radiation or the irradiation time.

In a case in which the radiographic apparatus performs the still image capture mode that captures one image at a time and the fluorography mode that continuously captures images to obtain a moving image, in both cases, the amount of radiation generated from the radiation generating apparatus 34, an operation for reading the charge stored in the storage capacitor 68 of each pixel unit 74 of the radiation detector 60, and the operation conditions, such as the gain of a charge signal in the signal processing unit 82, are changed in the still image capture mode and the fluorography mode.

FIG. 17 shows an example of the amount of radiation and the operation conditions in the fluorography mode and the still image capture mode.

In the still image capture mode, radiation is emitted to the patient for the time required for imaging to capture an image. However, in the fluorography mode, radiation is continuously emitted to the patient for the imaging period to capture an image. Therefore, in the fluorography mode, in order to significantly reduce the amount of radiation emitted to the patient, the amount of radiation per unit time is several tenths to one-hundredth of that in the still image capture mode. In addition, the fluorography mode requires a maximum of 60 frames/second to 90 frames/second. In order to read the image, the fluorography mode requires sensitivity and reliability that are several tens of times higher than those of the still image capture mode. Meanwhile, in order to obtain a high-resolution image for diagnosis, the still image capture mode requires a dynamic range close to four digits, but the fluorography mode requires a dynamic range of about two digits.

For example, the fluorography mode is performed for one minute under the following conditions: the frame rate is 30 FPS and the amount of radiation per unit time is 0.1 times that of the still image capture mode. In this case, the amount of radiation emitted once in the fluorography mode is 180 times (0.1×30 FPS×60 SEC=180) the amount of radiation emitted once in the still image capture mode. The number of imaging operations for one minute in the fluorography mode is 1800 (30 FPS×60 SEC=1800).

For example, in a case in which the correlation value is the number of imaging operations and one frame in the fluorography mode is counted as one time, the number of imaging operations in the fluorography mode is very small, that is, one-tenth of the amount of radiation emitted in a case in which the still images are captured by the same number of imaging operations. In a case in which a series of fluorography is counted as one imaging operation, the number of imaging operations in the fluorography mode is very large, that is, 180 times the amount of radiation emitted by one still image capture operation.

In a case in which the number of imaging operations is used as the correlation value, the number of imaging operations may be counted in one of the still image capture mode and the fluorography mode, and the number of imaging operations in the other mode may be converted into the number of imaging operations in the one mode. For example, in a case in which the number of imaging operations in the still image capture mode is counted, the amount of radiation per unit time with respect to the still image capture mode×the frame rate×the fluorography period (seconds) is calculated from fluorography conditions (the amount of radiation per unit time with respect to the still image capture mode and the frame rate) and the fluorography period (seconds). In this way, it is possible to convert the number of imaging operations in the fluorography mode into the number of imaging operations in the still image capture mode. For example, in a case in which the number of imaging operations in the fluorography mode is counted, the division of the number of imaging operations in the still image capture mode by 0.1 is calculated from the amount of radiation (0.1 times) per unit time with respect to the still image capture mode. In this way, it is possible to convert the number of imaging operations in the still image capture mode into the number of imaging operations in the fluorography mode.

FIG. 18 shows an example of a correlation information update program in a case in which the number of imaging operations in the still image capture mode is counted. The same portions as those in the first embodiment (FIG. 13) are denoted by the same reference numerals and a description thereof will be omitted.

In Step S30, it is determined whether the fluorography mode is performed. When the determination result is "Yes", the process proceeds to Step S32. On the other hand, when the determination result is "No", the process proceeds to Step S40. When the still image capture mode is performed, the process proceeds to Step S40.

In Step S32, a conversion process of converting the number of imaging operations in the fluorography mode into the number of imaging operations in the still image capture mode is performed.

For example, in a case in which the fluorography mode is performed for one minute under the following conditions: the frame rate is 30 FPS and the amount of radiation per unit time is 0.1 times that of the still image capture mode, the number of imaging operations in the fluorography mode is converted into 180 imaging operations (0.1×30 FPS×60 SEC=180) in the still image capture mode.

In Step S34, in the number of imaging operations in each divided area 161A indicated by the correlation information stored in the HDD 110, the number of imaging operations converted in Step S32 is added to the number of imaging operations in the divided area 161A specified as the imaging area by the process of the imaging area specifying program, and the process ends.

The correspondence between the fluorography conditions (for example, the amount of radiation per unit time with respect to the still image capture mode, the frame rate, and the imaging time (the time from the first frame to the last n-th frame)) and the number of imaging operations in the still image capture mode may be stored as correspondence information in the HDD 110 in advance, and the number of imaging operations in the still image capture mode corresponding to the number of imaging operations in the fluorography mode may be calculated on the basis of the correspondence information which is stored in the HDD 110 in advance.

Even in a case in which the irradiation time is used as the correlation value, the irradiation time in one of the still image capture mode and the fluorography mode may be accumulated. Then, the irradiation time in the other mode may be converted into the irradiation time in the one mode and then accumulated. For example, in a case in which the irradiation time in the still image capture mode is accumulated, the product of the amount of radiation per unit time in the still image capture mode and the fluorography period (seconds) may be calculated from the fluorography conditions (the amount of radiation per unit time with respect to the still image capture mode) and the fluorography period (seconds). In this way, the irradiation time in the fluorography mode may be converted into the irradiation time in the still image capture mode. In addition, for example, in a case in which the irradiation time in the fluorography mode is accumulated, the division of the irradiation time in the still image capture mode by 0.1 is calculated from the irradiation time (0.1 times) per unit time with respect to the still image capture mode. In this way, it is possible to convert the irradiation time in the still image capture mode into the irradiation time in the fluorography mode.

In the fluorography mode, in some cases, the radiation generating apparatus 34 generates radiation in synchronization with the imaging timing of each frame, and emits radiation in a pulse shape to the electronic cassette 32. In this case, in a case in which the irradiation time and the amount of radiation are used as the correlation value, it is preferable that the time between the frames in the fluorography mode is not considered as the irradiation time.

The sensitivity of CsI is reduced as the amount of radiation emitted increases. Therefore, in a case in which the CsI of the scintillator 204 is a columnar crystal, the indirect-conversion-type radiation detector 60 is used to calculate the cumulative amount of radiation for each of predetermined plural divided areas 61A divided from the detection region 61. In a case in which the cumulative amount of radiation is equal to an allowable value, it is possible to prevent a partial reduction in sensitivity by changing the imaging area. In particular, in the moving image capture mode, the amount of radiation for one frame is small, but the number of captured images is large. Therefore, the total amount of radiation is large. Therefore, in the moving image capture mode, it is preferable to change the imaging area in order to maintain the sensitivity.

The correlation value correlated with the amount of radiation may be stored for each imaging date and time. For example, the correlation values may be accumulated and stored for each predetermined period, such as a day. In addition, information related to the intensity (energy) of radiation may be stored together with the correlation value.

When high-intensity (high-energy) radiation is emitted, a temporary variation (so-called deep trap) in the sensitivity of CsI occurs. Specifically, as shown in FIG. 41, the gradient of the amount of light emitted with respect to the amount of radiation emitted in one imaging operation is changed from a line A to a line B, and the sensitivity is improved. As shown in FIG. 42, a variation Δ in the gradient of the sensitivity line is reduced over about several days. The degree of recovery of the reduction in the variation Δ of the gradient of the sensitivity line varies depending on the temperature of the CsI. As the temperature of the CsI increases, the reduction rate of the variation Δ increases. When a recovery coefficient is 1 at a general operation temperature and storage temperature (for example, 25° C.), the recovery coefficient at, for example, 10° C. or less is 0.5 and the recovery coefficient at 40° C. or more is 2.

Therefore, in the electronic cassette 32, in a case in which an imaging area including a specific portion in which sensitivity is changed is used to perform an imaging operation after radiation with a predetermined intensity or more, which causes a variation in sensitivity, is emitted to a specific portion of the detection region 61 of the radiation detector 60, image sticking (so-called ghosting) occurs due to unevenness in the sensitivity of the captured radiological image since the sensitivity of the specific portion is changed.

Irradiation information related to the intensity or emission time of radiation emitted to each of the divided areas 61A may be further stored in the HDD 110, and the imaging area may be specified on the basis of the irradiation information such that the divided area in which the recovery period required to recover a temporary variation in sensitivity caused by the emission of radiation with sufficient intensity to cause the temporary variation in sensitivity has not elapsed is out of the imaging area or the divided area does not overlap a portion of interest of the imaging portion. For example, irradiation information indicating whether radiation with a predetermined intensity or more causing a variation in sensitivity each predetermined period, such as a day, is emitted to each of the divided areas 61A may be stored. When a radiological image is captured, the imaging area may be specified such that the divided area 61A in which a predetermined recovery period (for example, 2 days) required to recover a temporary variation in sensitivity has not elapsed is excluded, or the imaging area may be specified such that the divided area 61A in which the recovery period has not elapsed does not overlap a portion of interest of the imaging portion. In this way, it is possible to prevent image sticking due to a temporary variation in the sensitivity of the CsI and maintain the imaging performance.

Information related to the position of the portion of interest may be stored for each imaging portion in advance, the operator may input the information using the operation panel 102, or the information may be received from another server computer through the network. In addition, plural threshold values of the intensity of radiation causing a variation in sensitivity may be set, the intensity of radiation emitted may be compared with each threshold value, the intensity of radiation emitted may be divided into plural levels, and the recovery period corresponding to each level may be determined.

As described above, the recovery period of the variation in the sensitivity of CsI also varies depending on the temperature.

A temperature sensor may be provided at, for example, the end of the radiation detector 60, the temperature of the radiation detector 60 may be detected by the temperature sensor at any time, and the detected temperature may be stored together with the detection date and time. When a radiological image is captured, the recovery period may be changed on the basis of the temperature state (the average temperature, the maximum temperature, the minimum temperature, and the accumulated temperature) of the radiation detector 60 after radiation with predetermined intensity or more is emitted. For example, in a case in which the average temperature of the radiation detector 60 is 10° C. after radiation with a predetermined intensity or more is emitted, the recovery period may be changed so as to be two times longer than that in a case in which the average temperature of the radiation detector 60 is 25° C. after radiation with a predetermined intensity or more is emitted, or in a case in which the average temperature is 40° C., the recovery period may be changed so as to be half of that in a case in which the average temperature is 25° C.

In the fourth embodiment, the electronic cassette 32 is moved in a predetermined order such that the irradiation range of the radiation X is not out of the detection region 161, but the invention is not limited thereto. For example, similar to the third embodiment, the correlation value correlated with the amount of radiation in each divided area 161A may be stored, the movement order in which the divided area 161A with the maximum correlation value is out of the irradiation range of the radiation X may be calculated, and the electronic cassette may be moved in the movement order.

In the fourth embodiment, the electronic cassette 32 is moved during fluorography, but the invention is not limited thereto. For example, when fluorography starts, the electronic cassette 32 may be moved in advance such that the radiation is emitted to the detection region 161 of the radiation detector 60 while being dispersed in plural fluorographic operations, and the electronic cassette 32 may not be moved during fluorography.

When a still image is captured in the fluorography mode, the electronic cassette 32 may be moved during at least one of the switching timing from the fluorography mode to the still image capture mode and the switching timing from the still image capture mode to the fluorography mode to move the irradiation region in the detection region.

Figure 36A:
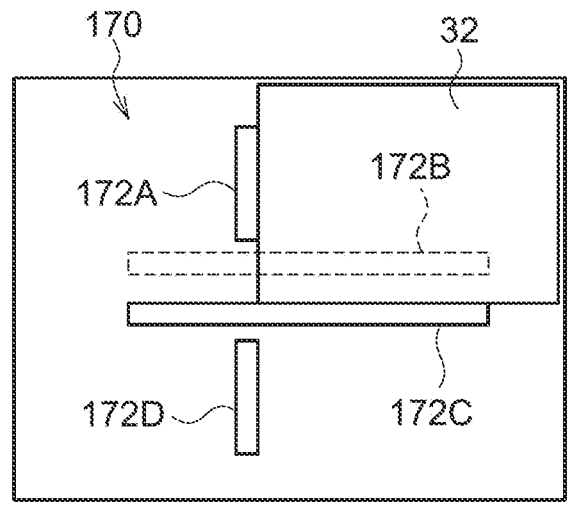
FIGS. 36A to 36C are plan views illustrating the accommodation of an electronic cassette in an accommodating unit of an imaging table according to another embodiment.
Figure 36B:
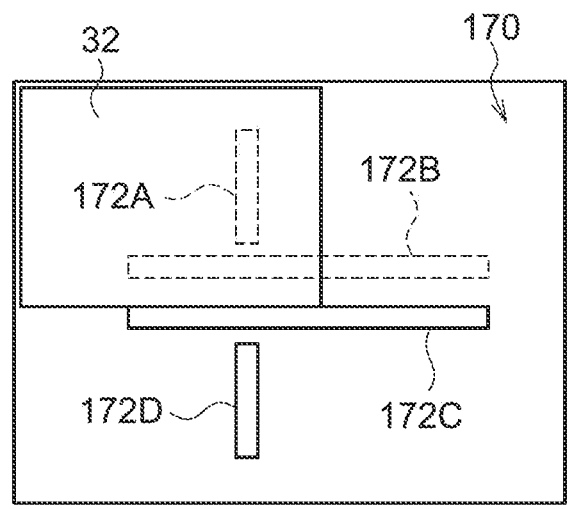
Figure 36C:
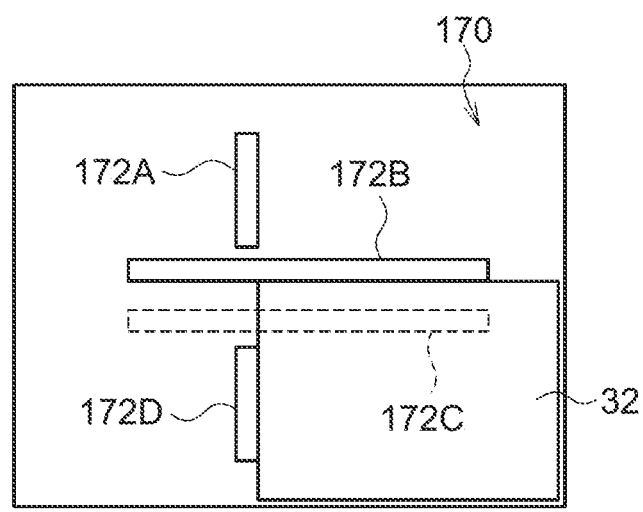

In each of the above-described embodiments, the movement mechanism that moves the electronic cassette 32 is provided in the imaging table, but the invention is not limited thereto. For example, as shown in FIG. 35, an accommodating unit 170 that accommodates the electronic cassette 32 and has a size larger than that of the electronic cassette 32 is provided in the imaging table, and plural partition members 172A to 172D are provided in the accommodating unit 170. Each of the partition members 172A to 172D is configured such that the protrusion and non-protrusion thereof can be switched by, for example, a solenoid in the accommodating unit 170. As shown in FIGS. 36A to 36C, a combination of the partition members 172A to 172D protruding in the accommodating unit 170 may be changed to change the position of the electronic cassette 32 accommodated in the accommodating unit 170. In FIGS. 36A to 36C, the partition members 172A to 172D protruding in the accommodating unit 170 are represented by a solid line and the partition members 172A to 172D that do not protrude are represented by a dashed line.

In the third embodiment, the size information is stored in order to respond to plural imaging portions, but the invention is not limited thereto. For example, in a case in which the size of the area required for imaging is predetermined, it is not necessary to store the size information of each imaging portion.

In the fourth embodiment, the size information may be stored in the HDD 110, the console 42 may designate an imaging portion during fluorography, and the irradiation range of radiation may be determined from the size of the divided area 161A corresponding to the designated imaging portion on the basis of the size information.

In the first and fourth embodiments, in a case in which the size information is stored, the movable diaphragm device 131 may be controlled according to the size of the area required for imaging.

In the third embodiment, the number of imaging operations for each combination of the divided areas 161A by which a size capable of capturing an imaging portion is obtained is summed, and the combination of the divided areas 161A with the minimum sum is specified as the imaging area. However, the invention is not limited thereto. For example, the maximum value of the number of imaging operations in each divided area 161A may be calculated for each combination of the divided areas 161A by which a size capable of capturing an imaging portion is obtained, and a combination of the divided areas 161A with the smallest value of the maximum value may be specified as the imaging area.

In the third embodiment, the detection region 161 is divided into 3×3 (=9) divided areas 161A, but the invention is not limited thereto. For example, the detection region 161 may be finely divided into 5×4 divided areas, and an area corresponding to each pixel unit 74 may be used as the divided area.

In the third embodiment, combinations of the identification numbers of the divided areas 161A by which each size of the area required for imaging is obtained are stored as the divided area combination information in advance, but the invention is not limited thereto. For example, combinations of the identification numbers of the divided areas 161A by which the size of the area required for imaging is obtained may be calculated by an operation.

In the fourth embodiment, whenever a predetermined period of time has elapsed from the movement of the previous position of the electronic cassette 32, the position of the electronic cassette 32 is moved. However, the invention is not limited thereto. For example, during fluorography, the position of the electronic cassette 32 may be continuously moved. In addition, the position of the electronic cassette 32 may be moved each time a predetermined number of imaging operations are performed or a predetermined amount of radiation is emitted.

In the third embodiment, the position of the electronic cassette 32 in the imaging unit 46 may be changed each time a predetermined number of imaging operations are performed or at a predetermined interval (for example, one day).

In addition, the structure of the RIS 10 (see FIG. 1), the structure of the radiography room 44 (see FIGS. 21 and 27), the structure of the imaging table (see FIGS. 22, 24, 28, 29, 34, 35, and 36A to 36C), the structure of the electronic cassette 32 (see FIG. 23), the structure of the movable diaphragm device 131 (see FIG. 5), and the structure of the imaging system 18 (see FIGS. 25 and 30) according to each of the above-described embodiments are only illustrative. An unnecessary portion may be removed, a new component may be added, or the connection state may be changed, without departing from the scope and spirit of the invention.

In the electronic cassette 32 according to each embodiment, the radiation detector 60 may be provided such that the radiation X is emitted from the TFT substrate 66.

Figure 40:
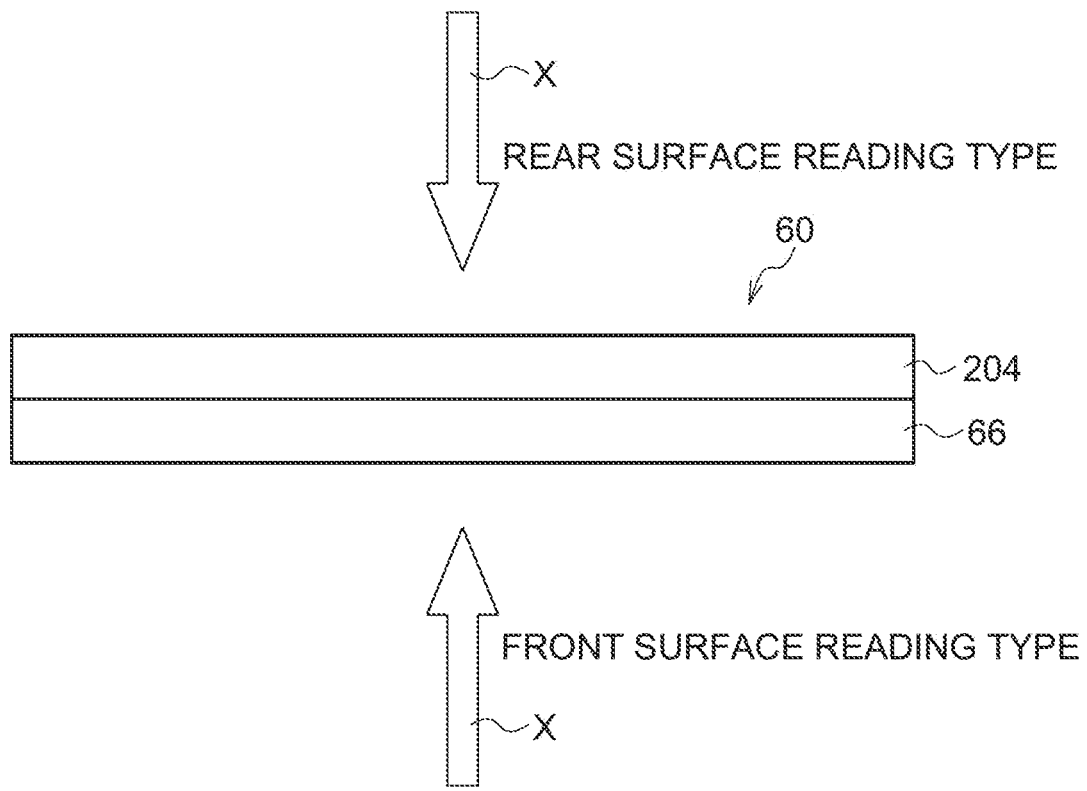
FIG. 40 is a cross-sectional view schematically illustrating the structure of three pixel units of a radiation detector according to the embodiment.

As shown in FIG. 40, in a case in which the radiation detector 60 is a so-called rear surface reading type (so-called PSS (Penetration Side Sampling) type) in which radiation is emitted from the side where the scintillator 204 is formed and the TFT substrate 66 that is provided on the side opposite to the incident surface of the radiation reads a radiological image, high-intensity light is emitted from the upper surface (the surface opposite to the TFT substrate 66) of the scintillator 204 in FIG. 40. When the radiation detector 60 is a so-called front surface reading type (so-called ISS (Irradiation Side Sampling) type) in which radiation is emitted from the side of the TFT substrate 66 and the TFT substrate 66 that is provided on the incident surface of the radiation reads a radiological image, the radiation passing through the TFT substrate 66 is incident on the scintillator 204 and high-intensity light is emitted from the surface of the scintillator 204 close to the TFT substrate 66. Each of the sensor units 72 provided on the TFT substrate 66 generates charge using light emitted from the scintillator 204. Therefore, in the radiation detector 60 of the front surface reading type, the emission position of the scintillator 204 with respect to the TFT substrate 66 is closer to that in the radiation detector 60 of the rear surface reading type. As a result, the resolution of the radiological image captured in the front surface reading type is higher than that of the radiological image captured in the rear surface reading type.

In the radiation detector 60, the photoelectric conversion film 214 is made of an organic photoelectric conversion material and radiation is hardly absorbed by the photoelectric conversion film 214. Therefore, in the radiation detector 60 according to this embodiment, in the front surface reading type, even when radiation passes through the TFT substrate 66, the amount of radiation absorbed by the photoelectric conversion film 214 is small. Therefore, it is possible to prevent a reduction in sensitivity for the radiation X. In the front surface reading type, radiation passes through the TFT substrate 66 and reaches the scintillator 204. However, as such, in a case in which the photoelectric conversion film 214 of the TFT substrate 66 is made of an organic photoelectric conversion material, the radiation is hardly absorbed by the photoelectric conversion film 214 and it is possible to reduce the attenuation of the radiation. The radiation detector 60 is suitable for the front surface reading type.

Both the amorphous oxide forming the active layer 224 of the TFT 70 and the organic photoelectric conversion material forming the photoelectric conversion film 214 can be used to form a film at a low temperature. Therefore, the substrate 200 can be made of a plastic resin, aramid, or bio-nanofiber that absorbs a small amount of radiation. Since the substrate 200 formed in this way absorbs a small amount of radiation, it is possible to prevent a reduction in sensitivity for the radiation X even when radiation passes through the TFT substrate 66 in the front surface reading type.

For example, in a case in which the radiation detector 60 is adhered to the irradiation surface 56 of the housing 54 such that the TFT substrate 66 faces the irradiation surface 56 and the substrate 200 is made of a plastic resin with high rigidity, aramid, or bio-nanofiber, it is possible to reduce the thickness of the irradiation surface 56 of the housing 54 since the radiation detector 60 has high rigidity. In addition, in a case in which the substrate 200 is made of a plastic resin with high rigidity, aramid, or bio-nanofiber, the radiation detector 60 has flexibility. Therefore, even when an impact is applied to the irradiation surface 56, the radiation detector 60 is less likely to be damaged.

The structure of the correlation information, the size information, and the divided area combination information (see FIGS. 8 to 10) according to the above-described embodiments are only illustrative. Unnecessary information may be removed, new information may be added, or the information may be changed, without departing from the scope and spirit of the invention.

The flow of the processes of the imaging area specifying program, the correlation information update program, and the movement processing program according to the above-described embodiments (see FIGS. 26, 13, 31, and 18) are only illustrative. An unnecessary step may be removed, a new step may be added, or the procedure may be changed, without departing from the scope and spirit of the invention.

What is claimed is:

1. An imaging area specifying apparatus comprising:
a storage component that stores, as correlation information, a correlation value correlated with an amount of radiation emitted to each of a plurality of predetermined areas divided from a detection region of a radiation detector that outputs an electrical signal indicating a radiological image represented by radiation which is emitted to the detection region; and
a specifying component that specifies an imaging area capable of capturing the radiological image, which has a predetermined size, while preventing variations in the amount of radiation emitted to each of the plurality of predetermined areas, on the basis of the correlation information stored in the storage component.

2. The imaging area specifying apparatus of claim 1, further comprising:
an acquiring component that acquires imaging portion information indicating an imaging portion, which is an imaging target,
wherein the storage component further stores size information indicating the size of an area required to capture the radiological image of each imaging portion of an object whose radiological image is to be captured, and
the specifying component calculates the size of an area required to capture the image of the imaging portion indicated by the imaging portion information acquired by the acquiring component on the basis of the size information stored in the storage component, and specifies an imaging area capable of capturing a radiological image with the calculated size while preventing variations in the amount of radiation emitted to each of the plurality of predetermined areas on the basis of the correlation information.

3. The imaging area specifying apparatus of claim 1, wherein the specifying component calculates sums of the correlation values of the plurality of predetermined areas in each range with the size of an area required to capture the image of an imaging portion in the detection region on the basis of the correlation information, and specifies a range with a minimum sum as the imaging area.

4. The imaging area specifying apparatus of claim 1, wherein the specifying component calculates the maximum value of the correlation value of each predetermined area in each range with the size of an area required to capture the image of an imaging portion in the detection region on the basis of the correlation information, and specifies the range with the smallest value of the maximum values as the imaging area.

5. The imaging area specifying apparatus of claim 1, further comprising:
a presentation component that presents the imaging area specified by the specifying component.

6. The imaging area specifying apparatus of claim 1, further comprising:
a control component that controls a limiting component, which limits an irradiation range of the radiation, of a radiation generating apparatus which generates radiation such that the radiation is emitted from the radiation generating apparatus to the imaging area specified by the specifying component.

7. The imaging area specifying apparatus of claim 1, further comprising:
a conversion component,
wherein the correlation value is a number of imaging operations or an emission time of radiation in one mode of a still image capture mode that captures one image at a time or a fluorography mode that continuously captures an image, and
the conversion component converts the correlation value in the other mode of the still image capture mode or the fluorography mode into the correlation value in the one mode.

8. A radiographic system comprising:
a radiographic apparatus including a radiation detector that outputs an electrical signal indicating a radiological image represented by radiation which is emitted to a detection region for detecting the radiation;
an imaging area specifying apparatus including a storage component that stores, as correlation information, a correlation value correlated with the amount of radiation emitted to each of a plurality of predetermined areas divided from the detection region, and
a specifying component that specifies an imaging area capable of capturing the radiological image, which has a predetermined size, while preventing variations in the amount of radiation emitted to each of the plurality of predetermined areas, on the basis of the correlation information stored in the storage component; and
a presentation component that presents the imaging area specified by the specifying component.

9. The radiographic system of claim 8, further comprising:
a detection component that detects whether an imaging portion is disposed at a position where a radiological image is captured in the imaging area of the radiation detector specified by the specifying component; and
a permission component that permits the emission of radiation from a radiation generating apparatus which generates the radiation to the imaging area in a case in which the detection component detects that the imaging portion is disposed at the position where the radiological image is captured in the imaging area.

10. The radiographic system of claim 9, wherein the radiation detector converts radiation into light using a scintillator and outputs an electrical signal indicating a radiological image represented by the light, and the scintillator is formed so as to include a columnar crystal of a phosphor material.

11. The radiographic system of claim 10, wherein
the storage component further stores irradiation information related to the intensity and emission time of radiation emitted to each of the plurality of predetermined areas, and
the specifying component specifies the imaging area on the basis of the irradiation information such that the predetermined area in which a recovery period required to recover a temporary variation in sensitivity caused by the emission of radiation with sufficient intensity to cause the temporary variation in sensitivity has not elapsed is out of the imaging area, or the predetermined area does not overlap a portion of interest of the imaging portion.

12. The radiographic system of claim 11, further comprising:
a temperature detecting component that detects the temperature of the radiation detector, wherein the specifying component changes the recovery period such that, as the temperature of the radiation detector detected by the temperature detecting component increases, the recovery period is shortened.

13. A method of specifying an imaging area comprising:
storing in a storage component, as correlation information, a correlation value correlated with an amount of radiation emitted to each of a plurality of predetermined areas divided from a detection region of a radiation detector that outputs an electrical signal indicating a radiological image represented by radiation which is emitted to the detection region; and
specifying an imaging area capable of capturing the radiological image, which has a predetermined size, while preventing variations in the amount of radiation emitted to each of the plurality of predetermined areas, on the basis of the correlation information stored in the storage component.

14. A radiographic apparatus comprising:
a radiation detector that outputs an electrical signal indicating a radiological image represented by radiation which is emitted to a detection region for detecting the radiation;
a radiation source that emits the radiation to the radiation detector;
an irradiation region changing component that changes an irradiation region to which the radiation is emitted from the radiation source in the detection region; and
a control component that controls the irradiation region changing component to change the position of the irradiation region in the detection region such that the radiation is emitted to the detection region,
wherein the control component controls the irradiation region changing component in a fluorography mode that continuously captures an image such that the irradiation region is moved in the detection region during fluorography, controls the irradiation region changing component in a still image capture mode that captures one image at a time such that the irradiation region is moved in the detection region in synchronization with the capture of a still image, and controls the irradiation region changing component in the fluorography mode that captures a still image such that the irradiation region is moved in the detection region during at least one of a switching timing from the fluorography mode to the still image capture mode or a switching timing from the still image capture mode to the fluorography mode.

15. The radiographic apparatus of claim 14, wherein the control component controls the irradiation region changing component such that the irradiation region is moved in the detection region each time a predetermined number of fluorographic operations are performed or each time a predetermined amount of radiation is emitted during the fluorography.

16. A radiographic apparatus comprising:
a radiation detector that outputs an electrical signal indicating a radiological image represented by radiation which is emitted to a detection region for detecting the radiation;
a radiation source that emits the radiation to the radiation detector;
an irradiation region changing component that changes an irradiation region to which the radiation is emitted from the radiation source in the detection region;
a control component that controls the irradiation region changing component to change the position of the irradiation region in the detection region such that the radiation is emitted to the detection region;
a storage component that stores, as correlation information, a correlation value correlated with the amount of radiation emitted to each of a plurality of predetermined areas divided from detection region; and
a specifying component that specifies an imaging area capable of capturing a radiological image of a predetermined size while preventing variations in the amount of radiation emitted to each of the plurality of predetermined areas, on the basis of the correlation information stored in the storage component,
wherein the control component controls the irradiation region changing component such that the imaging area specified by the specifying component is the irradiation region.

17. The radiographic apparatus of claim 16, further comprising:
an acquiring component that acquires imaging portion information indicating an imaging portion, which is an imaging target, wherein the storage component further stores size information indicating the size of an area required to capture the radiological image of each imaging portion of an object whose radiological image is to be captured, and
the specifying component calculates a size of an area required to capture the image of the imaging portion indicated by the imaging portion information acquired by the acquiring component on the basis of the size information stored in the storage component, and specifies an imaging area capable of capturing a radiological image with the size while preventing variations in the amount of radiation emitted to each of the plurality of predetermined areas on the basis of the correlation information.

18. The radiographic apparatus of claim 16, wherein the specifying component calculates sums of the correlation values of the divided areas in each range with the size of an area required to capture the image of an imaging portion in the detection region on the basis of the correlation information, and specifies a range with a minimum sum as the imaging area.

19. A radiographic apparatus comprising:
a radiation detector that outputs an electrical signal indicating a radiological image represented by radiation which is emitted to a detection region for detecting the radiation;
a radiation source that emits the radiation to the radiation detector;
an irradiation region changing component that changes an irradiation region to which the radiation is emitted from the radiation source in the detection region; and
a control component that controls the irradiation region changing component to change the position of the irradiation region in the detection region such that the radiation is emitted to the detection region, wherein
the radiation detector converts radiation into light using a scintillator and outputs an electrical signal indicating a radiological image represented by the light, and the scintillator is formed so as to include a columnar crystal of a phosphor material, a storage component storing irradiation information related to the intensity and emission time of radiation emitted to each of the plurality of predetermined areas, and a specifying component specifying the imaging area on the basis of the irradiation information such that the predetermined area in which a recovery period required to recover a temporary variation in sensitivity caused by the emission of radiation with sufficient intensity to cause the temporary variation in sensitivity has not elapsed is out of the imaging area or the predetermined area does not overlap a portion of interest of the imaging portion.

20. The radiographic apparatus of claim 19, further comprising:

a temperature detecting component that detects the temperature of the radiation detector, wherein the specifying component changes the recovery period such that, as the temperature of the radiation detector detected by the temperature detecting component increases, the recovery period is shortened.

* * * * *